(12) United States Patent
Maa et al.

(10) Patent No.: US 7,229,645 B2
(45) Date of Patent: Jun. 12, 2007

(54) SPRAY FREEZE-DRIED COMPOSITIONS

(75) Inventors: Yuh-Fun Maa, Fremont, CA (US); Steven J. Prestrelski, Fremont, CA (US); Terry L. Burkoth, Fremont, CA (US)

(73) Assignee: Powderject Research Limited, Oxford (GB)

( * ) Notice: Subject to any disclaimer, the term of this patent is extended or adjusted under 35 U.S.C. 154(b) by 258 days.

(21) Appl. No.: 10/164,594

(22) Filed: Jun. 10, 2002

(65) Prior Publication Data

US 2003/0202978 A1    Oct. 30, 2003

Related U.S. Application Data

(60) Provisional application No. 60/296,939, filed on Jun. 8, 2001.

(51) Int. Cl.
*A61K 9/14* (2006.01)
*A61K 31/28* (2006.01)

(52) U.S. Cl. .................. 424/489; 424/499; 424/184.1; 424/204.1; 424/234.1; 514/492

(58) Field of Classification Search .................. 34/288, 34/284; 424/489, 499, 184.1, 204.1, 234.1; 514/492
See application file for complete search history.

(56) References Cited

U.S. PATENT DOCUMENTS

| | | | |
|---|---|---|---|
| 3,909,957 A * | 10/1975 | Passey ........................... | 34/92 |
| 4,578,270 A | 3/1986 | Csizer et al. | |
| 4,710,378 A * | 12/1987 | Ohtomo et al. ........... | 424/227.1 |
| 5,019,400 A * | 5/1991 | Gombotz et al. ............ | 424/497 |
| 5,208,998 A * | 5/1993 | Oyler, Jr. ..................... | 34/288 |
| 5,561,121 A | 10/1996 | Ku et al. | |
| 5,580,856 A * | 12/1996 | Prestrelski et al. ........... | 514/21 |
| 5,902,565 A * | 5/1999 | Cox et al. ................... | 424/1.29 |
| 5,955,448 A | 9/1999 | Colaco et al. | |
| 6,284,282 B1 * | 9/2001 | Maa et al. .................. | 424/499 |
| 6,284,283 B1 * | 9/2001 | Costantino et al. ......... | 424/501 |

FOREIGN PATENT DOCUMENTS

| | | |
|---|---|---|
| EP | 0130619 B1 | 3/1989 |
| EP | 0438747 A1 | 7/1991 |
| WO | WO 90/13285 A1 | 11/1990 |
| WO | WO 90/13780 A1 | 11/1990 |
| WO | WO 97/48485 A1 | 12/1997 |
| WO | WO 01/64188 A1 | 9/2001 |
| WO | WO 01/93829 A2 | 12/2001 |

OTHER PUBLICATIONS

"Coffee, instant, regular, powder", NutritionData (Jan. 24, 2005).*
"Orange juice, frozen concentrate, unsweetened, diluted with 3 volume water", NutritionData (Jan. 24, 2005).*
Bellhouse, B.J. et al., "Needleless delivery of drugs in dry powder form, using shock waves and supersonic gas flow," Plenary Lecture 6, 21st International Symposium on Shock Waves, 1997, Australia.
Burkoth, Terry L. et al., "Transdermal and Transmucosal Powdered Drug Delivery," Critical Reviews™ in Therapeutic Drug Carrier Systems, 1999, pp. 331-384, vol. 16, No. 4, Stephen Bruck Ed., Begell House Inc., New York, NY.
Etzler, Frank M. et al., "Particle Size Analysis: a Comparative Study of Various Methods," Part. Part. Syst. Charact., 1995, pp. 217-224, vol. 12, VCH Verlagsgesellschaft mbH, Weinheim, Germany.
Maa, Yuh-Fun et al., "Protein Inhalation Powders: Spray Drying vs. Spray Freeze Drying," Pharmaceuticals Research, (1999), pp. 249-254, vol. 16 (2), Plenum Publishing Corp.
Mumenthaler, M. et al., "Atmospheric spray-freeze drying: a suitable alternative in freeze-drying technology," Int. J. Pharmaceutics, 1991, pp. 97-110, vol. 72, Elsevier Sciences Publishers B.V.
International Search Report Dec. 20, 2002, PCT/GB02/02677.

* cited by examiner

*Primary Examiner*—Johann Richter
*Assistant Examiner*—Frank I Choi
(74) *Attorney, Agent, or Firm*—Sharon E. Crane; Bingham McCutchen, LLP

(57) ABSTRACT

A process for producing a powder comprises spray freeze-drying an aqueous solution or suspension comprising a pharmaceutical agent, said solution or suspension having a solids content of 20% by weight or more. The spray freeze-dried powder may be administered to a subject via a needleless syringe.

18 Claims, 19 Drawing Sheets c.

1. Molecular Weight Marker
2. 138-20-1
3. 138-20-2
4. 138-20-3
5. 138-20-4A
6. 138-20-4B; <38 µm
9. 108-85-3: CpG
10. Dialyzed HBsAg @ 2-8°C, 1 year

Figure 5.

Figure 12a.
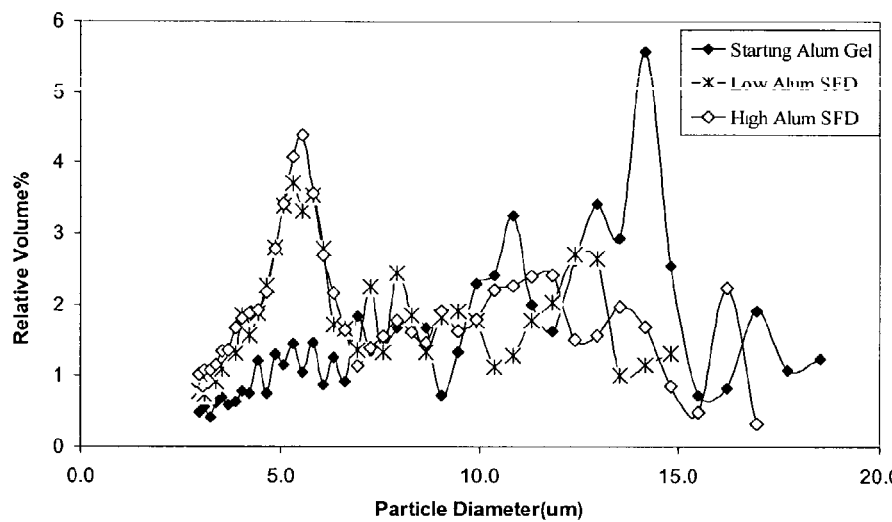
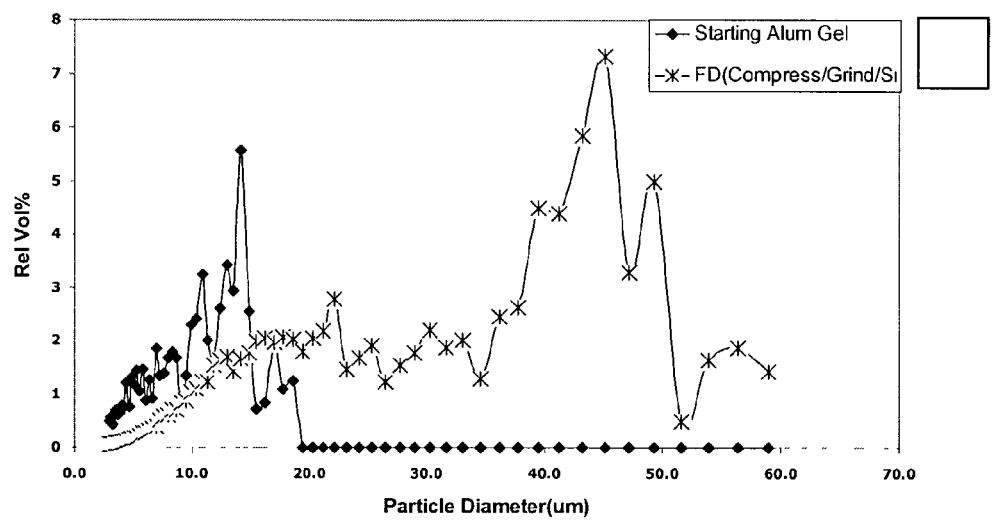
Figure 12b.

Figure 15a. Figure 15b. Figure 15c.
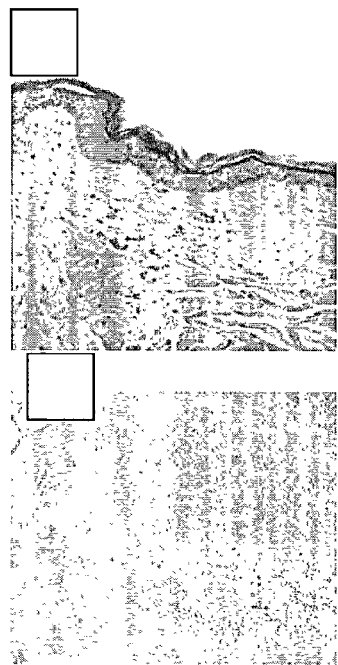
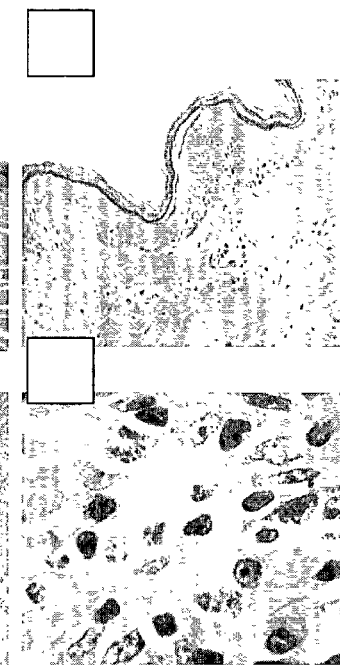
Figure 15d. Figure 15e.

Figure 16a.
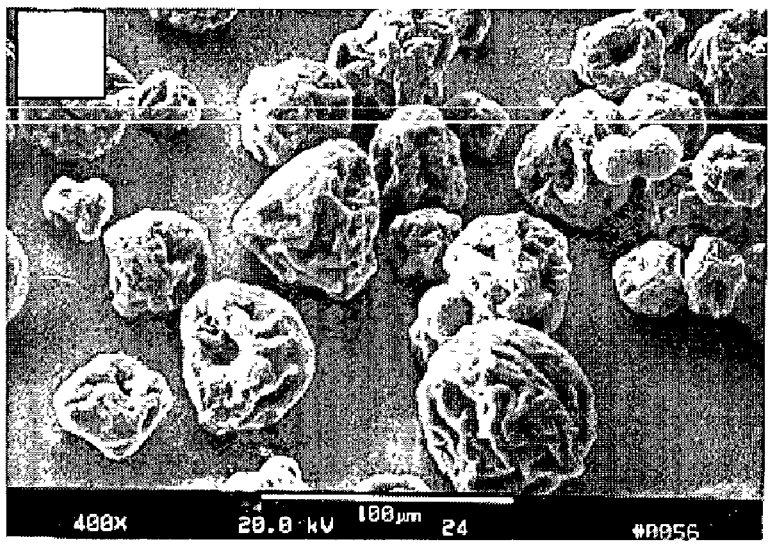
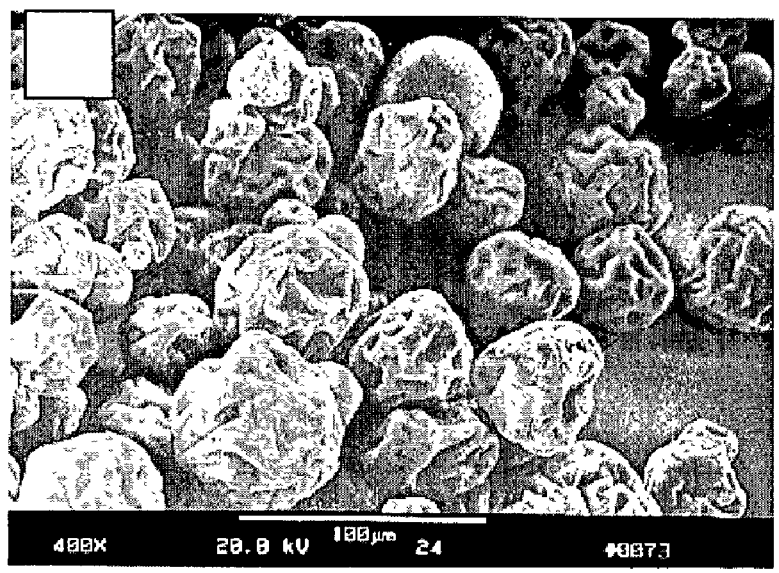
Figure 16b.

Figure 17a.
Figure 17b.
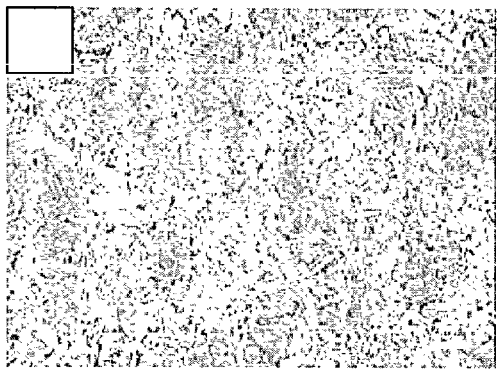
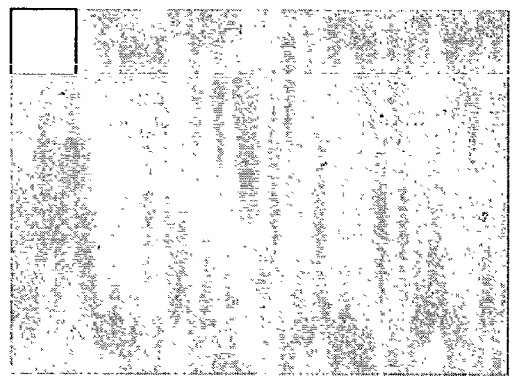
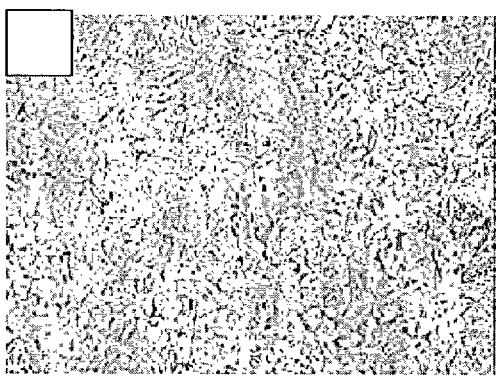
Figure 17c.
Figure 17d.

Figure 18a.  Figure 18b.
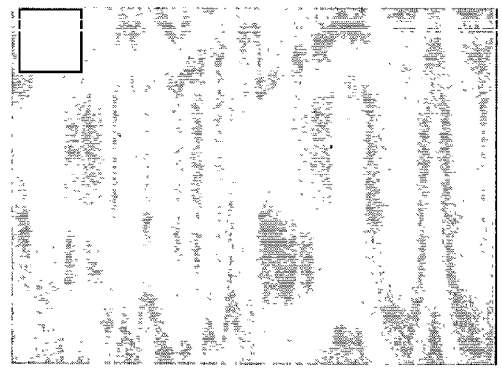 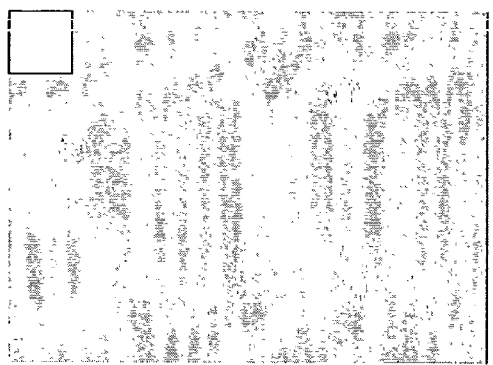
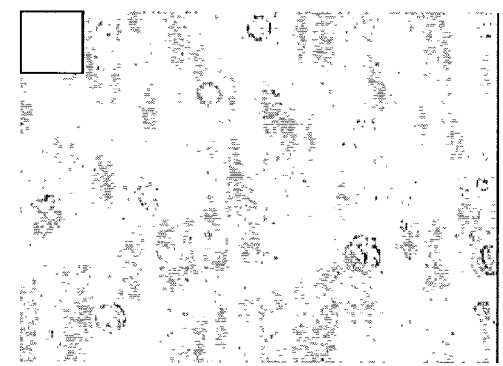 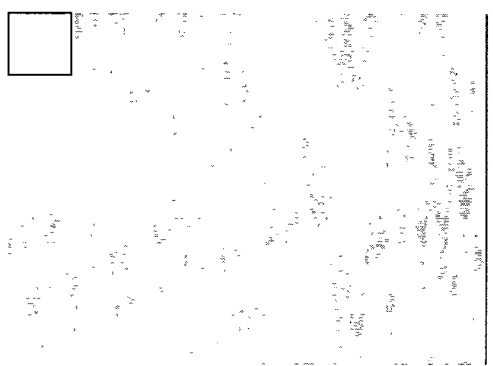
Figure 18c.  Figure 18d.

Figure 19a.
Figure 19b.
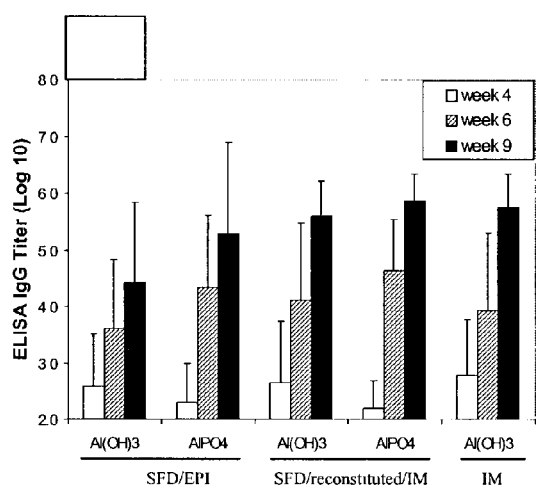
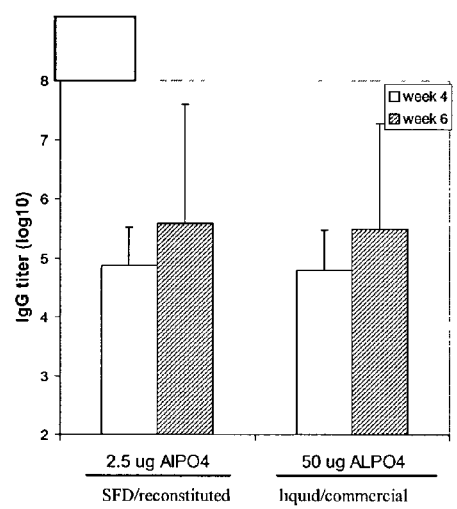

SPRAY FREEZE-DRIED COMPOSITIONS

CROSS-REFERENCE TO RELATED APPLICATIONS

This application is related to U.S. provisional patent application Ser. No. 60/296,939, filed 8 Jun. 2001, from which application priority is claimed pursuant to 35 U.S.C. §119(e)(1) and which application is incorporated herein by reference in its entirety.

FIELD OF THE INVENTION

The invention relates to processes for producing pharmaceutical compositions which are suitable for transdermal particle delivery from a needleless syringe system.

BACKGROUND OF THE INVENTION

The ability to deliver pharmaceutical agents into and through skin surfaces (transdermal delivery) provides many advantages over oral or parenteral delivery techniques. In particular, transdermal delivery provides a safe, convenient and noninvasive alternative to traditional administration systems, conveniently avoiding the major problems associated with oral delivery (e.g. variable rates of absorption and metabolism, gastrointestinal irritation and/or bitter or unpleasant drug tastes) or parenteral delivery (e.g. needle pain, the risk of introducing infection to treated individuals, the risk of contamination or infection of health care workers caused by accidental needle-sticks and the disposal of used needles).

However, despite its clear advantages, transdermal delivery presents a number of its own inherent logistical problems. Passive delivery through intact skin necessarily entails the transport of molecules through a number of structurally different tissues, including the stratum corneum, the viable epidermis, the papillary dermis and the capillary walls in order for the drug to gain entry into the blood or lymph system. Transdermal delivery systems must therefore be able to overcome the various resistances presented by each type of tissue.

In light of the above, a number of alternatives to passive transdermal delivery have been developed. These alternatives include the use of skin penetration enhancing agents, or "permeation enhancers," to increase skin permeability, as well as non-chemical modes such as the use of iontophoresis, electroporation or ultrasound. However, these alternative techniques often give rise to their own unique side effects such as skin irritation or sensitization. Thus, the spectrum of agents that can be safely and effectively administered using traditional transdermal delivery methods has remained limited.

More recently, a novel transdermal drug delivery system that entails the use of a needleless syringe to fire powders (i.e., solid drug-containing particles) in controlled doses into and through intact skin has been described. In particular, commonly owned U.S. Pat. No. 5,630,796 to Bellhouse et al. describes a needleless syringe that delivers pharmaceutical particles entrained in a supersonic gas flow. The needleless syringe is used for transdermal delivery of powdered drug compounds and compositions, for delivery of genetic material into living cells (e.g., gene therapy) and for the delivery of biopharmaceuticals to skin, muscle, blood or lymph. The needleless syringe can also be used in conjunction with surgery to deliver drugs and biologics to organ surfaces, solid tumors and/or to surgical cavities (e.g., tumor beds or cavities after tumor resection). In theory, practically any pharmaceutical agent that can be prepared in a substantially solid, particulate form can be safely and easily delivered using such devices.

To enable powdered drug compositions to be effectively administered via this new needleless syringe technique, the powders should have certain physical characteristics. In particular, the size of the particles which form the powders should be controllable, preferably with a narrow size distribution. Further, the particle density should be high, the particles should be free-flowing under a dry environment and their moisture content should be low. Additional properties of the particles which are desired include a spherical shape and a smooth surface. Each of these properties is important to provide good skin penetration whilst avoiding damage to the particles themselves under the forces required for delivery via needleless syringe.

One of the most important factors in determining the physical characteristics of the powders is the particular manner by which they are produced. Various spray freeze-drying techniques have previously been described for, for example, the preparation of powders for aerosol delivery and microspheres for conventional drug delivery. In these applications, particles are desired to be light and porous, properties which are inherent in powders produced by previously described spray freeze-drying techniques. Such light and porous particles are not suitable for use in needleless syringe devices.

Maa et al. (1999) *Pharmaceuticals Research* 16(2) describe the physical characteristics of spray-freeze-dried particles and their performance as aerosols. The spray freeze-drying process is said to render highly porous particles with a large specific surface area. Maa estimated that the particle density of spray freeze-dried particles is typically approximately one ninth of that of equivalent particles dried by spray-drying.

U.S. Pat. No. 5,019,400 describes a process for preparing microspheres using very cold temperatures to freeze polymer-biologically active agent mixtures into polymeric microspheres with retention of biological activity and material. Polymer is dissolved in a solvent together with an active agent that can be either dissolved in the solvent or dispersed in the solvent in the form of microparticles. The polymer/active agent mixture is atomised into a vessel containing a liquid non-solvent, alone or frozen and overlayed with a liquified gas, at a temperature below the freezing point of the polymer/active agent solution.

When the combination with the liquified gas is used, the atomised droplets freeze into microspheres upon contacting the cold liquified gas, then sink onto the frozen non-solvent layer. The frozen non-solvent is then thawed. As the non-solvent thaws, the microspheres which are still frozen sink into the liquid non-solvent. The solvent in the microspheres then thaws and is slowly extracted into the non-solvent, resulting in hardened microspheres containing active agent either as a homogeneous mixture of the polymer and the active agent or as a heterogeneous two phase system of discrete zones of polymer and active agent.

If a cold solvent is used alone, the atomized droplets freeze upon contacting the solvent, and sink to the bottom of the vessel. As the non-solvent for the polymer is warmed, the solvent in the microspheres thaws and is extracted into the non-solvent, resulting in hardened microspheres.

SUMMARY OF THE INVENTION

The present inventors have surprisingly found that spray freeze-drying a solution or suspension having a high solids content in the solvent produces particles which are quite dense and which perform well in needleless syringe devices. The use of a high solids content starting material minimises the pore formation which occurs during the drying step. Sublimation of frozen solvent away from the particles during drying is the typical cause of pore formation. Maximising the solids content in the solution or suspension, and therefore in the frozen particles, reduces the number and size of pores which form on drying, thus providing denser particles.

The inventors have also found that the use of particular excipients may aid the formation of dense particles. Appropriate excipient compositions allow particles to collapse and densify during freeze-drying. It is also thought that selecting specific excipient compositions may assist particle formation by increasing the solubility of certain guest substances (such as peptides and proteins) in the solvent system. This further aids in maximising the solids content of the solution or suspension.

The present invention therefore enables the spray freeze-drying process, with its attendant advantages, to be adapted to needleless syringe requirements. The particles of the invention have a well-defined size and a high density, together with other mechanical properties which collectively are suitable for transdermal delivery via a needleless syringe. The present spray freeze-drying process is a simple technique which is highly suitable for scaling-up to commercial production levels. In addition, it has, as yet, been found to be entirely formulation independent. The technique can therefore be applied to almost any pharmaceutical formulation, a factor which further adds to the commercial viability of the present invention.

Accordingly, the present invention provides a process for the preparation of a powder, which process comprises the step of spray freeze-drying an aqueous solution or suspension comprising a pharmaceutical agent, said solution or suspension having a solids content of 20% by weight or more.

The invention further provides:

a dosage receptacle for a needleless syringe, said receptacle containing an effective amount of a powder prepared by the process of the invention;

a needleless syringe which is loaded with a powder prepared by the process of the invention;

a vaccine composition comprising a pharmaceutically acceptable carrier or diluent and a powder prepared by the process of the invention;

a method of vaccinating a subject, which method comprises administering to the said subject an effective amount of a powder prepared by the process of the invention; and a powder which is prepared by the process of the invention.

BRIEF DESCRIPTION OF THE DRAWINGS

FIG. 1a shows particles from Formulation 138-20-4A, prepared by spray freeze-drying (SFD) 20 µg of the HBsAg antigen. FIG. 1b shows particles from Formulation 138-16-1C, prepared by SFD and then sieving to obtain a 38–53 µm particle fraction formed from 20 µg of HBsAg antigen and 50 µg of alum adjuvant. FIG. 1c shows particles from Formulation 138-20-4B, prepared by SFD and then compressing, grinding and sieving (C/G/S) to obtain a 38–53 µm particle fraction formed from 20 µg of HBsAg antigen. FIG. 1d shows particles from Formulation 138-20-5C, prepared by SFD and then C/G/S to obtain a 38-53 µm particle fraction formed from 20 µg of HBsAg antigen and 50 µg of alum adjuvant.

FIG. 2a shows particles from Formulation 138-20-4A, prepared by SFD 20 µg of the HBsAg antigen. FIG. 2b shows particles from Formulation 138-16-1C, prepared by SFD and then sieving to obtain a 38–53 µm particle fraction formed from 20 µg of HBsAg antigen and 50 µg of alum adjuvant. FIG. 2c shows particles from Formulation 138-20-4B, prepared by SFD and then C/G/S to obtain a 38–53 µm particle fraction formed from 20 µg of HBsAg antigen. FIG. 2d shows particles from Formulation 138-20-5C, prepared by SFD and then C/G/S to obtain a 38-53 µm particle fraction formed from 20 µg of HBsAg antigen and 50 µg of alum adjuvant.

FIG. 3a is an optical image of the reconstituted formulation 138-16-1 prepared by SFD 20 µg of the HBsAg antigen. FIG. 3b is an optical image of the reconstituted formulation 138-20-5C prepared by SFD and then C/G/S to obtain a 38–53 µm particle fraction formed from 20 µg of HBsAg antigen and 50 µg of alum adjuvant.

Figure 5:
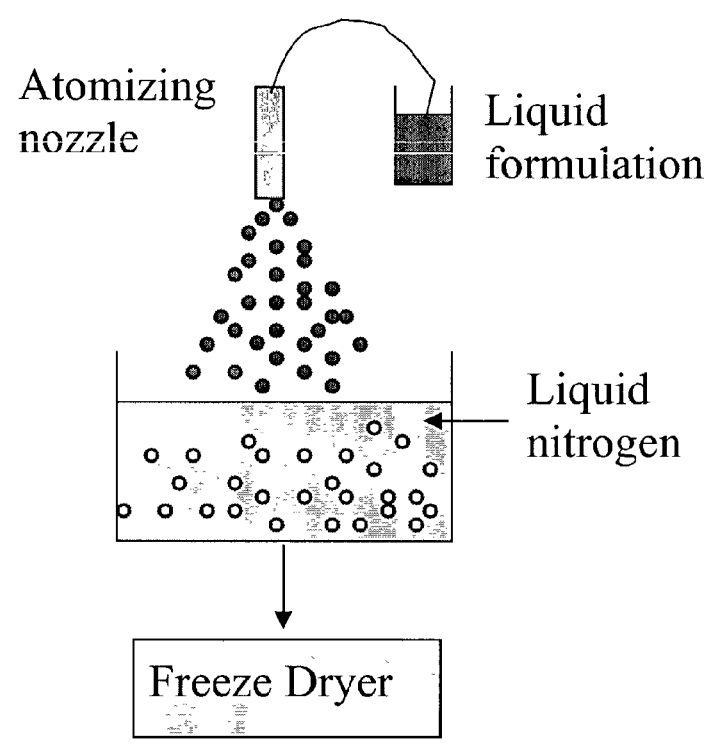

FIG. 5 is a schematic of the Spray Freeze-Drying (SFD) process described in Example 2 at subpart 2.3.1.

FIG. 6a shows particles from Formulation 156-16-1 prepared by SFD a composition containing 10% BSA, 45% trehalose, 27% mannitol, 18% PVP (K17) and 0.1% Pluronic F68. FIG. 6b shows particles from Formulation 156-16-2 prepared by SFD a composition containing 10% BSA, 44.9% trehalose, 26.9% mannitol, 18% PVP (K17), 0.1% methionine, and 0.1% Pluronic F68. FIG. 6c shows particles from Formulation 156-16-3 prepared by SFD a composition containing 10% BSA, 26.9% trehalose, 26.9% mannitol, 35.9% PVP (K17), 0.1% methionine, and 0.1% Pluronic F68. FIG. 6e shows particles from Formulation 156-16-4 prepared by SFD a composition containing 10% BSA, 26.9% trehalose, 26.9% mannitol, 35.9% PVP (K17), 0.1% methionine, and 0.1% Pluronic F68.

FIG. 7a shows particles from Formulation 156-35-1 prepared by SFD a composition containing 10% BSA, 36% raffinose, 27% trehalose, and 27% mannitol. FIG. 7b shows particles from Formulation 156-35-2 prepared by SFD a composition containing 10% BSA, 36% raffinose, 36% mannitol, and 18% PVP (K17). FIG. 7c shows particles from Formulation 156-35-3 prepared by SFD a composition containing 10% BSA, 40% raffinose and 30% mannitol. FIG. 7d shows particles from Formulation 156-42-1 prepared by SFD a composition containing 10% BSA, 36% raffinose, 27% trehalose, and 27% mannitol. FIG. 7e shows particles from Formulation 156-42-2 prepared by SFD a composition containing 10% BSA, 27% raffinose, 27% mannitol, 18% glycine and 18% trehalose. FIG. 7f shows particles from Formulation 156-42-4 prepared by SFD a composition containing 10% BSA, 27% raffinose, 27% sucrose, and 36% mannitol FIG. 8a shows particles from Formulation 156-35-4 prepared by SFD a composition containing 10% BSA, 27% trehalose, 27% mannitol and 36% dextran (10 kDa). FIG. 8b shows particles from Formulation 156-42-3-1 prepared by SFD a composition containing 10% BSA, 27% trehalose, 27% mannitol and 36% dextran (10 kDa). FIG. 8c shows particles from Formulation 156-42-3-2 prepared by SFD a composition containing 10% BSA, 27% trehalose, 27% mannitol and 36% dextran (10 kDa). FIG. 8d shows particles from Formulation 156-53-1 prepared by SFD a composition containing 10% BSA, 27% trehalose, 27% mannitol and 36% dextran (10 kDa). FIG. 8e shows particles from Formulation 156-61-1 prepared by SFD a composition containing 10% BSA, 27% trehalose, 27% mannitol and 36% dextran (10 kDa). FIG. 8f shows particles from Formulation 156-65-1 prepared by SFD a composition containing 10% BSA, 36% trehalose, 18% mannitol, 18% arginine glutamate, and 18% dextran (10 kDa).

FIG. 9a shows particles from Formulation 156-57-1 prepared by SFD a composition containing 10% BSA, 36% trehalose, 36% mannitol, and 18% alanine. FIG. 9b shows particles from Formulation 156-57-2 prepared by SFD a composition containing 10% BSA, 27% trehalose, 27% mannitol, and 36% arginine glutamate. FIG. 9c shows particles from Formulation 156-65-2 prepared by SFD a composition containing 10% BSA, 36% trehalose, 18% mannitol, and 36% arganine glutamate. FIG. 9d shows particles from Formulation 156-71-1 prepared by SFD a composition containing 10% BSA, 36% trehalose, 18% mannitol, and 36% arganine glutamate. FIG. 9e shows particles from Formulation 156-76-1 prepared by SFD a composition containing 10% BSA, 35.9% trehalose, 18% mannitol, 35.9% arginine glutamate, 0.1% Pluronic F168, and 0.1% methionine. FIG. 9f shows particles from Formulation 156-76-2 prepared by SFD a composition containing 10% BSA, 26.9% trehalose, 26.9% mannitol, 35.9% arginine glutamate, 0.1% Pluronic F168, and 0.1% methionine.

FIG. 10a shows particles from Formulation 156-80-1 prepared by SFD a composition containing 10% BSA, 27% trehalose, 27% mannitol, and 36% arginine aspartate. FIG. 10b shows particles from Formulation 156-80-2 prepared by SFD a composition containing 10% BSA, 5% Pluronic F168, 59.5% trehalose, and 25.5% mannitol. FIG. 10c shows particles from Formulation 156-80-3 prepared by SFD a composition containing 10% BSA, 35.9% trehalose, 18% mannitol, 35.9% arginine glutamate, 0.1% methionine and 0.1% Tween 80.

FIG. 11a shows the Adju-Phos adjuvant (2 w/v % placebo AlPO$_4$) gel after freezing at −20° C. and thawing under ambient conditions. FIG. 11b shows the Adju-Phos gel after spray-freezing and then thawing. FIG. 11c shows the Alhydrogel adjuvant (2 w/v % placebo Al(OH)$_3$) gel after freezing at −20° C. and thawing at ambient conditions. FIG. 11d shows the Alhydrogel gel after spray-freezing and then thawing.

FIGS. 12a and 12b depict the particle size analysis described in Example 3, subpart 3.5.1. FIG. 12a shows the particle size analyses by AccuSizer for: (a) a starting alum-adsorbed HBsAg gel, depicted by the (♦) curve on the graph; (b) a "high Alum SFD" composition formed from Alum hydroxide (3.0 w/v %), mannitol (1.9 w/v %), glycine (0.5 w/v %), and dextran (0.61 w/v %), depicted by the (◇) curve on the graph; and (c) a "low Alum SFD" composition formed from Alum hydroxide (0.6 w/v %), mannitol (2.8 w/v %), glycine (1.2 w/v %), and dextran (0.58 w/v %), depicted by the (*) curve on the graph. FIG. 12b shows the particle size analyses by AccuSizer for: (a) a starting alum-adsorbed HBsAg gel, depicted by the (♦) curve on the graph; and a freeze dried, C/G/S processed composition formed from Alum hydroxide (3.0 w/v %), mannitol (1.9 w/v %), glycine (0.5 w/v %), and dextran (0.61 w/v %), depicted by the (*) curve on the graph.

FIGS. 15a–15e are digital light microscope images of H&E stained sections from the histological skin samples taken in the study described in Example 4, subpart 4.4.1, and showing histological changes in the immunization sites. FIG. 15a shows normal skin (20X); FIG. 15b shows the site of EPI administration (24X); FIG. 15c shows the site of EPI administration (105X); FIG. 15d shows the site of intradermal (ID) injection (20X) and FIG. 15e shows the site of ID injection (105X).

FIGS. 16a and 16b are scanning electron micrographs (SEMs) of SFD alum powder formulations described in Example 4 at subpart 4.5.1. The formulations were formed from compositions containing trehalose (30%), mannitol (30%), dextran (40%) at 35 w/w % of total solid content. FIG. 16a shows an aluminium hydroxide composition, and FIG. 16b shows an aluminium phosphate composition.

FIGS. 17a–17d are optical micrographs assessing alum coagulation in selected particle formulations as described in Example 4 at subpart 4.4.1. FIG. 17a shows a reconstituted freeze dried (FD) alum hydroxide composition formulated with trehalose (30%), mannitol (30%), dextran (40%) at 35 w/w % of total solid content. FIG. 17b shows a reconstituted SFD alum hydroxide composition formulated with trehalose (30%), mannitol (30%), dextran (40%) at 35 w/w % of total solid content. FIG. 17c shows a reconstituted FD alum phosphate composition formulated with trehalose (30%), mannitol (30%), dextran (40%) at 35 w/w % of total solid content. FIG. 17d shows a reconstituted SFD alum phosphate composition formulated with trehalose (30%), mannitol (30%), dextran (40%) at 35 w/w % of total solid content FIGS. 18a–18b are optical micrographs assessing alum coagulation in selected particle formulations as described in Example 4 at subpart 4.4.3. FIG. 18a shows a reconstituted SFD alum phosphate composition formulated with trehalose (30%), mannitol (30%), dextran (40%) and polysorbate 80 at 0.5 w/w % of total solid content, where the starting total solid content was 35 w/w %. FIG. 18b shows a reconstituted SFD alum phosphate composition formulated with trehalose (30%), mannitol (30%), dextran (40%) and polysorbate 80 at 0.5 w/w % of total solid content, where the starting total solid content was 40 w/w %. FIG. 18c shows a reconstituted SFD alum phosphate composition formulated with trehalose (30%), mannitol (30%), dextran (40%) and polysorbate 80 at 0.5 w/w % of total solid content, where the starting total solid content was 30 w/w %. FIG. 18d shows a reconstituted SFD alum phosphate composition formulated with trehalose (30%), mannitol (30%), dextran (40%) and polysorbate 80 at 0.5 w/w % of total solid content, where the starting total solid content was 25 w/w %.

FIGS. 19a and 19b show the ELISA results obtained in Example 4, subpart 4.6.1, reported as geometric mean anti-HBsAg IgG antibody titers of animals vaccinated with HBsAg vaccine compositions. FIG. 19a shows titers from animals receiving SFD compositions delivered by EPI ("SFD/EPI"), where the compositions were either a SFD formulation containing 1 µg HBsAg adsorbed to 25 µg aluminium hydroxide ("Al(OH)$_3$") or a SFD formulation containing 1 µg HBsAg adsorbed to 25 µg aluminium phosphate ("AlPO$_4$"); animals receiving SFD compositions that were reconstituted to liquid form and delivered via IM injection ("SFD/reconstituted/IM"), where the compositions were either a SFD formulation containing 1 µg HBsAg adsorbed to 25 µg aluminium hydroxide ("Al(OH)$_3$") or a SFD formulation containing 1 µg HBsAg adsorbed to 25 µg aluminium phosphate ("AlPO$_4$"); or a control receiving the commercial Hepatitis B vaccine composition containing 1 µg HBsAg adsorbed to 25 µg Al(OH)$_3$. Titers are reported from week 4, 6 and 9 sera. FIG. 19b shows titers from animals receiving either a reconstituted SFD vaccine formulation containing 2 µg HBsAg adsorbed with 2.5 µg AlPO$_4$ ("SFD/reconstituted"); or a liquid injection of a conventional IM formulation containing 2 µg HBsAg adsorbed to 50 µg AlPO$_4$ ("liquid/commercial"). Titers are reported from weeks 4 and 6 sera.

DETAILED DESCRIPTION OF THE PREFERRED EMBODIMENTS

Figure 1A:
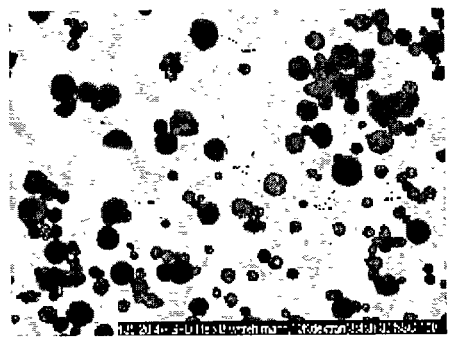
FIGS. 1a–1d are optical micrographs (at ×100 magnification) of selected particle formulations assessed in the study described in Example 1 at subpart 1.5.2.
Figure 1B:
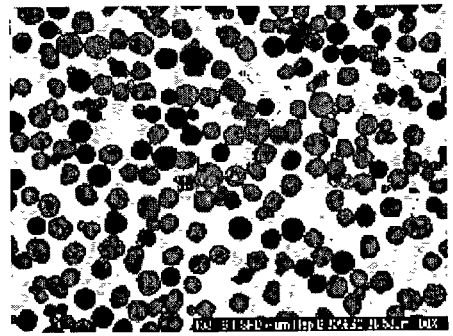
Figure 1C:
Figure 1D:
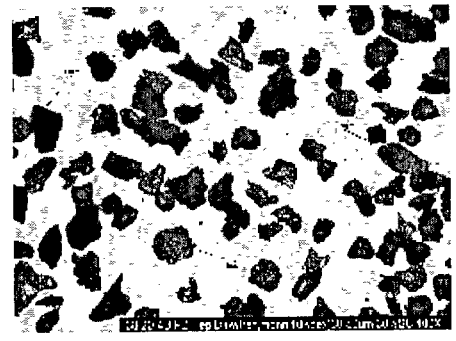
Figure 2A:
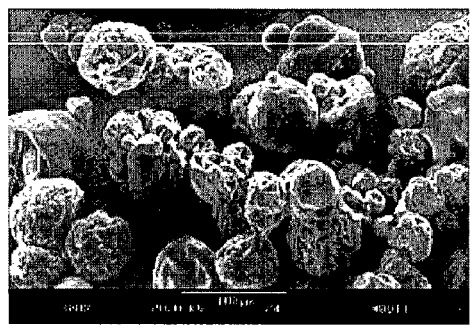
FIGS. 2a–2d are SEM micrographs of selected particle formulations assessed in the study described in Example 1 at subpart 1.5.3.
Figure 2B:
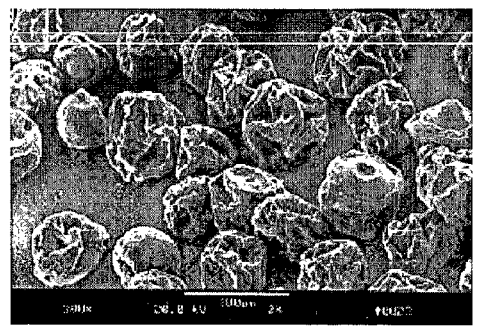
Figure 2C:
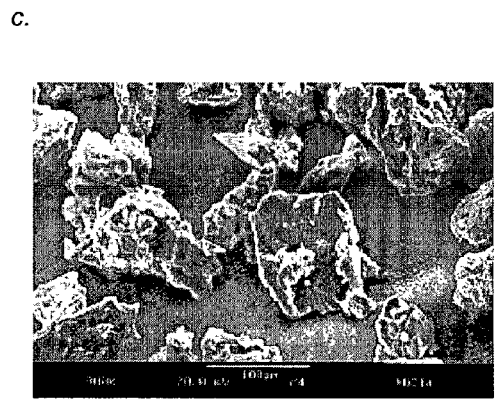
Figure 2D:
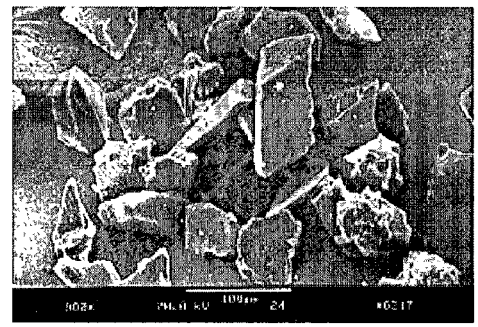

Before describing the present invention in detail, it is to be understood that this invention is not limited to particularly exemplified compositions or process parameters. It is also to be understood that the terminology used herein is for the purpose of describing particular embodiments of the invention only, and is not intended to be limiting.

All publications, patents and patent applications cited herein, whether supra or infra, are hereby incorporated by reference in their entirety.

It must be noted that, as used in this specification and the appended claims, the singular forms "a," "an" and "the" include plural referents unless the content clearly dictates otherwise. Thus, for example, reference to "a particle" includes a mixture of two or more such particles, reference to "an excipient" includes mixtures of two or more such excipients, and the like.

A. Definitions

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

In describing the present invention, the following terms will be employed, and are intended to be defined as indicated below.

As used herein, the term "pharmaceutical" or "pharmaceutical agent" intends any compound or composition of matter which, when administered to an organism (human or animal) induces a desired pharmacologic and/or physiologic effect by local and/or systemic action. The term therefore encompasses those compounds or chemicals traditionally regarded as drugs, as well as biopharmaceuticals including molecules such as peptides, hormones, nucleic acids, gene constructs and the like. More particularly, the term "pharmaceutical" or "pharmaceutical agent" includes compounds or compositions for use in all of the major therapeutic areas including, but not limited to, anti-infectives such as antibiotics and antiviral agents; analgesics and analgesic combinations; local and general anaesthetics; anorexics; antiarthritics; antiasthmatic agents; anticonvulsants; antidepressants; antihistamines; anti-inflammatory agents; antinauseants; antineoplastics; antipruritics; antipsychotics; antipyretics; antispasmodics; cardiovascular preparations (including calcium channel blockers, ACE-inhibitors, beta-blockers, beta-agonists and antiarrythmics); antihypertensives; diuretics; vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; therapeutic proteins (e.g., antigens, antibodies, growth factors, cytokines, interleukins, lymphokines, interferons, enzymes, etc.), peptides and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like).

By "antigen" is meant a molecule which contains one or more epitopes that will stimulate a host's immune system to make a cellular antigen-specific immune response or a humoral antibody response. Thus, antigens include polypeptides including antigenic protein fragments, oligosaccharides, polysaccharides and the like. Furthermore, the antigen can be derived from any known virus, bacterium, parasite, plant, protozoan or fungus, and can be a whole organism.

The term also includes tumor antigens. Similarly, an oligonucleotide or polynucleotide which expresses an antigen, such as in DNA immunization applications, is also included in the definition of an antigen. Synthetic antigens are also included, for example polyepitopes, flanking epitopes and other recombinant or synthetically derived antigens (Bergmann et al (1993) *Eur. J. Immunol.* 23:2777–2781; Bergmann et al. (1996) *J. Immunol.* 157:3242–3249; Suhrbier, A. (1997) *Immunol. and Cell Biol.* 75:402–408; Gardner et al. (1998) 12th World AIDS Conference, Geneva, Switzerland, Jun. 28–Jul. 3, 1998).

The above pharmaceuticals or pharmaceutical agents, alone or in combination with other agents, are typically prepared as pharmaceutical compositions which can contain one or more added materials such as carriers, vehicles, and/or excipients. "Carriers," "vehicles" and "excipients" generally refer to substantially inert materials which are nontoxic and do not interact with other components of the composition in a deleterious manner. These materials can be used to increase the amount of solids in particulate pharmaceutical compositions. Examples of suitable carriers include water, silicone, gelatin, waxes, and like materials. Examples of normally employed "excipients," include pharmaceutical grades of carbohydrates including monosaccharides, disaccharides, cyclodextrans, and polysaccharides (e.g., dextrose, sucrose, lactose, trehalose, raffinose, mannitol, sorbitol, inositol, dextrans, and maltodextrans); starch; cellulose; salts (e.g. sodium or calcium phosphates, calcium sulfate, magnesium sulfate); citric acid; tartaric acid; glycine; high molecular weight polyethylene glycols (PEG); polyvinylpyrrolidone (PVP); Pluronics; surfactants; and combinations thereof. Generally, when carriers and/or excipients are used, they are used in amounts ranging from about 0.1 to 99 wt % of the pharmaceutical composition.

The term "powder" as used herein refers to a composition that consists of substantially solid particles that can be delivered transdermally using a needleless syringe device. The particles that make up the powder can be characterized on the basis of a number of parameters including, but not limited to, average particle size, average particle density, particle morphology (e.g. particle aerodynamic shape and particle surface characteristics) and particle penetration energy (P.E.).

The average particle size of the powders according to the present invention can vary widely and is generally from 0.1 to 250 µm, for example from 10 to 100 µm and more typically from 20 to 70 µm. The average particle size of the powder can be measured as a mass mean aerodynamic diameter (MMAD) using conventional techniques such as microscopic techniques (where particles are sized directly and individually rather than grouped statistically), absorption of gases, permeability or time of flight. If desired, automatic particle-size counters can be used (e.g. Aerosizer Counter, Coulter Counter, HIAC. Counter, or Gelman Automatic Particle Counter) to ascertain the average particle size.

Actual particle density or "absolute density" can be readily ascertained using known quantification techniques such as helium pycnometry and the like. Alternatively, envelope ("tap") density measurements can be used to assess the density of a powder according to the invention. The envelope density of a powder of the invention is generally from 0.5 to 25 g/cm$^3$, preferably from 0.8 to 1.5 g/cm$^3$.

Envelope density information is particularly useful in characterizing the density of objects of irregular size and shape. Envelope density is the mass of an object divided by its volume, where the volume includes that of its pores and small cavities but excludes interstitial space. A number of methods of determining envelope density are known in the art, including wax immersion, mercury displacement, water absorption and apparent specific gravity techniques. A number of suitable devices are also available for determining envelope density, for example, the GeoPyc™ Model 1360, available from the Micromeritics Instrument Corp. The difference between the absolute density and envelope density of a sample pharmaceutical composition provides information about the sample's percentage total porosity and specific pore volume.

Particle morphology, particularly the aerodynamic shape of a particle, can be readily assessed using standard light microscopy. It is preferred that the particles which make up the instant powders have a substantially spherical or at least substantially elliptical aerodynamic shape. It is also preferred that the particles have an axis ratio of 3 or less to avoid the presence of rod- or needle-shaped particles. These same microscopic techniques can also be used to assess the particle surface characteristics, e.g. the amount and extent of surface voids or degree of porosity.

Particle penetration energies can be ascertained using a number of conventional techniques, for example a metallized film P.E. test. A metallized film material (e.g. a 125 µm polyester film having a 350 Å layer of aluminum deposited on a single side) is used as a substrate into which the powder is fired from a needleless syringe (e.g. the needleless syringe described in U.S. Pat. No. 5,630,796 to Bellhouse et al) at an initial velocity of about 100 to 3000 m/sec. The metallized film is placed, with the metal-coated side facing upwards, on a suitable surface.

A needleless syringe loaded with a powder is placed with its spacer contacting the film, and then fired. Residual powder is removed from the metallized film surface using a suitable solvent. Penetration energy is then assessed using a BioRad Model GS-700 imaging densitometer to scan the metallized film, and a personal computer with a SCSI interface and loaded with MultiAnalyst software (BioRad) and Matlab software (Release 5.1, The MathWorks, Inc.) is used to assess the densitometer reading. A program is used to process the densitometer scans made using either the transmittance or reflectance method of the densitometer. The penetration energy of the spray freeze-dried powders should be equivalent to, or better than that of reprocessed mannitol particles of the same size (mannitol particles that are freeze-dried, compressed, ground and sieved according to the methods of commonly owned International Publication No. WO 97/48485, incorporated herein by reference).

The terms "nucleic acid molecule" and "polynucleotide" are used interchangeably herein and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term nucleic acid sequence is the alphabetical representation of a polynucleotide molecule. This alphabetical representation can be input into databases in a computer having a central processing unit and used for bioinformatics applications such as functional genomics and homology searching.

A "vector" is capable of transferring nucleic acid sequences to target cells (e.g., viral vectors, non-viral vectors, particulate carriers, and liposomes). Typically, "vector construct", "expression vector", and "gene transfer vector", mean any nucleic acid construct capable of directing the expression of a gene of interest and which can transfer gene sequences to target cells. Thus, the term includes cloning and expression vehicles, as well as viral vectors. A "plasmid" is a vector in the form of an extrachromosomal genetic element.

A nucleic acid sequence which "encodes" a selected antigen is a nucleic acid molecule which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. For the purposes of the invention, such nucleic acid sequences can include, but are not limited to, cDNA from viral, procaryotic or eucaryotic mRNA, genomic sequences from viral or procaryotic DNA or RNA, and even synthetic DNA sequences. A transcription termination sequence may be located 3' to the coding sequence.

A "promoter" is a nucleotide sequence which initiates and regulates transcription of a polypeptide-encoding polynucleotide. Promoters can include inducible promoters (where expression of a polynucleotide sequence operably linked to the promoter is induced by an analyte, cofactor, regulatory protein, etc.), repressible promoters (where expression of a polynucleotide sequence operably linked to the promoter is repressed by an analyte, cofactor, regulatory protein, etc.), and constitutive promoters. It is intended that the term "promoter" or "control element" includes full-length promoter regions and functional (e.g., controls transcription or translation) segments of these regions.

"Operably linked" refers to an arrangement of elements wherein the components so described are configured so as to perform their usual function. Thus, a given promoter operably linked to a nucleic acid sequence is capable of effecting the expression of that sequence when the proper enzymes are present. The promoter need not be contiguous with the sequence, so long as it functions to direct the expression thereof. Thus, for example, intervening untranslated yet transcribed sequences can be present between the promoter sequence and the nucleic acid sequence and the promoter sequence can still be considered "operably linked" to the coding sequence.

The term "nucleic acid immunization" is used herein to refer to the introduction of a nucleic acid molecule encoding one or more selected antigens into a host cell for the in vivo expression of the antigen or antigens. The nucleic acid molecule can be introduced directly into the recipient subject by transdermal particle delivery. The molecule alternatively can be introduced ex vivo into cells which have been removed from a subject. In this latter case, cells containing the nucleic acid molecule of interest are re-introduced into the subject such that an immune response can be mounted against the antigen encoded by the nucleic acid molecule. The nucleic acid molecules used in such immunization are generally referred to herein as "nucleic acid vaccines."

The term "solids content" indicates the amount of solids which are either dissolved or suspended in the solvent(s) used.

The term "subject" refers to any member of the subphylum cordata including, without limitation, humans and other primates including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered. The methods described herein are intended for use in any of the above vertebrate species, since the immune systems of all of these vertebrates operate similarly.

The term "transdermal delivery" includes both transdermal ("percutaneous") and transmucosal routes of administration, i.e. delivery by passage through the skin or mucosal tissue. See, e.g., *Transdermal Drug Delivery: Developmental Issues and Research Initiatives*, Hadgraft and Guy (eds.), Marcel Dekker, Inc., (1989); *Controlled Drug Delivery: Fundamentals and Applications*, Robinson and Lee (eds.), Marcel Dekker Inc., (1987); and *Transdermal Delivery of Drugs*, Vols. 1–3, Kydonieus and Berner (eds.), CRC Press, (1987).

B. General Methods

The invention is concerned with processes for producing powders suitable for transdermal delivery via needleless syringe. As such, the particles which make up the powdered composition must have sufficient physical strength to withstand sudden acceleration to several times the speed of sound and the impact with, and passage through, the skin and tissue.

In order to achieve powders having these properties, the process of the present invention is carried out using a solution or suspension containing the desired pharmaceutical agent and having a total solids content of 20% by weight or more in the solvent system. Preferably the solids content in the solvent system is 25% by weight or more, more preferably 28% or 30% by weight or more and particularly preferably 40% by weight or more. The use of a solution or suspension having a solids content of 20% by weight or more minimises pore formation during the drying process and increases the density of the particles formed. This increased density is important in ensuring that the particles are sufficiently robust to survive the harsh conditions of transdermal delivery via needleless syringe. The solids content of the solution or dispersion may be up to 50% by weight, up to 60% by weight or even up to 70% by weight. The upper limit depends upon, for example, the particular components of the solution or dispersion and the desired characteristics of the resulting spray freeze-dried particles.

The pharmaceutical agent used to produce the powders of the invention may be any small molecule drug substance, organic or inorganic chemical, vaccine, or peptide (polypeptide and/or protein) of interest. In particular embodiments, the pharmaceutical agent is a biopharmaceutical preparation of a peptide, polypeptide, protein or any other such biological molecule. Exemplary peptide and protein formulations include, without limitation, insulin; calcitonin; octreotide; endorphin; liprecin; pituitary hormones (e.g., human growth hormone and recombinant human growth hormone (hGH and rhGH), HMG, desmopressin acetate, etc); follicle luteoids; growth factors (such as growth hormone releasing factor (GHRF), somatostatin, somatotropin and platelet-derived growth factor); asparaginase; chorionic gonadotropin; corticotropin (ACTH); erythropoietin (EPO); epoprostenol (platelet aggregation inhibitor); glucagon; interferons; interleukins; menotropins (urofollitropin, which contains follicle-stimulating hormone (FSH); and luteinizing hormone (LH)); oxytocin; streptokinase; tissue plasminogen activator (TPA); urokinase; vasopressin; desmopressin; ACTH analogues; angiotensin II antagonists; antidiuretic hormone agonists; bradykinin antagonists; CD4 molecules; antibody molecules and antibody fragments (e.g., Fab, Fab$_2$, Fv and sFv molecules); IGF-1; neurotrophic factors; colony stimulating factors; parathyroid hormone and agonists; parathyroid hormone antagonists; prostaglandin antagonists; protein C; protein S; renin inhibitors; thrombolytics; tumor necrosis factor (TNF); vaccines (particularly peptide vaccines including subunit and synthetic peptide preparations); vasopressin antagonists analogues; and α-1 antitrypsin. Additionally, nucleic acid preparations, such as vectors or gene constructs for use in subsequent gene delivery, can be used.

Particularly suitable pharmaceutical agents for use herein are antigens. Any suitable antigen as defined herein may be employed. The antigen may be a viral antigen. The antigen may therefore be derived from members of the families Picornaviridae (e.g. polioviruses, etc.); Caliciviridae; Togaviridae (e.g. rubella virus, dengue virus, etc.); Flaviviridae; Coronaviridae; Reoviridae; Birnaviridae; Rhabodoviridae (e.g. rabies virus, etc.); Filoviridae; Paramyxoviridae (e.g. mumps virus, measles virus, respiratory syncytial virus, etc.); Orthomyxoviridae (e.g. influenza virus types A, B and C, etc.); Bunyaviridae; Arenaviridae; Retroviradae (e.g. HTLV-I; HTLV-II; HIV-1 and HIV-2); and simian immunodeficiency virus (SIV) among others.

Alternatively, viral antigens may be derived from a papillomavirus (e.g. HPV); a herpesvirus; a hepatitis virus, e.g. hepatitis A virus (HAV), hepatitis B virus (HBV), hepatitis C (HCV), the delta hepatitis virus (HDV), hepatitis E virus (HEV) or hepatitis G virus (HGV); and the tick-borne encephalitis viruses. See, e.g. *Virology*, 3rd Edition (W. K. Joklik ed. 1988); *Fundamental Virology*, 2nd Edition (B. N. Fields and D. M. Knipe, eds. 1991) for a description of these viruses.

Bacterial antigens for use in the invention can be derived from organisms that cause diphtheria, cholera, tuberculosis, tetanus, pertussis, meningitis and other pathogenic states, including Meningococcus A, B and C, *Hemophilus influenza* type B (HIB) and *Helicobacter pylori*. A combination of bacterial antigens may be provided, for example diphtheria, pertussis and tetanus antigens. Suitable pertussis antigens are pertussis toxin and/or filamentous haemagglutinin and/or pertactin, alternatively termed P69. An anti-parasitic antigen may be derived from organisms causing malaria and Lyme disease.

Antigens for use in the present invention can be produced using a variety of methods known to those of skill in the art. In particular, the antigens can be isolated directly from native sources, using standard purification techniques. Alternatively, whole killed, attenuated or inactivated bacteria, viruses, parasites or other microbes may be employed. Yet further, antigens can be produced recombinantly using known techniques. See, e.g., Sambrook, Fritsch & Maniatis, *Molecular Cloning: A Laboratory Manual*, Vols. I and II (D. N. Glover et. 1985).

Antigens for use herein may also be synthesised, based on described amino acid sequences, via chemical polymer syntheses such as solid phase peptide synthesis. Such methods are known to those of skill in the art. See, e.g. J. M. Stewart and J. D. Young, *Solid Phase Peptide Synthesis*, 2nd Ed., Pierce Chemical Co., Rockford, Ill. (1984) and G. Barany and R. B. Merrifield, *The Peptides: Analysis, Synthesis, Biology*, editors E. Gross and J. Meienhofer, Vol. 2, Academic Press, New York, (1980), pp. 3–254, for solid phase peptide synthesis techniques; and M. Bodansky, *Principles of Peptide Synthesis*, Springer-Verlag Berlin (1984) and E. Gross and J. Meienhofer, Eds., *The Peptides: Analysis, Synthesis, Biology*, supra, Vol. 1, for classical solution synthesis.

The pharmaceutical agent may alternatively be a nucleic acid molecule. The pharmaceutical agent can thus be a polynucleotide which expresses an antigen, such as in DNA immunization applications. An expression vector can thus be employed in which a nucleic acid sequence encoding a desired polypeptide such as an antigen is operably linked to a promoter.

Typically, the nucleic acid molecule comprises a therapeutically relevant nucleotide sequence for delivery to a subject. Thus, the nucleic acid molecule may comprise one or more genes encoding a protein defective or missing from a target cell genome or one or more genes that encode a non-native protein having a desired biological or therapeutic effect (e.g., an antiviral function). The molecule may comprise a sequence capable of providing immunity, for example an immunogenic sequence that serves to elicit a humoral and/or cellular response in a subject, or a sequence that corresponds to a molecule having an antisense or ribozyme function. For the treatment of genetic disorders, functional genes corresponding to genes known to be deficient in the particular disorder can be administered to a subject.

Suitable nucleic acids for delivery include those used for the treatment of inflammatory diseases, autoimmune, chronic and infectious diseases, including such disorders as AIDS, cancer, neurological diseases, cardivascular disease, hypercholestemia; various blood disorders including various anemias, thalassemia and hemophilia; genetic defects such as cystic fibrosis, Gaucher's Disease, adenosine deaminase (ADA) deficiency, emphysema, etc. A number of antisense oligonucleotides (e.g., short oligonucleotides complementary to sequences around the translational initiation site (AUG codon) of an mRNA that are useful in anitsense therapy for cancer and for viral diseases have been described in the art. See, e.g., Han et al (1991) *Proc. Natl. Acad. Sci* USA 88:4313; Uhlmann et al (1990) Chem. Rev. 90:543, Helene et al (1990) Biochim. *Biophys. Acta.* 1049:99; Agarwal et al (1988) Proc. *Natl. Acad. Sci*. USA 85: 7079; and Heikkila et al (1987) *Nature* 328:445. A number of ribozymes suitable for use herein have also been described. See, e.g., Chec et al (1992) *J. Biol. Chem.* 267: 17479 and U.S. Pat. No. 5,225,347 to Goldberg et al.

For example, in methods for the treatment of solid tumors, genes encoding toxic peptides (i.e., chemotherapeutic agents such as ricin, diptheria toxin and cobra venom factor), tumor suppressor genes such as p53, genes coding for mRNA sequences which are antisense to transforming oncogenes, antineoplastic peptides such as tumor necrosis factor (TNF) and other cytokines, or transdominant negative mutants of transforming oncogenes, can be delivered for expression at or near the tumor site.

Similarly, nucleic acids coding for peptides known to display antiviral and/or antibacterial activity, or stimulate the host's immune system, can also be administered. The nucleic acid may encode one of the various cytokines (or functional fragments thereof), such as the interleukins, interferons, chemokines, chemotaxic factors, and colony stimulating factors. The nucleic acid may encode an antigen for the treatment or prevention of a number of conditions including but not limited to cancer, allergies, toxicity and infection by a pathogen such as, but not limited to, fungus, viruses including Human Papiloma Viruses (HPV), HIV, HSV2/HSV1, influenza virus (types A, B and C), Polio virus, RSV virus, Rhinoviruses, Rotaviruses, Hepaptitis A virus, Norwalk Virus Group, Enteroviruses, Astroviruses, Measles virus, Par Influenza virus, Mumps virus, Varicella-Zoster virus, Cytomegalovirus, Epstein-Barr virus, Adenoviruses, Rubella virus, Human T-cell Lymphoma type I virus (HTLV-I), Hepatitis B virus (HBV), Hepatitis C virus (HCV), Hepatitis D virus, Pox virus, Marburg and Ebola; bacteria including *M. tuberculosis, Chlamydia, N. gonorrhoeae, Shigella, Salmonella, Vibrio Cholera, Treponema pallidua, Pseudomonas, Bordetella pertussis, Brucella, Franciscella tulorensis, Helicobacter pylori, Leptospria interrogaus, Legionella pnumophila, Yersinia pestis, Streptococcus* (types A and B), *Pneumococcus, Meningococcus, Hemophilus influenza* (type b), *Toxoplama gondic, Complybacteriosis, Moraxella catarrhalis, Donovanosis*, and *Actinomycosis*; fungal pathogens including Candidiasis and Aspergillosis; parasitic pathogens including Taenia, Flukes, Roundworms, Amebas, *Giardia* species, *Cryptosporidium, Schitosoma* species, *Pneumocystis carinii, Trichuriasis* species, and *Trichinella* species. The nucleic acid my also be used to provide a suitable immune response against numerous veterinary diseases, such as Foot and Mouth diseases, Coronavirus, *Pasteurella multocida, Helicobacter, Strongylus vulgaris, Actinobacillus pleuropneumonia*, Bovine viral diarrhea virus (BVDV), *Klebsiella pneumoniae, E. Coli, Bordetella pertussis, Bordetella parapertussis* and *brochiseptica*. Thus in one aspect, the particles of the present invention may find use as a vaccine.

The invention will also find use in antisense therapy, e.g., for the delivery of oligonucleotides able to hybridize to specific complementary sequences thereby inhibiting the transcription and/or translation of these sequences. Thus DNA or RNA coding for proteins necessary for the progress of a particular disease can be targeted, thereby disrupting the disease process. Antisense therapy, and numerous oligonucleotides which are capable of binding specifically and predictably to certain nucleic acid target sequences in order to inhibit or modulate the expression of disease-causing genes are known and readily available to the skilled practitioner. Uhlmann et al (1990) *Chem Rev.* 90: 543, Neckers et al (1992) *Int. Rev. Oncogenesis* 3, 175; Simons et al (1992) *Nature* 359, 67; Bayever et al (1992) Antisense *Res. Dev.* 2: 109; Whitesell et al (1991) Antisense Res. Dev. 1: 343; Cook et al (1991) *Anti-cancer Drug Design* 6: 585; Eguchi et al (1991) *Ann. Rev. Biochem.* 60: 631. Accordingly, antisense oligonucleotides capable of selectively binding to target sequences in host cells are provided herein for use in antisense therapeutics.

The antigen or other pharmaceutical agent employed in the present invention may optionally be adsorbed into an adjuvant, such as an aluminum salt adjuvant or calcium salt adjuvant. Alternatively, the antigen or other pharmaceutical agent may be used without an adjuvant. Suitable adjuvants include aluminium hydroxide, aluminum phosphate, aluminum sulfate and calcium phosphate.

The pharmaceutical agent is typically prepared as an aqueous pharmaceutical composition using a suitable aqueous carrier, along with suitable excipients, protectants, solvents, salts, surfactants, buffering agents and the like. Suitable excipients can include any materials that are innocuous when administered to an individual, and do not significantly interact with the pharmaceutical agent in a manner that alters its pharmaceutical activity. Examples of normally employed excipients include, but are not limited to, pharmaceutical grades of dextrose, sucrose, lactose, trehalose, mannitol, sorbitol, inositol, dextran, starch, cellulose, sodium or calcium phosphates, calcium carbonate, calcium sulfate, sodium citrate, citric acid, tartaric acid, glycine, high molecular weight polyethylene glycols (PEG), and combinations thereof. Suitable solvents include, but are not limited to, methylene chloride, acetone, methanol, ethanol, isopropanol and water. Typically, water is used as the solvent. Generally pharmaceutically acceptable salts having molarities ranging from about 1 mM to 2M can be used. Pharmaceutically acceptable salts include, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients, vehicles and auxiliary substances is available in REMINGTON'S PHARMACEUTICAL SCIENCES (Mack Pub. Co., N.J. 1991), incorporated herein by reference.

The excipients chosen for use in the present invention may serve specific functions such as protein stabilization or surface protection or may be used as bulking agents or to maintain low hygroscopicity of the powders. Although the invention is not limited to the use of any specific excipients, particularly suitable excipients include saccharides, which may be amorphous or crystalline saccharides, polymers or amino acids or physiologically acceptable salts thereof. The use of these particular excipient compositions allow the particles to collapse and densify during freezing and therefore provide powders which are particularly suitable for injection via a needleless syringe. The saccharide may be a monosaccharide, disaccharide or higher oligo- or polysaccharide. The excipients may be selected from carbohydrates, sugars and sugar alcohols. Such excipients may be crystalline or amorphous.

Preferably, one, two or three of these additives are present in the solution or suspension in amounts of at least 15% by weight, preferably at least 20% by weight, such as at least 25%, 28% or 30% by weight and more preferably at least 40% by weight. Such additives may be present in amounts of up to 50% by weight, up to 60% by weight or even up to 70% by weight. The upper limit depends upon, for example, the particular additives used and the desired characteristics of the resulting spray freeze-dried particles. Most preferably one or two different excipients are used.

Suitable amorphous saccharides include sugars. The amorphous excipient may thus be selected from dextrose, sucrose, lactose, trehalose, cellobiose, raffinose, isomaltose and other carbohydrates such as cyclodextrins. Such sugars are capable of stabilizing proteins used as pharmaceutical agents during the spray-freeze-drying process and during long-term storage.

Suitable crystalline carbohydrates, sugars and sugar alcohols include mannitol, sorbitol and allitol. The combination of such a crystalline excipient with an amorphous excipient, typically an amorphous sugar, encourages the collapse of particles during freeze-drying and aids the formation of dense particles.

Suitable polymers include polysaccharides such as dextran or maltodextran; starch; cellulose; polyvinylpyrrolidone (PVP), particularly PVP K-17; polyvinyl alcohol (PVA); and polyethylene glycols (PEG), particularly PEG with a molecular weight of 8,000. Dextrans are preferred. Various grades of dextran are available. A suitable dextran may have a molecular weight of greater than about 15,000 such as from about 15,000 to about 45,000, from about 60,000 to about 90,000 or from about 100,000 to about 200,000. The addition of a polymer as an excipient tends to provide powders with improved flowability and may also provide increased protein stability.

Suitable amino acids and physiologically acceptable salts of amino acids include glycine, alanine, glutamine, arginine, lysine and histidine and salts thereof such as alkali or alkaline earth metals salts such as sodium, potassium or magnesium salts or salts with other amino acids such as glutamate or aspartate salts.

The most preferred combinations of excipients for use in the present invention include an amorphous saccharide with a crystalline saccharide and optionally also a polymer and/or an amino acid or a salt thereof. The excipients may comprise an amorphous saccharide which is typically present in an amount of from 10 to 90% by weight, preferably from 50 to 80% and more preferably from 60 to 75% by weight; and a crystalline saccharide which is typically present in an amount of from 10 to 90% by weight, preferably from 20 to 50% and more preferably from 25 to 40% by weight. This combination of excipients is preferably used together with a surfactant which is typically present in an amount of from 1 to 5% by weight. Alternatively, the additives may comprise an amorphous saccharide which is typically present in an amount of from 10 to 80% by weight, preferably from 20 to 50%, more preferably from 25 to 35% by weight; a crystalline saccharide which is typically present in an amount of from 10 to 80% by weight, preferably from 20 to 50%, more preferably from 25 to 35% by weight; and a polymer or an amino acid or salt thereof, each of which is present in an amount of from 10 to 80% by weight, preferably from 30 to 60%, more preferably from 30 to 50% by weight.

The most preferred additive combinations include trehalose/mannitol, typically at a weight ratio of about 70/30; trehalose/mannitol/dextran, typically at a weight ratio of about 30/30/40; trehalose/mannito/PVP at a weight ratio of about 30/30/40; trehalose/mannitol/PEG, typically at a weight ratio of about 30/30/40; or trehalose/mannitol/arginine glutamate, typically at a weight ratio of about 30/30/40. Particularly suitable particles can be prepared from an aqueous solution or dispersion of a pharmaceutical agent which further comprises trehalose, mannitol and dextran in a weight ratio of from about 3:3:4 to about 4:4:3.

The use of these preferred additive combinations in the amounts described above helps to provide particles with a high density. Thus, two major factors of the present invention act towards increasing the density of the particles. The first is the presence of at least 20% by weight of solids in the solution or suspension prior to freeze-drying and the second is the selection of particular excipient compositions.

Whilst the excipient combinations described above are not essential for use in the present invention, they are particularly preferred when the total amount of solids in the solution or suspension is close to 20% by weight, such as less than 40% by weight, in particular less than 30% or less than 25% by weight. When the solution or suspension has a solids content as low as this, the density of the particles, whilst sufficient for the purposes of the invention, can desirably be increased further by use of the above-described excipient compositions. However, if the solids content is above 30% by weight or more preferably above 40% by weight, the particles produced will be sufficiently dense, so that the extra density obtained by using the preferred excipients in the ratios described above is less important.

The particles of the invention may additionally contain other additives such as surfactants. Suitable surfactants for use in the present invention include non-ionic surfactants. The surfactant may be a polysorbate such as Tween 20 and Tween 80, a Pluronics surfactant such as F68 or a Span surfactant. The surfactant can be used in combination with any of the above-named combinations of excipients.

The particles of the invention are formed by first dissolving or suspending the pharmaceutical agent, and any required additives, in water. The aqueous solution or suspension formed must have a total solids content in the water of at least 20% by weight. The aqueous solution or suspension is then spray freeze-dried. Any known technique in the art (for example the methods described by Mumenthaler et al, Int. J. Pharmaceutics (1991) 72, pages 97–110 and Maa et al, Phar. Res. (1999) Vol. 16, page 249) may be used to carry out the spray freeze-drying step.

A typical spray freeze-drying technique involves atomising the aqueous solution or suspension into a liquified gas, which is generally under stirring. The liquified gas can be liquid argon, liquid nitrogen, or any other gas that results in the immediate freezing of the atomised droplets of the aqueous solution or suspension. Preferably the liquified gas is an inert liquified gas such as liquid nitrogen.

The liquified gas containing the frozen droplets of the aqueous solution or suspension is then freeze-dried. It is not contacted with an organic solvent such as methanol, ethanol, ethyl ether, acetone, pentane, methylene chloride, chloroform or ethyl acetate. Drying is not therefore conducted according to the procedures described in U.S. Pat. No. 5,019,400.

Typically, the liquified gas containing the frozen droplets is transferred into a lyophiliser for freeze-drying. The liquified gas containing the frozen droplets is usually poured into a metal tray and introduced into the lyophiliser. The frozen droplets are freeze-dried in the tray. The liquid nitrogen evaporates and the frozen water contained in the droplets is removed by sublimation. The resulting particles are collected. They can be washed as desired.

In more detail, the liquified gas containing frozen droplets of the atomized solution or suspension is held at reduced temperature, for example from about −60° C. to −40° C. Typically, that is followed by two-stage vacuum drying preferably under a pressure of from about 20 to 500 mT (2.666 to 66.65 Pa). The first drying stage is normally performed at a reduced temperature such as from about −50° C. to 0° C., for a period of about 4 to 24 hours. Frozen water is removed by ice sublimation. In the second drying stage, drying is normally performed at a higher temperature such as from about 5 to 30° C. at a lower pressure, preferably less than 100 mT down to about 10 mT, for a period of about 5 to 24 hours. The precise spray freeze-drying conditions used may be selected according to the desired properties of the particles to be produced. Thus, the temperatures, pressures and other conditions may be varied as desired.

Preferably, the nozzle used to atomise the solution or suspension is an ultrasonic nozzle. This has the advantage of being a mild process which generates little stress to the biomolecules which are frequently used as therapeutic agents in the present invention. In addition, use of an ultrasonic nozzle eliminates the need for pressurized gas to assist the liquid feed which, in turn helps increase the yield of the process. The predominant variable for control of droplet size in an ultrasonic nozzle system is the nozzle frequency, although surface tension, viscosity and density of the liquid feed are additional variables that can be manipulated to control droplet size. Thus, for example, smaller particles may be produced by increasing the nozzle frequency and vice versa. When using the ultrasonic nozzle system. am accurate. low-pulse feed pump can be used to delivery the liquid feed, wherein such pumps are particularly well suited when operating at low feed rates (e.g., about 3 to 5 ml per minute) normally associated with laboratory-scale particle production. It has been found that atomization proceeds well at about 1 to 2 Watts above the "critical power" level of the low-pulse pump system. In some drying cycles, it has been found that operation at about 2.9 to 3.1 Watts allows for the most efficient atomization, however the exact operating conditions will also depend upon the liquid characteristics of the feed (viscosity, density, total solids content, surface tension, etc.).

A dual spray freeze-drying process may also be used. This process is particularly useful when the pharmaceutical agent is a protein having a low water solubility. This dual process comprises spray freeze-drying the liquid protein to form a dry powder. This powder is then reconstituted in water to provide a suspension having the desired solid content and spray freeze-dried for a second time.

The spray freeze-dried particular that are obtained according to the invention can be collected, washed and dried. The dried particles can then be sieved to obtained particles of the desired size.

The particles of the invention have a size appropriate for high-velocity transdermal delivery to a subject, typically across the stratum corneum or a transmucosal membrane. The mass mean aerodynamic diameter (MMAD) of the particles is from about 0.1 to 250 μm. The MMAD may be from 5 to 100 μm or from 10 to 100 μm, preferably from 10 to 70 μm or from 20 to 70 μm. Generally, less than 10% by weight of the particles have a diameter which is at least 5 μm more than the MMAD or at least 5 μm less than the MMAD. Preferably, no more than 5% by weight of the particles have a diameter which is greater than the MMAD by 5 μm or more. Also preferably, no more than 5% by weight of the particles have a diameter which is smaller than the MMAD by 5 μm or more. The particle size is controllable by varying the frequency of the ultrasonic nozzle used to atomise the solution or suspension.

The particles typically have an envelope density of from 0.5 to 25 g/cm$^3$, preferably from 0.6 to 1.8 g/cm$^3$. More preferably the envelope density is from 0.7 to 1.5 g/cm$^3$. The attainment of the above minimum envelope density value is particularly preferred, since particles with a lower density tend to perform poorly during penetration of the skin and may not be suitable for use in a transdermal needleless injection system. The particles have a low porosity, wherein typically at least 70%, at least 80%, at least 85% or at least 90% of the particle is nor occupied by pores.

While the shape of the individual particles may vary when viewed under a microscope, the particles are preferably substantially spherical. The average ratio of the major axis: minor axis is typically from 3:1 to 1:1, for example from 2:1 to 1:1.

The individual particles of the powder have a substantially spherical aerodynamic shape with a substantially uniform, nonporous surface. The particles will also have a particle penetration energy suitable for transdermal delivery from a needleless syringe device. The particles should also be free-flowing under a dry environment. For example, the particles should flow freely in a vial upon rotation at a relative humidity of less than 30%. Preferably, the particles are free-flowing under ambient conditions, such as a relative humidity of less than 60%. The moisture content of the particles should preferably be less than 5%, more preferably less than 2%, after freeze-drying, and this level of moisture should be maintained during storage at less than 30% humidity for, for example, at least one month and preferably much longer.

A detailed description of needleless syringe devices useful in this invention is found in the prior art, as discussed herein. These devices are referred to as needleless syringe devices and representative of these devices are the dermal PowderJect® needleless syringe device and the oral PowderJect® needleless syringe device (PowderJect Technologies Limited, Oxford, UK). By using these devices, an effective amount of the powder of the invention is delivered to the subject. An effective amount is that amount needed to deliver a sufficient quantity of the desired antigen to achieve vaccination. This amount will vary with the nature of the antigen and can be readily determined through clinical testing based on known activities of the antigen being delivered. The "*Physicians Desk Reference*" and "*Goodman and Gilman's The Phamacological Basis of Therapeutics*" are useful for the purpose of determining the amount needed.

Needleless syringe devices for delivering particles were first described in commonly owned U.S. Pat. No. 5,630,796 to Bellhouse et al, incorporated herein by reference. Although a number of specific device configurations are now available, such devices are typically provided as a pen-shaped instrument containing, in linear order moving from top to bottom, a gas cylinder, a particle cassette or package, and a supersonic nozzle with an associated silencer element. An appropriate powder (in the present case, a spray freeze-dried powder of the invention) is provided within a suitable container, e.g., a cassette formed by two rupturable polymer membranes that are heat-sealed to a washer-shaped spacer to form a self-contained sealed unit. Membrane materials can be selected to achieve a specific mode of opening and burst pressure that dictate the conditions at which the supersonic flow is initiated. In operation, the device is actuated to release the compressed gas from the cylinder into an expansion chamber within the device. The released gas contacts the particle cassette and, when sufficient pressure is built up, suddenly breaches the cassette membranes sweeping the particles into the supersonic nozzle for subsequent delivery. The nozzle is designed to achieve a specific gas velocity and flow pattern to deliver a quantity of particles to a target surface of predefined area. The silencer is used to attenuate the noise produced by the transient supersonic flow and/or membrane rupture.

A second needleless syringe device for delivering particles is described in commonly owned International Publication No. WO 96/20022. This delivery system also uses the energy of a compressed gas source to accelerate and deliver powdered compositions; however, it is distinguished from the system of U.S. Pat. No. 5,630,796 in its use of a shock wave instead of gas flow to accelerate the particles. More particularly, an instantaneous pressure rise provided by a shock wave generated behind a flexible dome strikes the back of the dome, causing a sudden eversion of the flexible dome in the direction of a target surface. This sudden eversion catapults a powdered composition (which is located on the outside of the dome) at a sufficient velocity, thus momentum, to penetrate target tissue, e.g., oral mucosal tissue. The powdered composition is released at the point of full dome eversion. The dome also serves to completely contain the high-pressure gas flow, which therefore does not come into contact with the tissue. Because the gas is not released during this delivery operation, the system is inherently quiet. This design can be used in other enclosed or otherwise sensitive applications for example, to deliver particles to sites reached by minimally invasive surgery.

In yet a further aspect of the invention, single unit dosages or multidose containers, in which the powder of the invention may be packaged prior to use, can comprise a hermetically sealed container enclosing a suitable amount of the powder that makes up a suitable dose. The powder can be packaged as a sterile formulation, and the hermetically sealed container can thus be designed to preserve sterility of the formulation until use. If desired, the containers can be adapted for direct use in the above-referenced needleless syringe systems.

Powders of the present invention can thus be packaged in individual unit dosages for delivery via a needleless syringe. As used herein, a "unit dosage" intends a dosage receptacle containing a therapeutically effective amount of a powder of the invention. The dosage receptacle typically fits within a needleless syringe device to allow for transdermal delivery from the device. Such receptacles can be capsules, foil pouches, sachets, cassettes or the like.

The container in which the powder is packaged can further be labeled to identify the composition and provide relevant dosage information. In addition, the container can be labeled with a notice in the form prescribed by a governmental agency, for example the U.S. Food and Drug Administration, wherein the notice indicates approval by the agency under U.S. Federal Law of the manufacture, use or sale of the powder contained therein for human administration.

The actual distance which the delivered particles will penetrate a target surface depends upon particle size (e.g., the nominal particle diameter assuming a roughly spherical particle geometry), particle density, the initial velocity at which the particle impacts the surface, and the density and kinematic viscosity of the targeted skin tissue. In this regard, optimal particle densities for use in needleless injection generally range between about 0.5 and 25 $g/cm^3$, preferably between about 0.7 and 1.5 $g/cm^3$, and injection velocities generally range between about 100 and 3,000 m/sec. With appropriate gas pressure, particles having an average diameter of 10–70 µm can be accelerated through the nozzle at velocities approaching the supersonic speeds of a driving gas flow.

If desired, the needleless syringe systems can be provided in a preloaded condition containing a suitable dosage of the powder of the invention. The loaded syringe can be packaged in a hermetically sealed container, which may further be labeled as described above.

A number of novel test methods have been developed, or established test methods modified, in order to characterize performance of a needleless syringe device. These tests range from characterization of the powdered composition, assessment of the gas flow and particle acceleration, impact on artificial or biological targets, and measures of complete system performance. One, several or all of the following tests can thus be employed to assess the physical and functional suitability of the powder of the invention for use in a needleless syringe system.

Assessment of Effect on Artificial Film Targets

A functional test that measures many aspects of powder injection systems simultaneously has been designated as the "metallized film" or "penetration energy" (PE) test. It is based upon the quantitative assessment of the damage that particles can do to a precision thin metal layer supported by a plastic film substrate. Damage correlates to the kinetic energy and certain other characteristics of the particles. The higher the response from the test (i.e., the higher the film damage/disruption) the more energy the device has imparted to the particles. Either electrical resistance change measurement or imaging densitometry, in reflectance or transmission mode, provide a reliable method to assess device or formulation performance in a controllable and reproducible test.

The film test-bed has been shown to be sensitive to particle delivery variations of all major device parameters including pressure, dose, particle size distribution and material, etc. and to be insensitive to the gas. Aluminum of about 350 Angstrom thickness on a 125 µm polyester support is currently used to test devices operated at up to 60 bar helium pressure.

Assessment of Impact Effect on Engineering Foam Targets

Another means of assessing particle performance when delivered via a needleless syringe device is to gauge the effect of impact on a rigid polymethylimide foam (Rohacell 5 IIG, density 52 $kg/m^3$, Rohm Tech Inc., Malden, Mass.). The experimental set-up for this test is similar to that used in the metallized film test. The depth of penetration is measured using precision calipers. For each experiment a processed mannitol standard is run as comparison and all other parameters such as device pressure, particle size range, etc., are held constant. Data also show this method to be sensitive to differences in particle size and pressure. Processed mannitol standard as an excipient for drugs has been proven to deliver systemic concentrations in preclinical experiments, so the relative performance measure in the foam penetration test has a practical in vivo foundation. Promising powders can be expected to show equivalent or better penetration to mannitol for anticipation of adequate performance in preclinical or clinical studies. This simple, rapid test has value as a relative method of evaluation of powders and is not intended to be considered in isolation.

Particle Attrition Test

A further indicator of particle performance is to test the ability of various candidate compositions to withstand the forces associated with high-velocity particle injection techniques, that is, the forces from contacting particles at rest with a sudden, high velocity gas flow, the forces resulting from particle-to-particle impact as the powder travels through the needleless syringe, and the forces resulting from particle-to-device collisions also as the powder travels through the device. Accordingly, a simple particle attrition test has been devised which measures the change in particle size distribution between the initial composition, and the composition after having been delivered from a needleless syringe device.

The test is conducted by loading a particle composition into a needleless syringe as described above, and then discharging the device into a flask containing a carrier fluid in which the particular composition is not soluble (e.g., mineral oil, silicone oil, etc.). The carrier fluid is then collected, and particle size distribution in both the initial composition and the discharged composition is calculated using a suitable particle sizing apparatus, e.g., an Accu-Sizer® model 780 Optical Particle Sizer. Compositions that demonstrate less than about 50%, more preferably less than about 20% reduction in mass mean diameter (as determined by the AccuSizer apparatus) after device actuation are deemed suitable for use in the needleless syringe systems described herein.

Delivery to Human Skin In Vitro and Transepidermal Water Loss

For a powder performance test that more closely parallels eventual practical use, candidate powder compositions can be injected into dermatomed, full thickness human abdomen skin samples. Replicate skin samples after injection can be placed on modified Franz diffusion cells containing 32° C.

water, physiologic saline or buffer. Additives such as surfactants may be used to prevent binding to diffusion cell components. Two kinds of measurements can be made to assess performance of the formulation in the skin.

To measure physical effects, i.e. the effect of particle injection on the barrier function of skin, the transepidermal water loss (TEWL) can be measured. Measurement is performed at equilibrium (about 1 hour) using a Tewameter TM 210® (Courage & Khazaka, Koln, Germany) placed on the top of the diffusion cell cap that acts like a ~12 mm chimney. Larger particles and higher injection pressures generate proportionally higher TEWL values in vitro and this has been shown to correlate with results in vivo. Upon particle injection in vitro TEWL values increased from about 7 to about 27 (g/m$^2$h) depending on particle size and helium gas pressure. Helium injection without powder has no effect. In vivo, the skin barrier properties return rapidly to normal as indicated by the TEWL returning to pretreatment values in about 1 hour for most powder sizes. For the largest particles, 53–75 μm, skin samples show 50% recovery in an hour and full recovery by 24 hours.

Delivery to Human Skin In Vitro and Drug Diffusion Rate

To measure the formulation performance in vitro, the drug or antigen component(s) of candidate powders can be collected by complete or aliquot replacement of the Franz cell receiver solution at predetermined time intervals for chemical assay using HPLC. or other suitable analytical technique. Concentration data can be used to generate a delivery profile and calculate a steady state permeation rate. This technique can be used to screen formulations for early indication of drug or antigen binding to skin, drug or antigen dissolution, efficiency of particle penetration of stratum corneum, etc., prior to in vivo studies.

These and other qualitative and quantitative tests can be used to assess the physical and functional suitability of the present powders for use in a high-velocity particle injection device. It is preferred, though not required, that the particles of a powder have the following characteristics: a substantially spherical shape (e.g. an aspect ratio as close as possible to 1); a smooth surface; a suitable active loading content; less than 20% reduction in particle size using the particle attrition test; an envelope density as close as possible to the true density of the constituents (e.g. greater than about 0.5 g/ml); and a MMAD of about 20 to 70 μm with a narrow particle size distribution. The compositions are typically free-flowing (e.g. free-flowing after 8 hours storage at 50% relative humidity and after 24 hours storage at 40% relative humidity). All of these criteria can be assessed using the above-described methods, and are further detailed in the following publications, incorporated herein by reference. Etzler et al (1995) *Part. Part. Syst. Charact.* 12:217; Ghadiri, et al (1992) *IFPRI Final Report, FRR* 16-03 *University of Surrey, UK*; Bellhouse et al (1997) "Needleless delivery of drugs in dry powder form, using shock waves and supersonic gas flow," Plenary Lecture 6, 21$^{st}$ *International Symposium on Shock Waves, Australia*; Kwon et al (1998) *Pharm. Sci.* suppl. 1 (1), 103; and Burkoth et al. (1999) "Transdermal and Transmucosal Powdered Drug Delivery," in Critical Reviews in the Therapeutic Drug Carrier Systems 16(4):331–384, STephen Bruck Ed., Begell House Inc., New York, N.Y.

A powder of the invention may alternatively be used to vaccinate a subject via other routes. For this purpose, the powder may be combined with a suitable carrier or diluent such as Water for Injections or physiologically saline. The resulting vaccine composition is typically administered by injection, for example subcutaneously or intramuscularly.

Whichever route of administration is selected, an effective amount of antigen is delivered to the subject being vaccinated. Generally from 50 ng to 1 mg and more preferably from 1 μg to about 50 μg of antigen will be useful in generating an immune response. The exact amount necessary will vary depending on the age and general condition of the subject to be treated, the particular antigen or antigens selected, the site of administration and other factors. An appropriate effective amount can be readily determined by one of skill in the art.

Dosage treatment may be a single dose schedule or a multiple dose schedule. A multiple dose schedule is one in which a primary course of vaccination may be with 1–10 separate doses, followed by other doses given at subsequent time intervals, chosen to maintain and/or reinforce the immune response, for example at 1–4 months for second dose and, if needed, a subsequent dose(s) after several months. The dosage regimen will also, at least in part, be determined by the need of the subject and be dependent on the judgement of the practitioner. Vaccination will of course generally be effected prior to primary infection with the pathogen against which protection is desired.

C. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

Spray Freeze Drying ("SFD") of Hepatitis B Vaccine Compositions 1.1 Objectives:
  To assess the SFD method for preparing Hepatitis-B vaccine powders and to particularly assess the following formulation parameters: (a) the concentration effect on vaccine; and (b) the solid content effect on particle density.

1.2 Materials:
  Hepatitis B surface antigen (HBsAg, Lot # 64850) was obtained from Rhein Americana S.A. (Argentine Republic). Nominal concentration of the antigen was reported as 1.37 mg/mL in the attached Quality Control Certificate of Analysis. The materials used in the study are reported below in Table 1.1.

TABLE 1.1

Materials used in the study

| Material | Lot # | Source | Comment |
| --- | --- | --- | --- |
| Hepatitis-B surface antigen | 64850 | Rhein Americana S.A. (Argentina Republic) | Nominal concentration at 1.37 mg/mL (20 μg per human dose), ("HBsAg") |

TABLE 1.1-continued

Materials used in the study

| Material | Lot # | Source | Comment |
|---|---|---|---|
| Alum-adjuvanted HBsAg | 17 | Rhein Americana S.A. (Argentina Republic) | 20 µg HBsAg adsorbed to 0.44 mg of alum per vial (~1.0 mL), ("HBsAg/alum") |
| Dextran (MW 10 kDa) | 69H1273 | Sigma (St. Louis, MO) | |
| Mannitol | 127H0960 | Sigma (St. Louis, MO) | |
| trehalose dihydrate | 28H3797 | Sigma (St. Louis, MO) | |

1.3 Formulations:

Table 1.2, below, shows the percent (w/w) composition of the starting liquid formulations, and the targeted composition in 1.0-mg of payload. The key excipients were trehalose, mannitol, and dextran of 10 kDa molecular weight. Trehalose was used since it is capable of stabilizing the protein during lyophilization and long-term storage, and the combination of mannitol and trehalose allows dense particles to be produced during spray-freeze-drying. Dextran was used to improve the powder's flowability, the mechanical properties of the particles, and possibly the overall vaccine composition stability. All liquid formulations were targeted to have a total solid content of 30%.

TABLE 1.2

Composition (% w/w) of HBsAg and HBsAg/alum formulations

| Batch # | 138-20-1 | 138-20-2 | 138-20-3 | 138-20-4A | 138-20-4B | 138-16-1 | 138-20-5 |
|---|---|---|---|---|---|---|---|
| Solid content (%) | 30 | 30 | 30 | 30 | 5 | 30 | 10 |
| Conc. Of HBsAg (human dose/mL) | 403.5 | 407.5 | 403.5 | 403.5 | 403.5 | 15.0 | 5.0 |
| Batch size (dose) | 500 | 500 | 500 | 400 | 300 | 400 | 300 |
| HBsAg solution (mg) | 133.2 | 317.0 | 622.4 | 989.7 | 742.3 | 1891.0 | 5400.0 |
| Trehalose (dihydrate) | 164.5 | 164.4 | 163.4 | 143.1 | 107.3 | 251.2 | 188.0 |
| Mannitol | 199.8 | 199.23 | 198.0 | 172.7 | 129.5 | 303.9 | 228.0 |
| Dextran (10 kDa) | 150.0 | 148.7 | 148.5 | 129.1 | 96.9 | 228.9 | 172.2 |

1.4 Methods:

1.4.1 Vaccine Concentration

A centrifugal filter device, Centriprep, with a 10 kD limit regenerated cellulose membrane and a 15 mL sample container (Millipore, Bedford, Mass.) was used to concentrate the alum-free bulk vaccine. The filter was rinsed twice with 15 mL of nanopure water to remove the trace amount of glycerin present in the filter by centrifugation at 3000 rpm at 5–10° C. (Allegra 6®, Beckman, Fullerton, Calif.). The filter was then rinsed once with a blank buffer at the specified pH. The vaccine solution was centrifuged until a desired amount of permeate was collected. Three separate batches were prepared for three powder formulations.

The alum-adjuvanted bulk vaccine was pooled from vials and centrifuged (Allegra 6R, Beckman, Palo Alto, Calif.) at 3,000 rpm for 10 minutes. The cake was re-suspended with fresh water by vortex prior to formulating with excipients.

1.4.2 Spray-Freeze-Drying

The SFD apparatus featured an ultrasonic atomizer (Sono-Tek Corporation, Milton, N.Y.) having a spraying nozzle (Model #05793) and a power supply (Model #06-05108). The nozzle was equipped with a quasi-electric quartz crystal capable of vibrating at a specific frequency that determines the size of the droplets. The frequency of 60 kHz produces droplets mostly within the range of 20–80 µm. Circular metal pans (16-cm in diameter by 6-cm in height) were used to contain the liquid nitrogen. For the lyophilization, a shelf freeze dryer (Model #TDS2C2B5200, Dura-Stop, FTS System, Stone Ridge, N.Y.) was used. This dryer can hold six metal pans in one batch run. Other apparatus included a magnetic stirrer with magnetic stir bars, and a peristaltic pump (Model #77120-70, MasterFlex C/L, Barnant Company, Barrington, Ill.).

The liquid feed (vaccine formulation) was delivered by the peristaltic pump at a flow rate of 1.5 mL/min into the ultrasonic atomizer (60 kHz) where the liquid formulation was sprayed into the liquid $N_2$-containing pan. After spraying, the pan containing frozen particles in liquid nitrogen was transferred to a pre-cooled freeze dryer (–55° C.). Liquid nitrogen evaporated in a few minutes. The freeze-drying cycle was varied to control particle characteristics, but a typical lyophilization cycle is listed below in Table 1.3.

TABLE 1.3

Freeze-drying cycle

| Stage/Cycle | Conditions |
|---|---|
| Freezing | pre-cool shelf temperature (ST) = –50° C. |
| | ramp at 1.0° C./min to ST = –55° C., hold for 15 min |
| | wait for product temp (PT) = –48° C., hold for 120 min |
| Primary Drying | condenser/vacuum (C/V) switched "on" |
| | when condenser temp. reaches –40 C., vacuum pump turned on |
| | wait for chamber vacuum to reach 150 mT |
| | wait for foreline vacuum to reach 100 mT |
| | ramp at 1.0° C./min to ST = –10° C., hold for 24 hours |

TABLE 1.3-continued

Freeze-drying cycle

| Stage/Cycle | Conditions |
|---|---|
| Secondary Drying | ramp at 1.0° C./min to ST = 20° C., hold for 24 hours |

After drying, the powder-containing pan was transferred into a dry box purged with nitrogen with relative humidity initially held at <20%. The relative humidity was increased gradually to ~40% to equilibrate the powder prior to powder collection.

1.5 Powder Characterization:

1.5.1 Particle Size Analysis

The mean geometric diameter of the particles in the volume distribution was determined using an AccuSizer 780 (Particle Sizing Systems, Santa Barbara, Calif.). Based on the light obscuration technique, the AccuSizer determines the particle size distribution without assuming the shape distribution of the particle. In addition, the size of the particle population between 10% and 90% (volume) was also determined. Each analysis required approximately 5 mg of the powder sample. Powder samples were suspended in light mineral oil and sonicated for 5–10 seconds to remove agglomeration of particles before analysis.

The mean aerodynamic diameter of the particles in the volume distribution was also determined using a dry powder dispersion-based particle size analyser (Aerosizer, API). Here again, each analysis required approximately 5 mg of the powder sample.

As reported below in Table 1.4, the particle size of all powders tested fell in the range of 20–60 μm based on Aerosizer measurement.

TABLE 1.4

Particle size result by Aerosizer

| Batch # | Formulation | D50% (median) size (μm) | D10% (μm) | D90% (μm) |
|---|---|---|---|---|
| 138-20-1 | 2 μg HBsAg | 40.1 | 25.1 | 57.4 |
| 138-20-2 | 5 μg HBsAg | 39.4 | 25.3 | 53.1 |
| 138-20-3 | 10 μg HBsAg | 36.7 | 23.6 | 51.7 |
| 138-20-4A | 20 μg HBsAg | 36.9 | 24.2 | 50.5 |
| 138-20-4B | 20 μg HBsAg (FD/C/S) | 39.8 | 26.9 | 54.6 |
| 138-16-1 | 2 μg HBsAg/ 50 μg alum | 41.0 | 26.2 | 55.9 |
| 138-20-5C | 2 μg HBsAg/ 50 μg g alum SFD/C/S | 42.9 | 31.3 | 54.3 |
| 138-16-1C | 2 μg HBsAg/ 50 μg alum SFD/sieved | na | na | na |

1.5.2 Image Analysis

Visual analysis of the particles was performed using an optical microscope (Model DMR, Leica, Germany) with 10×-eyepiece lens and 10×-objective lens. The system was equipped with a Polaroid camera system for image output. Digital images were captured and stored.

The image pictures of selected formulations are presented in FIGS. 1*a*–1*d*. As can be seen, particle shape was generally spherical, and the estimated particle size consistent with that measured by the Aerosizer.

1.5.3 Scanning Electron Microscopy (SEM)

SEM was performed on an Amray 1810T instrument after powder samples were sputter-coated with gold. Measurement was courtesy of Prof. Geoffrey Lee and Ms. Christine Sonner of the Friedrich-Alexander University in Erlangen, Germany.

The SEM micrographs are presented in FIGS. 2*a*–2*d*. As can be seen, all SFD particles (FIGS. 2*a* and 2*b*) were spherical in shape with wrinkled morphology, suggesting particle shrinkage during drying, while the particles that were formed by a compress, grind and sieve (C/G/S) technique had an irregular shape and surface morphology.

1.5.4 Tap Density

Each powder sample was weighed in a glass vial and gently tapped against the lab bench for 20 times. By visual inspection, water of an equivalent volume to that of the powder was placed into an empty vial of the same type. The tap density of the powder sample could be calculated by dividing the powder sample weight with the water sample weight (assuming water density=1 g/mL).

As summarized in Table 1.5 below, the tap density of all powders was >0.4 g/mL. Higher tap densities are achievable by using a higher solid content, for example, tap densities of >0.6 g/mL were seen when the solid content was raised to 35%.

TABLE 1.5

Tap density result

| Batch # | Formulation | Tap density (g/mL) |
|---|---|---|
| 138-20-1 | 2 μg HBsAg | 0.52 |
| 138-20-2 | 5 μg HBsAg | 0.51 |
| 138-20-3 | 10 μg HBsAg | 0.43 |
| 138-20-4A | 20 μg HBsAg | 0.44 |
| 138-20-4B | 20 μg HBsAg (FD and C/G/S) | 0.49 |
| 138-16-1 | 2 μg HBsAg/ 50 μg alum | 0.51 |
| 138-20-5C | 2 μg HBsAg/ 50 μg alum SFD and C/G/S | 0.42 |
| 138-16-1C | 2 μg HBsAg/ 50 μg alum SFD/sieved | 0.51 |

1.5.5 Moisture Content Analysis

Approximately 4–5 mg of the powder sample was recovered from the trilaminate cassettes and transferred into an aluminium weighing-vessel and the weight was recorded. The sample was loaded into a Karl Fisher Coulometer (Model 737, Brinkmann) equipped with a drying oven (Model 707). The sample was heated to 150° C. for 150 sec with a gas flow rate of 100 mL/min within the drying oven.

As reported below in Table 1.6, the moisture content in the powders ranged from 3.3% to 4.1%. Under the same drying condition, there was no clear correlation between moisture content and chemical composition.

TABLE 1.6

Moisture content result

| Batch # | Formulation | Moisture content (%) |
|---|---|---|
| 138-20-1 | 2 μg HBsAg | 3.9 |
| 138-20-2 | 5 μg HBsAg | 3.6 |
| 138-20-3 | 10 μg HBsAg | 4.1 |

TABLE 1.6-continued

Moisture content result

| Batch # | Formulation | Moisture content (%) |
|---|---|---|
| 138-20-4A | 20 µg HBsAg | 3.7 |
| 138-20-4B | 20 µg HBsAg (FD/C/S) | 3.3 |
| 138-16-1 | 2 µg HBsAg/ 50 µg alum | 3.9 |
| 138-20-5C | 2 µg HBsAg/ 50 µg alum SFD/C/S | 3.3 |
| 138-16-1C | 2 µg HBsAg/ 50 µg alum SFD/sieved | 3.9 |

1.5.6 Particle Attrition Testing

This method allows particle attrition arising from, e.g., particle collisions within the powder injection device to be quantified. This method can be used to assess particle integrity upon contacting the skin prior to penetration indirectly through measuring the mean particle size reduction and particle size distribution changes of the powder after firing from a needleless syringe (powder injection) device. The control sample (prior to firing) was prepared by suspending 5 mg of powder in mineral oil (about 30 mL) in a 40 mL container. The mixture was vortexed/sonicated to make a homogeneous suspension. The particle size distribution was measured using a particle size analyzer (AccuSizer 780, Particle Sizing Systems, Santa Barbara, Calif.). For the post-firing sample, the powder was actuated from the device (PowderJect® powder injection device, PowderJect Pharmaceuticals plc, Oxford, United Kingdom), using trilaminate cassettes and 20 µm polycarbonate membranes to contain the powder, 5 shots at a payload of 2 mg each) into a 1 L Erlenmeyer flask. The flask was coated with 25 mL of light mineral oil and the top was covered with a latex sheet with a 3/16 inch hole in the center. The flask sat for about 2–3 minutes until no flying particles could be seen. The interior wall of the flask was washed with 25 mL of fresh mineral oil and vortexed or shaken vigorously to establish a homogeneous suspension. Fifteen mL of the powder suspension was further diluted with 15-mL of mineral oil and dispensed into a 40 cc tube. Both samples before and after attrition were subject to light obscuration analysis. The experiment was repeated three times and each sample was measured in triplicate. The particle size distribution profile from the post-firing sample was compared with that from the control sample. The decrease in the ratio of the respective mean size represents the extent of particle attrition.

As reported below in Table 1.7, particle size reduction for 3 selected formulations was found to be similar and all less than 30%.

TABLE 1.7

Particle attrition test results

| Samples | Mean Particle Size of pre-Actuation (µm) | Mean Particle Size of post-Actuation (µm) | % Reduction in Mean Size |
|---|---|---|---|
| 138-20-3 | 53.2 | 41.8 | 21.5 |
| 138-20-4A | 53.9 | 41.4 | 23.2 |
| 1380-20-4B | 55.3 | 40.2 | 27.3 |

1.5.7 Reconstitution of Alum-Containing Powder

The alum-containing powder sample (2-mg) was dissolved (reconstituted) in 0.5-mL of water. The optical image of the liquid suspension was taken. This procedure allows alum coagulation to be determined.

Figure 3A:
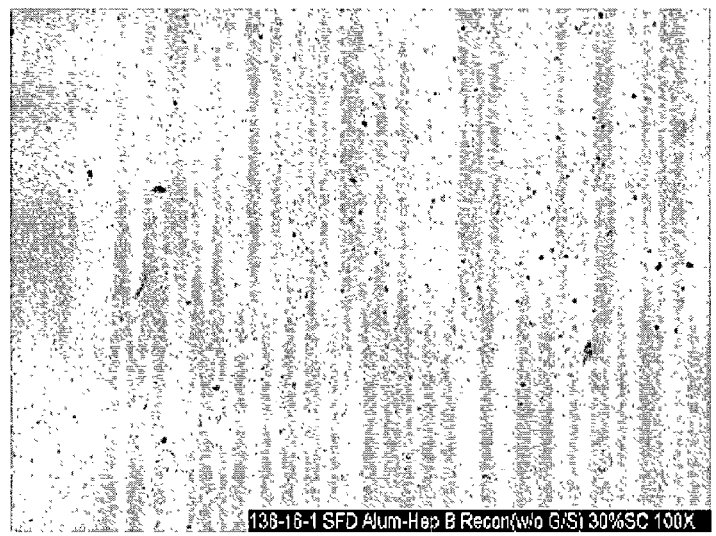
FIGS. 3a and 3b are optical images of liquid suspensions of two alum-containing formulations assessed in the study described in Example 1 at subpart 1.5.7.
Figure 3B:
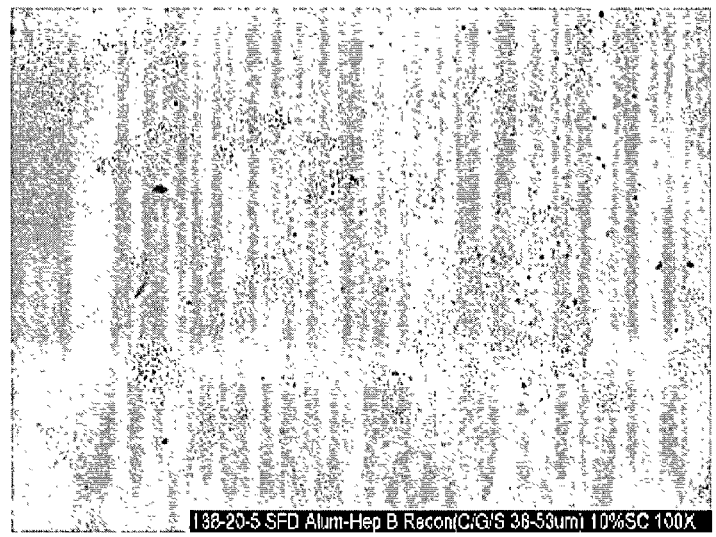

Two alum-containing formulations (batch numbers 138-16-1 & 138-20-5C) were reconstituted in water and their optical micrographs are shown in FIGS. 3a and 3b. The sandy appearance of batch no. 138-16-1 (FIG. 3a) suggests that alum coagulation after SFD is minimal. This is due the fast-freezing phenomenon associated with the SFD process. There is slight coagulation seen with batch no. 138-20-5C. (FIG. 3b) that has the same formulation as batch 138-16-1 but has been further processed using a compress, grind, and sieve technique. This is consistent with a previous observation that compression caused alum to coagulate slightly.

1.5.8 SDS-PAGE Analysis

Coomassie colloidal stained SDS-polyacrylamide gel electrophoresis (SDS-PAGE) was performed on a NU-PAGE gel from Novex (San Diego, Calif.) (4–12% MES, running buffer, sample buffer, and/or dithiothreitol, DTT reducing agent). The alum-adjuvanted powder formulations were reconstituted with water and centrifuged to remove the supernatant. The alum pellet was re-suspended in 200 mM Sodium Phosphate, pH 7 with 0.1% SDS. The liquid suspension was then mixed with sample buffer from the Novex gel kit. The cocktail samples were then heated at 95° C. for 5 minutes and vortexed prior to loading on the gel. The gels were run for 35 minutes at 200V/120 mA/25 W using a Novex PowerEase 500 power supply, and then coomassie stained (Novex Colloidal Blue Stain) and destained with water. A gel image was scanned on a BioRad gel scanner (Model GS-700 Imaging Densitometer). The scanner was equipped with quantitation software (Quantity One) that can quantify the intensity of the gel bands. The unit of signal intensity is Optical Density (O.D.). All samples were compared against a molecular weight marker (Mark 12, Novex).

Figures 4A, 4B:
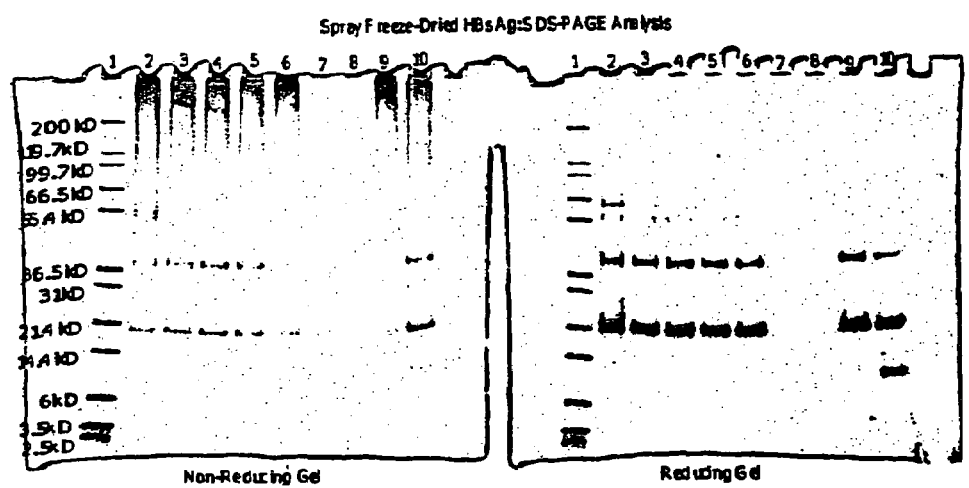
FIGS. 4a and 4b are photos of the non-reducing SDS-PAGE gel (FIG. 4a) and reducing SDS-PAGE gel (FIG. 4b) showing the results of the study described in Example 1 at subpart 1.5.8.
Figure 6A:
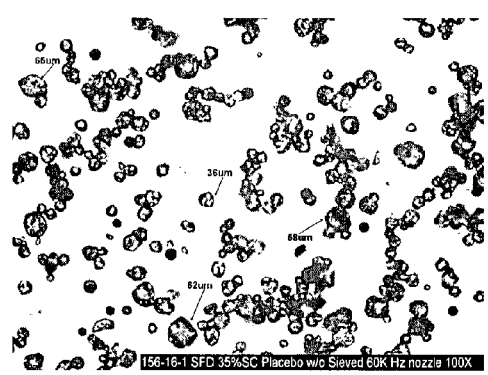
FIGS. 6a–6d are optical micrographs (at ×100 magnification) of selected particle formulations assessed in the study described in Example 2 at subpart 2.5.1.
Figure 6B:
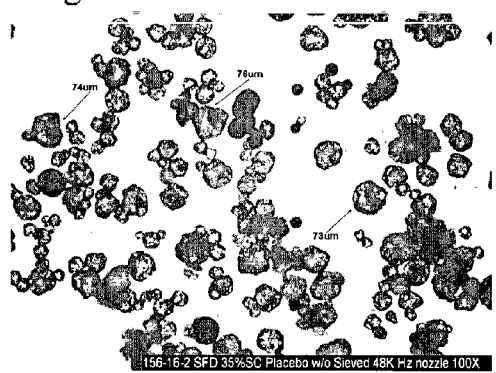
Figure 6C:
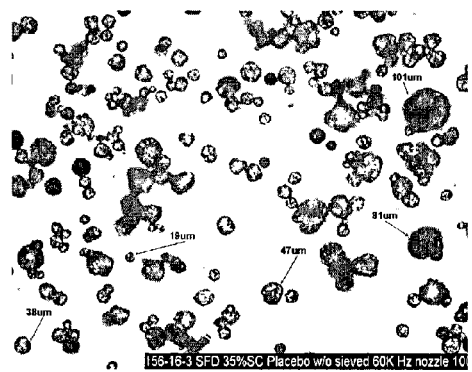
Figure 6D:
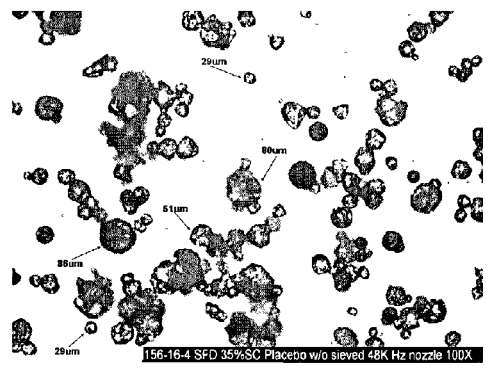
Figure 7A:
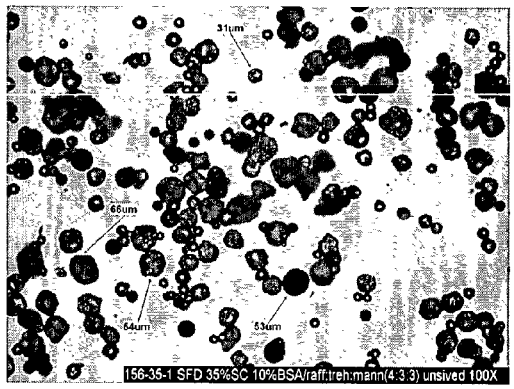
FIGS. 7a–7f are optical micrographs (at ×100 magnification) of selected particle formulations assessed in the study described in Example 2 at subpart 2.5.2.
Figure 7B:
Figure 7C:
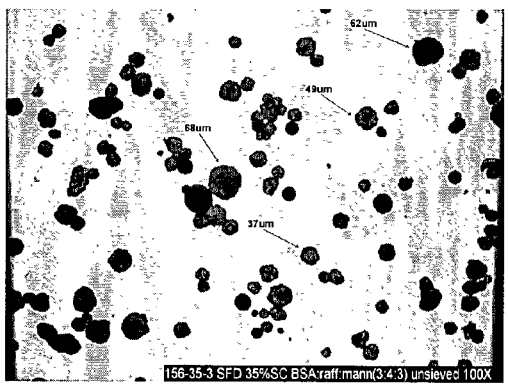
Figure 7D:
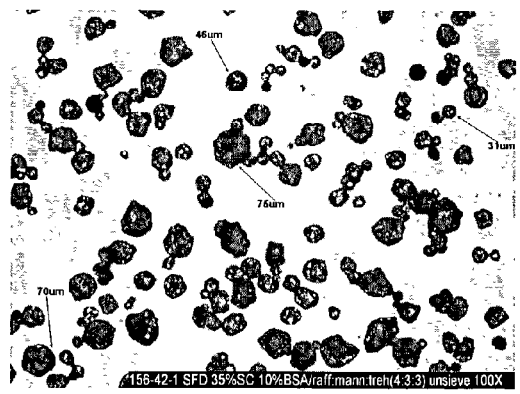
Figure 7E:
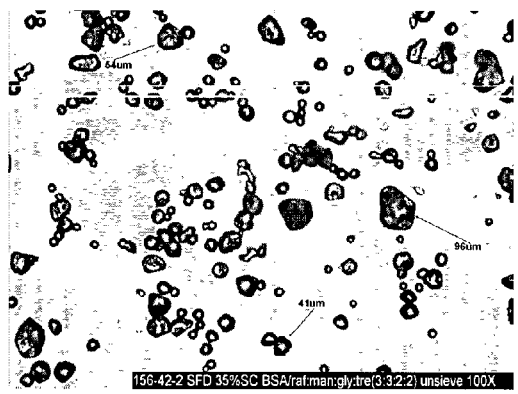
Figure 7F:
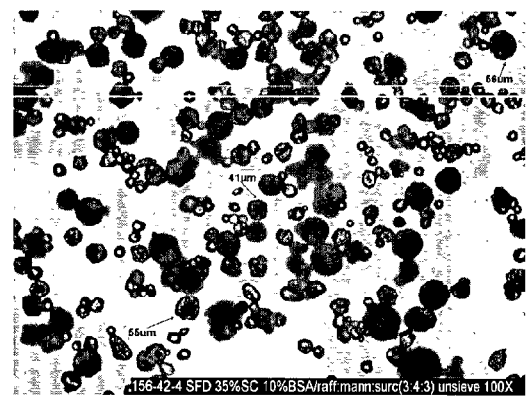
Figure 8A:
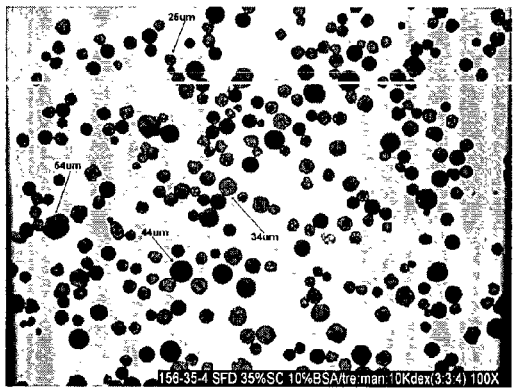
FIGS. 8a–8f are optical micrographs (at ×100 magnification) of selected particle formulations assessed in the study described in Example 2 at subpart 2.5.3.
Figure 8B:
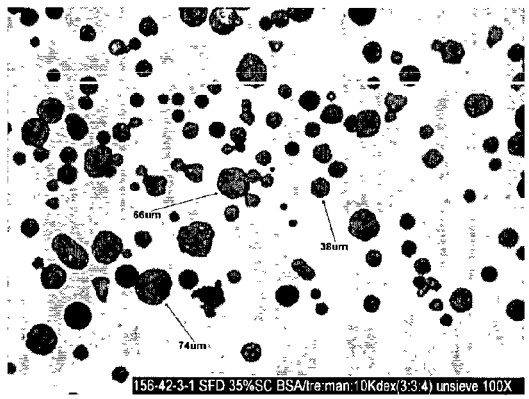
Figure 8C:
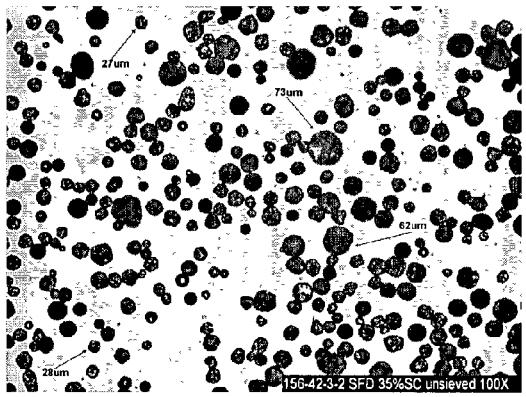
Figure 8D:
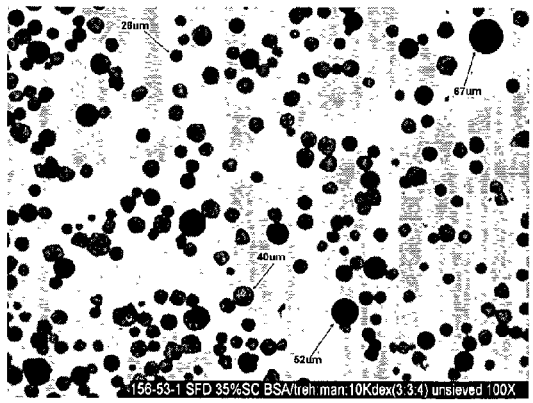
Figure 8E:
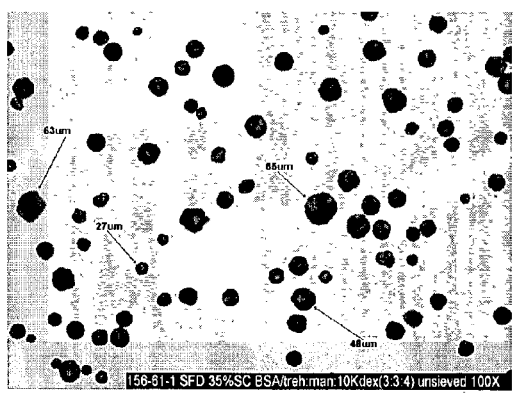
Figure 8F:
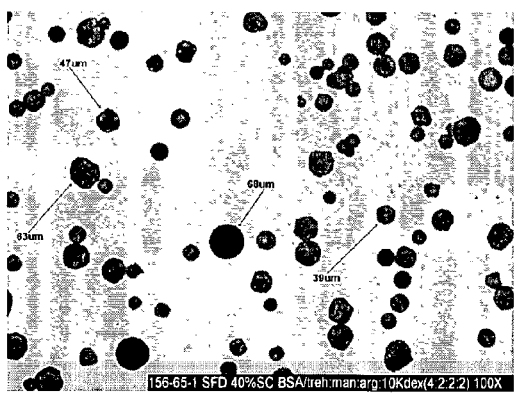

The results of both non-reducing and reducing gels are presented in FIG. 4. As can be seen, no significant differences between the concentrated liquid sample and the SFD samples were observed, showing that the spray-freeze-drying process of the present invention does not affect the antigen quality.

EXAMPLE 2

Spray Freeze Drying ("SFD") of Biopharmaceutical (Protein) Compositions 2.1 Objectives:

To assess the SFD process for use in preparing biopharmaceutical (protein pharmaceutical) powders and to further assess the powdered formulations with respect to the following criteria. (a) particle tap density); (b) particle size distribution; and (c) physical stability of the particles.

A model protein, bovine serum albumin (BSA), was used as the basis for this study on SFD protein powders produced according to the instant invention, and the evaluation of these powders based on physical properties, including particle size, tap density, and physical appearance in terms of hygroscopicity and powder flowability. Another important aspect of the process that was considered was the freeze-drying condition/cycle. Aggressive drying cycles were attempted for two purposes, shortening the drying time and applying higher drying temperatures to facilitate particle collapse during drying.

Spray-freeze-drying allows atomised formulation droplets to be immediately frozen in liquid nitrogen and then freeze dried. The dry powder has a controlled particle size, and the shape of the particle is spherical. This process is highly efficient and has been demonstrated as having as benign effect on biopharmaceuticals such as proteins and peptides. A number of formulation compositions were assessed for their affect on resultant particle density, wherein a range of suitable excipient compositions permits particles of acceptable characteristics to be prepared from widely different proteins and peptides. A typical formulation is the combination of an amorphous sugar to provide protein stability, a crystalline component to render particle strength, and a polymer to offer particle integrity. These excipients must be highly water soluble to achieve a high solid content in the liquid formulation, a parameter that is essential to producing particles of acceptable density. The selection of the particular excipient combination must strike a balance between hygroscopicity of the resulting powder and the short-term and long-term physical stability of the biopharmaceutical guest. Accordingly, these criteria were also applied during the evaluation of the various excipient compositions used in the instant study. All of the excipients used in the study are considered parenterally acceptable and approvable for use in humans.

2.2 Theoretical Considerations of Ultrasonic Atomisation:

Since the atomisation process is an important pre-requisite to attain a fairly narrow particle size distribution, some basic theoretical considerations were addressed.

In simple terms ultrasonic atomisation process results from instabilities created in the liquid capillary waves that form on the atomising surface as a result of the energy provided to the surface in the form of high frequency vibrations. Drops are then formed when the ultrasonic energy exceeds the liquid's surface tension. The size distribution of the drops depends principally on the frequency of the nozzle, as well surface tension and specific gravity, although these are minor factors. Equation 2.1 relates the number median diameter to the frequency, specific gravity and surface tension;

$$d_{N,0.5}=0.34(8\pi s/pf^2)^{1/3} \quad (2.1)$$

wherein s is the surface tension of the liquid, p is the specific gravity and f is the frequency. Thus from Equation 2.1 it can be seen that frequency is the principal factor in determining drop size as it enters the equation as a square, whilst surface tension and the specific gravity only enter as the first power.

The principal consequence of Equation 2.1 is that the droplet diameter is proportional to $f^{2/3}$. This implies that higher operating frequencies produce smaller droplets.

2.3 Spray Freeze Drying (SFD) Apparatus and Methods:

2.3.1 The SFD Apparatus

The SFD apparatus featured an ultrasonic atomizer (Sono-Tek Corporation, Milton, N.Y.) having a spray nozzle (Model #05793) and a power supply (Model #06-05108). The nozzle was equipped with a quasi-electric quartz crystal capable of vibrating at a specific frequency that determines the size of the droplets. Ultrasonic nozzles of 60 and 48 kHz frequencies were used. Circular metal pans (16-cm in diameter by 6-cm in height) were used to contain the liquid nitrogen. For the lyophilization, a shelf freeze dryer (Model #TDS2C2B5200, Dura-Stop, FTS System, Stone Ridge, N.Y.) was used. This dryer can hold six metal pans in one batch run. Other apparatus included a magnetic stirrer with magnetic stir bars, and a peristaltic pump (Model #77120-70, MasterFlex C/L, Barnant Company, Barrington, Ill.). A schematic of the Spray Freeze Drying Process is depicted in FIG. 5.

2.3.2 The SFD Methods

The liquid protein formulation was delivered by the peristaltic pump (flow rate of 1–5 mL/min) into the ultrasonic atomiser (48 or 60 kHz). The liquid formulation was then sprayed into a liquid $N_2$-containing pan. After spraying, the pan containing the frozen particles in liquid nitrogen was transferred to a pre-cooled freeze dryer (−55° C.). Liquid nitrogen will then evaporate. Four sets of freeze-drying conditions that were used in this study are listed below in Tables 2.1–2.4.

TABLE 2.1

Freeze-drying cycle (conservative 48-hour cycle)

| Stage/ Cycle | Conditions |
|---|---|
| Freezing | pre-cool shelf temperature (ST) = −50° C. |
| | ramp at 2.5° C./min to ST = −55° C., hold for 15 min |
| | wait for product temp (PT) = −48° C., hold for 15 min |
| Primary Drying | condenser/vacuum (C/V) switched "on" |
| | when condenser temp. reaches −40° C., vacuum pump turned on |
| | wait for chamber vacuum to reach 150 mT |
| | wait for foreline vacuum to reach 100 mT |
| | ramp at 1.0° C./min to ST = −10° C., hold for 24 hours |
| Secondary Drying | ramp at 1.0° C./min to ST = 20° C., hold for 24 hours |

TABLE 2.2

Freeze-drying cycle (semi-aggressive 20-hour cycle)

| Stage/ Cycle | Conditions |
|---|---|
| Freezing | pre-cool shelf temperature (ST) = −50° C. |
| | ramp at 2.5° C./min to ST = −55° C., hold for 15 min |
| | wait for product temp (PT) = −48° C., hold for 15 min |
| Primary Drying | condenser/vacuum (C/V) switched "on" |
| | when condenser temp. reaches −40° C., vacuum pump turned on |
| | wait for chamber vacuum to reach 150 mT |
| | wait for foreline vacuum to reach 100 mT |
| | ramp at 1.0° C./min to ST = −10° C., hold for 5 hours |
| | ramp at 1.0° C./min to ST = 0° C., hold for 5 hours |
| Secondary Drying | ramp at 1.0° C./min to ST = 15° C., hold for 5 hours |
| | ramp at 1.0° C./min to ST = 25° C., hold for 5 hours |

TABLE 2.3

Freeze-drying cycle (aggressive 20-hour cycle)

| Stage/ Cycle | Conditions |
|---|---|
| Freezing | pre-cool shelf temperature (ST) = −50° C. |
| | ramp at 2.5° C./min to ST = −55° C., hold for 15 min |
| | wait for product temp (PT) = −48° C., hold for 15 min |
| Primary Drying | condenser/vacuum (C/V) switched "on" |
| | when condenser temp. reaches −40° C., vacuum pump turned on |
| | wait for chamber vacuum to reach 150 mT |
| | wait for foreline vacuum to reach 100 mT |
| | ramp at 1.0° C./min to ST = −10° C., hold for 10 hours |
| Secondary Drying | ramp at 1.0° C./min to ST = 15° C., hold for 5 hours |
| | ramp at 1.0° C./min to ST = 25° C., hold for 5 hours |

TABLE 2.4

Freeze-drying cycle (most aggressive 16-hour cycle)

| Stage/Cycle | Conditions |
| --- | --- |
| Freezing | pre-cool shelf temperature (ST) = −50° C.<br>ramp at 2.5° C./min to ST = −55° C., hold for 15 min<br>wait for product temp (PT) = −48° C., hold for 15 min |
| Primary Drying | condenser/vacuum (C/V) switched "on"<br>when condenser temp. reaches −40° C., vacuum pump turned on<br>wait for chamber vacuum to reach 150 mT<br>wait for foreline vacuum to reach 100 mT<br>ramp at 1.0° C./min to ST = −5° C., hold for 6 hours |
| Secondary Drying | ramp at 1.0° C./min to ST = 25° C., hold for 10 hours |

After drying, the powder-containing pan was transferred into a dry box purged with nitrogen to maintain a relative humidity of <30%.

2.4 Powder Characterization:

2.4.1 Particle Size Analysis

The mean geometric diameter of the particles in the volume distribution can be determined using an AccuSizer 780 (Particle Sizing Systems, Santa Barbara, Calif.). Based on the light obscuration technique, AccuSizer determines the particle size distribution without assuming the shape distribution of the particle. In addition, the size of the particle population between 10% and 90% (volume) can also be determined. Each analysis required approximately 5 mg of the powder sample. Powder samples are suspended in light mineral oil and sonicated for 5–10 seconds to remove agglomeration of particles before analysis.

The mean aerodynamic diameter of the particles in the volume distribution was determined using a dry powder dispersion-based particle size analyser (Aerosizer, API). In addition, the size of the particle population between 10% and 90% (in volume distribution) was also reported for each particle size distribution. Each analysis required approximately 5 mg of the powder sample.

2.4.2 Image Analysis

Visual analysis of the particles was performed using an optical microscope (Model DMR, Leica, Germany) with 10×-eyepiece lens and 10×-objective lens. The system was equipped with a Polaroid camera system for image output. Digital images were captured and stored.

2.4.3 Tap Density

Each powder sample was weighed in a glass vial and gently tapped against the lab bench for 20 times. By visual inspection, water of an equivalent volume to that of the powder was placed into an empty vial of the same type. The tap density of the powder sample could be calculated by dividing the powder sample weight with the water sample weight (assuming water density=1 g/mL).

2.4.4 Moisture Content Analysis

Approximately 4–5 mg of the powder sample was recovered from the trilaminate cassettes and transferred into an aluminum weighing-vessel and the weight was recorded. The sample was loaded into a Karl Fisher Coulometer (Model 737, Brinkmann) equipped with a drying oven (Model 707). The sample was heated to 150° C. for 150 sec with a gas flow rate of 100 mL/min within the drying oven. Sample extraction time was 120 seconds.

2.5 Pharmaceutical Formulations and Results:

In the series of experiments discussed herein below, various formulations were tested wherein two excipients were kept constant, namely mannitol and trehalose. Trehalose was selected primarily for stabilizing the protein during lyophilization and long-term storage. Mannitol was added to the formulation to impart rigidity to the particles, as mannitol is a crystalline material.

The powder formulations that were produced using the SFD process of the present invention and the particular apparatus and methods described above. In the first series of experiments, formulations containing polyvinylpyrrolidone (PVP) were assessed. PVP is a parenterally acceptable excipient and imparts plasticity to the formulation, and hence was selected as a preferred bulking agent.

2.5.1 PVP Formulations

In the following series of experiments, the objective was to determine the particle physical properties when the concentration of the PVP bulking agent was altered from 18 to 36% w/w. The particular formulations tested are reported below in Table 2.5.

TABLE 2.5

SFD PVP formulations

| Batch Number | Formulation Composition (% w/w) | Solids Content (% w/w) | Nozzle Freq. (kHz) | Freeze Drying Cycle |
| --- | --- | --- | --- | --- |
| 156-16-1 | 10% BSA, 45% trehalose, 27% mannitol, 18% PVP (K17) and 0.1% Pluronic F68. | 35 | 60 | See Table 2.1 |
| 156-16-2 | 10% BSA, 44.9% trehalose, 26.9% mannitol, 18% PVP (K17), 0.1% methionine and 0.1% Pluronic F68 | 35 | 48 | See Table 2.1 |
| 156-16-3 | 10% BSA, 26.9% trehalose, 26.9% mannitol, 35.9% PVP (K17), 0.1% methionine and 0.1% Pluronic F68. | 35 | 60 | See Table 2.1 |
| 156-16-4 | 10% BSA, 26.9% trehalose, 26.9% mannitol, 35.9% PVP (K17), 0.1% methionine and 0.1% Pluronic F68. | 35 | 48 | See Table 2.1 |

Image Analysis Results:

Photomicrographs (FIGS. 6a–6d) of the SFD formulations defined in Table 2.5 reveal that the particles are of a spherical morphology, with a fairly uniform particle size. There are some particles that are agglomerated, which is a consequence of PVP present in the formulations. PVP is an effective binder, and formulations containing this excipient will have some tendency to agglomerate due to the adhesive nature of the polymeric excipient.

Particle Size Results:

As seen below in Table 2.6, the mean particle sizes of the PVP formulations were similar, with the exception of batch number 156-16-3, which had a smaller mean particle size. Comparison of batches 156-16-1 and 156-16-3, which were both manufactured using a 60 kHz ultrasonic nozzle (the only difference between the two formulations being the ratio of the excipients), reveals that the 3:3:4 excipient ratio produced smaller particles. Similarly, comparison of batches 156-16-2 and 156-16-4 showed the same trend, although the effect was less marked.

TABLE 2.6

Particle size results

| Batch number | Mean Size (μm) | $D_{0.10}$–$D_{0.90}$ | Median size (μm) |
|---|---|---|---|
| 156-16-1 | 39.2 ± 1.4 | 24.9–59.3 | 40.0 |
| 156-16-2 | 40.4 ± 1.4 | 26.8–60.3 | 40.8 |
| 156-16-3 | 36.3 ± 1.3 | 24.7–52.7 | 36.6 |
| 156-16-4 | 39.6 ± 1.4 | 26.3–58.9 | 39.9 |

Moisture Content Analysis:

The Karl Fischer results presented in Table 2.7, below, reveal that the moisture content of all of the PVP formulations was <3%. These results further indicate that the ratio of excipients 3:3:4 produced a drier product.

TABLE 2.7

Karl Fischer (moisture content) results

| Batch Number | % Moisture |
|---|---|
| 156-16-1 | 2.9 |
| 156-16-2 | 2.9 |
| 156-16-3 | 1.9 |
| 156-16-4 | 2.4 |

Particle Density Results:

As can be seen by the results reported in Table 2.8 below, the tap densities of all four PVP formulations were similar and within acceptable ranges.

TABLE 2.8

Tap density

| Batch Number | Tap Density (g/cm$^3$) |
|---|---|
| 156-16-1 | 0.65 |
| 156-16-2 | 0.66 |
| 156-16-3 | 0.64 |
| 156-16-4 | 0.67 |

2.5.2 Various Sugar Formulations

In the following series of experiments, the objective was to determine the particle physical properties using differing combinations of sugars (raffinose, sucrose) and other common excipients (glycine). The particular formulations tested are reported below in Table 2.9.

TABLE 2.9

SFD sugar formulations

| Batch Number | Formulation Composition (% w/w) | Solids Content (% w/w) | Ultrasonic Nozzle frequency (kHz) | Freeze Drying Cycle |
|---|---|---|---|---|
| 156-35-1 | 10% BSA, 36% raffinose, 27% trehalose, 27% mannitol. | 35 | 60 | See Table 2.2 |
| 156-35-2 | 10% BSA, 36% raffinose, 36% mannitol and 18% PVP (K17). | 35 | 60 | See Table 2.2 |
| 156-35-3 | 30% BSA, 40% raffinose and 30% mannitol. | 35 | 60 | See Table 2.2 |
| 156-42-1 | 10% BSA, 36% raffinose, 27% trehalose, 27% mannitol. | 35 | 60 | See Table 2.3 |
| 156-42-2 | 10% BSA, 27% raffinose, 27% mannitol 18% glycine and 18% trehalose. | 35 | 60 | See Table 2.3 |
| 156-42-4 | 10% BSA, 27% raffinose, 27% sucrose and 36% mannitol. | 35 | 60 | See Table 2.3 |

Image Analysis Results:

As can be seen in FIGS. 7a–7f, the particles prepared by the SFD process from the formulations defined in Table 2.9 have a spherical morphology, with a fairly uniform particle size. However, batch numbers 156-35-1, 156-35-2 and 156-35-3 (FIGS. 7a, 7b and 7c, respectively) appear to have a few oversize particles. Batch number 156-42-2 (FIG. 7e) had an irregular morphology and appears to be in the process of deliquescence, suggesting the highly hygroscopic nature of the formulation.

Particle Size Results:

The particle size results of the formulations of Table 2.9 are reported below in Table 2.10 and generally correspond to the estimated sizes obtained from the photomicrographs.

TABLE 2.10

Particle Size Results

| Batch Number | Mean Size (μm) | $D_{0.10}$–$D_{0.90}$ | Median size (μm) |
|---|---|---|---|
| 156-35-1 | 39.5 ± 1.3 | 27.4–55.3 | 40.1 |
| 156-35-2 | 38.9 ± 1.3 | 26.0–55.7 | 39.8 |
| 156-35-3 | 34.4 ± 1.4 | 22.7–50.0 | 35.3 |
| 156-42-1 | 34.4 ± 1.3 | 23.3–49.5 | 35.1 |
| 156-42-2 | 36.1 ± 1.3 | 26.4–48.8 | 36.4 |
| 156-42-4 | 38.8 ± 1.3 | 27.4–52.9 | 40.0 |

Moisture Content Analysis:

The Karl Fischer results presented in Table 2.11, below, reveal that the moisture content of all of the tested formulations was <5%. As can be seen, batch number 156-35-2 had the lowest residual moisture, likely due to the increased amount of mannitol in that formulation.

TABLE 2.11

Karl Fischer (moisture content) results

| Batch Number | % Moisture |
|---|---|
| 156-35-1 | 4.8 |
| 156-35-2 | 3.0 |
| 156-35-3 | 4.2 |

Particle Density Results:

As can be seen by the results reported in Table 2.12, below, the tap densities of all of the tested formulations were similar and within acceptable ranges. As can also be seen, the addition of glycine to formulation for batch number 156-42-2 caused a marked increase in tap density relative to the other formulations. The variables that can alter tap density of a powder are multifaceted and depend principally on the particle size, particle size distribution, crystal habit and rugosity. Alterations in these variables by introduction of another excipient or an increase in the amount of excipient/active formulation will lead to predictable differences in particle tap densities.

The use of raffinose as a bulking agent in these formulations resulted in particles of acceptable physical characteristics, and there was a lower incidence of agglomeration when compared to the PVP formulations.

TABLE 2.12

Tap density

| Batch Number | Tap Density (g/cm$^3$) |
| --- | --- |
| 156-35-1 | 0.65 |
| 156-35-2 | 0.57 |
| 156-35-3 | 0.59 |
| 156-42-1 | 0.68 |
| 156-42-2 | 0.75 |
| 156-42-4 | 0.67 |

2.5.3 Various Dextran Formulations

In the following series of experiments, the objective was to determine the particle physical properties using dextran as the bulking agent. Dextran forms a glass having a high glass transition temperature (TG). The particular dextran-containing formulations tested are reported below in Table 2.13.

TABLE 2.13

SFD dextran formulations

| Batch Number | Formulation Composition (% w/w) | Solids Content (% w/w) | Nozzle frequency (kHz) | Freeze Drying Cycle |
| --- | --- | --- | --- | --- |
| 156-35-4 | 10% BSA, 27% trehalose, 27% mannitol and 36% dextran (10 kDa). | 35 | 60 | See Table 2.2 |
| 156-42-3-1 | 10% BSA, 27% trehalose, 27% mannitol and 36% dextran (10 kDa). | 35 | 60 | See Table 2.3 |
| 156-42-3-2 | 10% BSA, 27% trehalose, 27% mannitol and 36% dextran (10 kDa). | 35 | 60 | See Table 2.3 |
| 156-53-1 | 10% BSA, 27% trehalose, 27% mannitol and 36% dextran (10 kDa). | 35 | 60 | See Table 2.4 |
| 156-61-1 | 10% BSA, 27% trehalose, 27% mannitol and 36% dextran (10 kDa). | 35 | 60 | See Table 2.4 |
| 156-65-1 | 10% BSA, 36% trehalose, 18% mannitol, 18% arginine glutamate, 18% dextran (10 kDa). | 40 | 60 | See Table 2.4 |

Image Analysis Results:

As can be seen in FIGS. 8a–8f, the SFD dextran formulations (defined in Table 2.13) provided particles with a spherical morphology, a narrow size distribution and there was also a noticeable lack of agglomerated particles.

Particle Size Results:

The particle size results from the assessment of the various dextran batches (the formulations of Table 2.13) are reported herein below in Table 2.14, and generally correspond to the estimated sizes obtained from the photomicrographs. As can be seen, there was a marked increase in the mean particle size of batch number 156-53-1 when compared to batch number 156-42-3-1, but this can be explained by the PSD generated by the Aerosizer, which was skewed more to the right, when compared with the PSD of batch number 156-42-3-1, which is indicative of large particles. Batch number 156-61-1, which is a scaled-up formulation of batch number 156-53-1 yielded a similar PSD. Batches numbers 156-53-1 and 156-42-3-1 have similar BSA and excipient compositions, however a freeze-drying cycle of 16 hours was utilised for the former.

These Aerosizer data also reveal that there was a marked increase in the mean particle size when using a shorter drying cycle, however inspection of FIGS. 8*c* and 8*f* does not show any significant differences in terms of morphology or size. From these data it can be postulated that a longer drying cycle results in a more collapsed particle and this may have an effect on the intra-particle porosity, in which case this would affect the particle size as measured by the Aerosizer as the aerodynamic size depends on intraparticle porosity. Batch number 156-65-1 had the largest mean particle size. This can be attributed to the increase in solids content relative to the other dextran formulations of Table 2.13.

TABLE 2.14

Particle size results

| Batch number | Mean Size (μm) | $D_{0.10}$–$D_{0.90}$ | Median size (μm) |
|---|---|---|---|
| 156-35-4 | 33.1 ± 1.3 | 23.3–46.1 | 33.6 |
| 156-42-3-1 | 35.0 ± 1.3 | 24.7–49.1 | 35.4 |
| 156-42-3-2 | 33.6 ± 1.3 | 23.4–47.3 | 34.2 |
| 156-53-1 | 39.2 ± 1.4 | 26.2–57.6 | 39.9 |
| 156-61-1 | 39.7 ± 1.4 | 25.4–61.9 | 40.1 |
| 156-65-1 | 45.3 ± 1.3 | 30.8–64.9 | 46.5 |

Particle Density Results:

As can be seen by the results reported in Table 2.15, below, the tap densities of all of the tested dextran formulations were similar and within acceptable ranges. A review of these densities also indicates that the freeze-drying time had a negligible overall effect on the tap density.

The marked increase in the mean particle size of batch number 156-53-1, when compared to batch number 156-42-3-1, can not be due to the production of a more collapsed particle as the tap densities and light microscopy photomicrographs would have indicated a difference between the two batches, hence the difference between the mean particle sizes of the two batches is attributed to sampling variability.

TABLE 2.15

Tap density

| Batch Number | Tapped Density (g/cm$^3$) |
|---|---|
| 156-35-4 | 0.54 |
| 156-42-3-1 | 0.57 |
| 156-42-3-2 | 0.56 |
| 156-53-1 | 0.53 |
| 156-61-1 | 0.56 |
| 156-65-1 | 0.61 |

2.5.4 Various Salt Formulations

In the following series of experiments, the objective was to determine the particle physical properties of formulations incorporating differing combinations of a salt bulking agent (arginine glutamate) and other common excipients (alanine, Pluronic, methionine). The particular formulations tested are reported below in Table 2.16.

TABLE 2.16

SFD salt formulations

| Batch Number | Formulation Composition (% w/w) | Solids Content | Nozzle Frequency (kHz) | Freeze drying Cycle |
|---|---|---|---|---|
| 156-57-1 | 10% BSA, 36% trehalose, 36% mannitol, 18% alanine. | 35 | 60 | See Table 2.3 |
| 156-57-2 | 10% BSA, 27% trehalose, 27% mannitol 36% arginine glutamate. | 35 | 60 | See Table 2.3 |
| 156-65-2 | 10% BSA, 36% trehalose, 18% mannitol, 36% arginine glutamate. | 40 | 60 | See Table 2.4 |
| 156-71-1 | 10% BSA, 36% trehalose, 18% mannitol, 36% arginine glutamate. | 40 | 60 | See Table 2.1 |
| 156-76-1 | 10% BSA, 35.9% trehalose, 18% mannitol, 35.9% arginine glutamate, 0.1% Pluronic F168 and 0.1% methionine. | 35 | 60 | See Table 2.4 |
| 156-76-2 | 10% BSA, 26.9% trehalose, 26.9% mannitol, 35.9% arginine glutamate, 0.1% Pluronic F168 and 0.1% methionine. | 35 | 48 | See Table 2.4 |

Figure 9A:
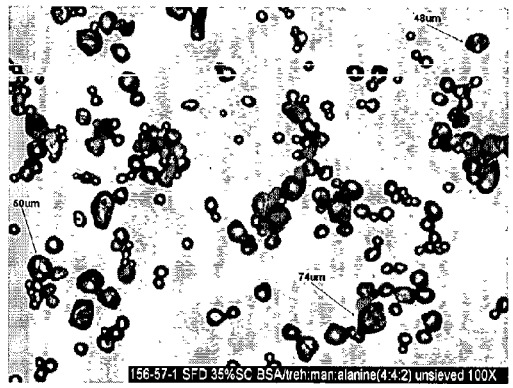
FIGS. 9a–9f are optical micrographs (at ×100 magnification) of selected particle formulations assessed in the study described in Example 2 at subpart 2.5.4.
Figure 9B:
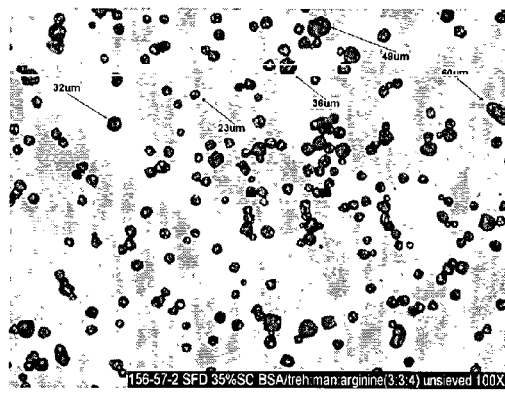
Figure 9C:
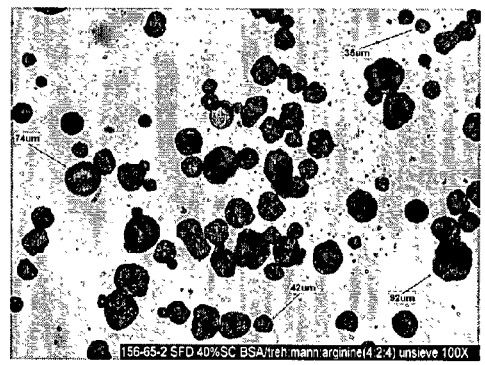
Figure 9D:
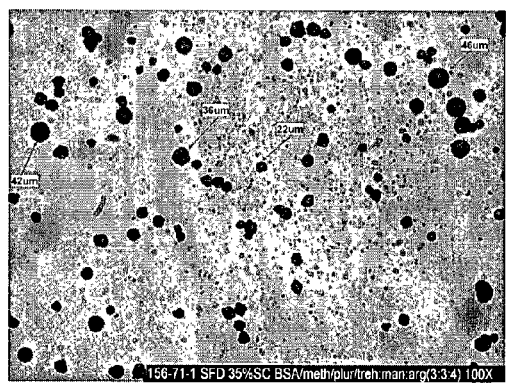
Figure 9E:
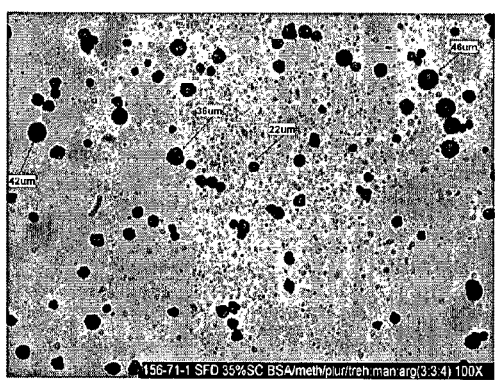
Figure 9F:
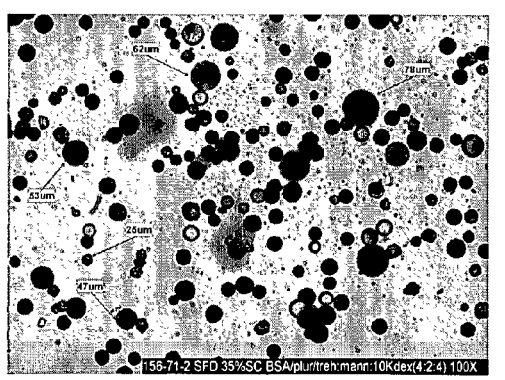

Image Analysis Results:

As can be seen in FIGS. 9a–9f, the SFD salt formulations defined in Table 2.16, provided particles with a spherical morphology and narrow size distribution. FIG. 9a is a photomicrograph of batch number 156-57-1, which shows that the particles have agglomerated after the freeze drying process, moreover the particles shown in FIG. 9a have a thick rounded edge, which is indicative of deliquescence. The other salt formulations do not show any evidence of agglomeration.

Accordingly, X-ray powder diffraction (XRPD) was conducted on the arginine glutamate and a spray freeze dried formulation containing the aforementioned excipient. This was conducted to elucidate the morphology of the excipient prior to freeze drying and after freeze drying. Analysis of the XRPD pattern for arginine glutamate prior to freeze drying showed distinct peaks, which is indicative of a crystalline material. Analysis of the XRPD pattern for batch number 156-76-1 showed a diffuse halo, suggesting an amorphous formulation.

Particle Size Results:

The particle size results of the various salt formulations (the formulations of Table 2.16) are reported herein below in Table 2.17, and generally correspond to the estimated sizes obtained from the photomicrographs.

TABLE 2.17

Particle size results

| Batch number | Mean Size (μm) | $D_{0.10}$–$D_{0.90}$ | Median size (μm) |
|---|---|---|---|
| 156-57-1 | 40.3 ± 1.3 | 27.8–57.6 | 40.8 |
| 156-57-2 | 37.7 ± 1.4 | 23.7–58.0 | 38.3 |
| 156-65-2 | 44.1 ± 1.4 | 28.2–66.1 | 45.4 |
| 156-71-1 | 41.3 ± 1.4 | 26.0–63.5 | 42.7 |

Particle Density Results:

As can be seen by the results reported in Table 2.18, below, the tap densities of all of the tested formulations were relatively high, with the single exception of batch number 156-76-1, and all within acceptable ranges. These results demonstrate that the use of arginine glutamate as the bulking agent in the formulations of the present invention provides particles of acceptable physical characteristics, however, the use of alanine was not deemed optimal due the deliquescence of the formulation.

TABLE 2.18

Tap density

| Batch Number | Tapped Density (g/cm$^3$) |
|---|---|
| 156-57-1 | 0.67 |
| 156-57-2 | 0.69 |
| 156-65-2 | 0.63 |
| 156-71-1 | 0.66 |
| 156-76-1 | 0.46 |
| 156-76-2 | 0.57 |

2.5.5 Further Salt Formulations

As with the above series of experiments, the objective of this series of experiments was to determine the particle physical properties of formulations incorporating combinations of different alternative bulking agents (arginine aspartate) and other common excipients (Pluronic F168, methionine, Tween 80). The particular formulations tested are reported below in Table 2.19.

TABLE 2.19

SFD formulations

| Batch Number | Formulation Composition (% w/w) | Solids Content | Nozzle frequency (kHz) | Freeze drying cycle |
|---|---|---|---|---|
| 156-80-1 | 10% BSA, 27% trehalose, 27% mannitol, 36% arginine aspartate. | 35 | 60 | See Table 2.4 |
| 156-80-2 | 10% BSA, 5% Pluronic F168, 59.5% trehalose and 25.5% mannitol. | 35 | 60 | See Table 2.4 |
| 156-80-3 | 10% BSA, 35.9% trehalose, 18% mannitol, 35.9% arginine glutamate, 0.1% methionine and 0.1% Tween 80. | 40 | 60 | See Table 2.4 |

Figure 10A:
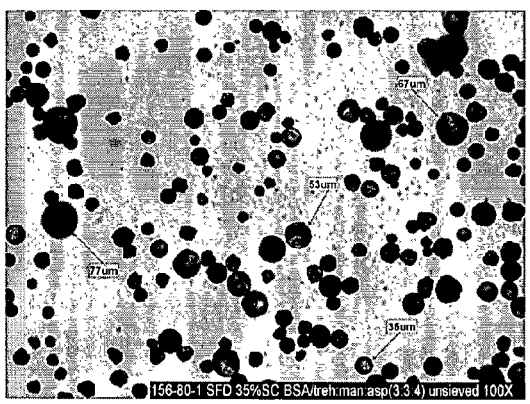
FIGS. 10a–10c are optical micrographs (at ×100 magnification) of selected particle formulations assessed in the study described in Example 2 at subpart 2.5.5.
Figure 10B:
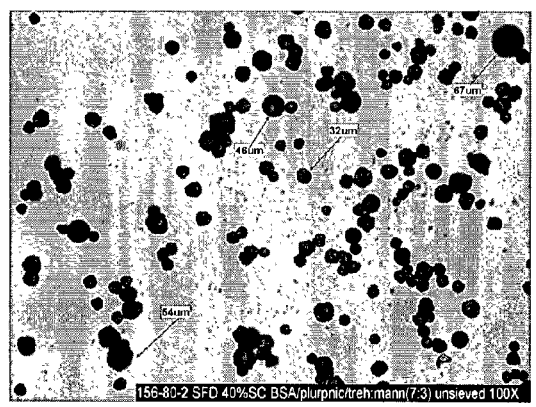
Figure 10C:
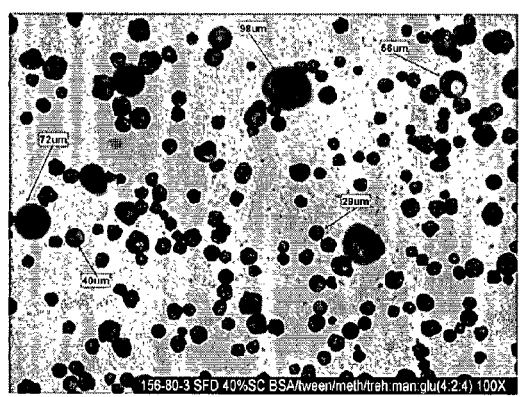
Figure 11A:
FIGS. 11a–11d are optical micrographs of selected particle formulations assessed in the study described in Example 3 at subpart 3.4.
Figure 11B:
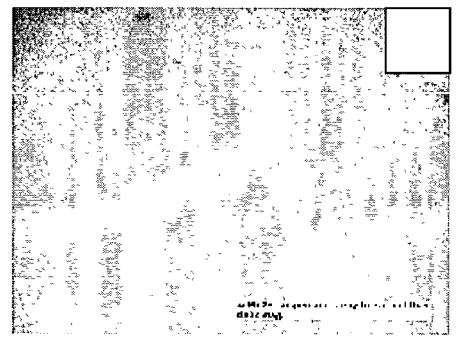
Figure 11C:
Figure 11D:
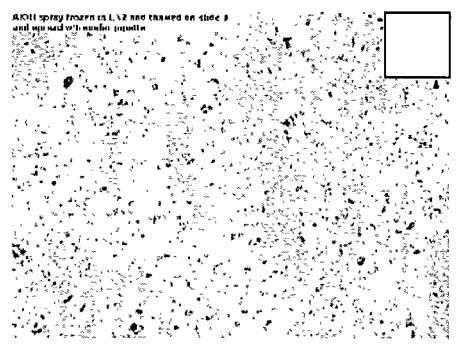

Image Analysis Results:

As can be seen in FIGS. 10a–10c, the SFD salt formulations defined in Table 2.19 produced particles with a spherical morphology. However, a number of oversize particles are evident, particularly in batch number 156-80-3. In addition, batch number 156-80-2 (FIG. 10b) had particles that seemed to be fused together, likely as a consequence of the high Pluronic content in the formulation.

Particle Size Results:

The particle size results of the various salt formulations (the formulations of Table 2.19) are reported herein below in Table 2.20, and generally correspond to the estimated sizes obtained from the photomicrographs depicted in FIGS. 10a–10c. Batch number 156-80-1 yielded the smallest mean particle size, due to the lower solids content used, whilst batch number 156-80-2 yielded the largest particle size which was partially as a consequence of particle agglomeration/fusion (see FIG. 10b).

TABLE 2.20

Particle size results

| Batch number | Mean Size (µm) | $D_{0.10}$–$D_{0.90}$ | Median size (µm) |
|---|---|---|---|
| 156-80-1 | 33.6 ± 1.4 | 22.5–48.4 | 34.6 |
| 156-80-2 | 41.8 ± 1.4 | 26.2–63.2 | 43.4 |
| 156-80-3 | 37.7 ± 1.4 | 24.9–55.9 | 38.6 |

Particle Density Results:

As can be seen by the results reported in Table 2.21, below, the tap densities of all of the tested formulations were relatively high and within acceptable ranges. The formulation of batch number 156-80-1 had a relatively lower density due to a lower starting solids content (35%). These results demonstrate that the use of arginine aspartate as the bulking agent in the formulations of the present invention provides particles of acceptable physical characteristics.

TABLE 2.21

Tap density

| Batch Number | Tapped Density (g/cm³) |
|---|---|
| 156-80-1 | 0.51 |
| 156-80-2 | 0.72 |
| 156-80-3 | 0.63 |

EXAMPLE 3

Spray Freeze Drying of Alum-Adjuvanted Vaccine Compositions 3.1 Objectives:

To assess the SFD process for use in preparing alum-adjuvanted vaccine powders and to further assess the powdered formulations with respect to their in vivo performance using epidermal powder immunization ("EPI") and conventional needle and syringe administration techniques. Hepatitis B vaccine (Alum-HBsAg) and a diphtheria/tetanus toxoid vaccine (Alum-DT) were selected for the studies since the Alum-HBsAg composition contains aluminium hydroxide adjuvant and the Alum-DT composition contains aluminium phosphate adjuvant.

3.2 Materials:

The chemicals and excipients that were used to produce the various vaccine compositions used in this study are summarized in Table 3.1 below. All alum formulations were concentrated by centrifugation (Allergra 6R Centrifuge, Beckman Instrument, Palo Alto, Calif.) prior to use.

TABLE 3.1

Chemicals/excipients used in the study.

| Chemical | Lot # | Source | Comment |
|---|---|---|---|
| Aluminum phosphate (Adjus-Phos, 2% AlPO₄) | 8934 | Accurate Chemical and Scientific (Westbury, NJ) | Manufactured by HCI Biosector (Frederikssund, Denmark) |
| Aluminum hydroxide (Alhydrogel, 3% Al(OH)₃) | | Accurate Chemical and Scientific | Manufactured by Superflos Biosector (Vedbaek, Denmark) |
| Diphtheria toxoid (dT, MW 58 kDa) | G9334 | Accurate Chemical and Scientific | Manufactured by Statens Serum Institute, Denmark, and provided at 5 mg/mL (1 Lf = 2.42 µg), used as supplied. |
| Tetanus toxoid (tT, MW 150 kDa) | G9486 | Accurate Chemical and Scientific | Manufactured by Statens Serum Institute, Denmark, and provided at 2 mg/mL (1 Lf = 2.44 µg), used as supplied. |
| Alum phosphate-adjuvanted DT | | CSL Limited (Parkville, Australia) | Bulk containing 5 w/v % alum phosphate adsorbed with both dT and tT at 563 Lf/mL |
| Alum hydroxide-adjuvanted hepatitis-B surface antigen (HBsAg) | | Rhein Amaericana S.A. (Buenos Ares, Argentina) | 20 µg HBsAg adsorbed to 0.5 mg of aluminum or 1.5-mg of aluminum hydroxide. |
| Dextran (MW 37,500 Da) | 18H0568 | Sigma (St. Louis, MO) | Reagent grade, used as supplied |
| Glycine | 28H0103 | Sigma | Reagent grade, used as supplied |
| Mannitol | 127H0960 | Sigma | Reagent grade, used as supplied |
| Trehalose dihydrate | 28H3797 | Sigma | Reagent grade, used as supplied |

3.3 Methods:

3.3.1 Spray-Freezing (SF) and Spray-Freeze-Drying (SFD)

Liquid formulations were delivered by a peristaltic pump (Model #77120-70, MasterFlex C/L, Barnant Company, Barrington, Ill.) at a flow rate of 2.0 mL/min into an ultrasonic atomizing system (Sono-Tek Corporation, Milton, N.Y.) consisting of a spray nozzle (Model #05793) and a power supply (Model #06-05108). The nozzle is equipped with a quasi-electric quartz crystal capable of vibrating at a specific frequency that determines the size of the droplets. A 60 kHz spraying nozzle produces droplets mostly within the range of 20–80 µm. Atomized droplets were sprayed into a liquid $N_2$-containing pan (16 cm in diameter by 6 cm in height). For formulations subjected to the spray-freezing/thawing experiment, the frozen powder was transferred to a glass vial and thawed at ambient conditions. For frozen droplets undergoing drying, the pan containing frozen particles in liquid nitrogen was transferred to a pre-cooled (−55° C.) shelf freeze dryer (Model #TDS2C2B5200, Dura-Stop, FTS System, Stone Ridge, N.Y.). The liquid nitrogen evaporated in a few minutes. The freeze-drying condition was set at −25° C. for 18 hours and 20° C. for 10 hours. The ramping rate was 1° C./minute consistently. The vacuum pressure was 100 ml throughout the cycle. After drying, the powder-containing pans were transferred into a dry box purged with nitrogen (at <30% relative humidity) for powder collection. The same lyophilization cycle was used for liquid formulations without SF with freezing achieved by storing in a −20° C. freezer overnight.

3.3.2 Powder Formation by Compress/Grind/Sieve (C/G/S) Method

To prepare powders of high density for the epidermal powder immunization (EPI) study, freeze-dried (FD) and SFD formulations were compressed in a stainless steel dye of 13-mm in diameter (Carver Press, Wabash, Ind.) at a pressure of 12,000–15,000 pounds for 5–10 minutes. The compressed discs were ground manually using a mortar and pestle, and then the ground powder was manually sieved through a stack of 3-in sieves (Fisher Scientific Products, Pittsburgh, Pa.) of four sizes, 20, 38, 53, and 75 µm.

3.3.4 Spray-Drying (SD)

A bench-top mini spray dryer (Buchi B-191, Brinkmann, Westbury, N.Y.) was used to prepare placebo alum formulations. Using compressed air from an in-house supply (~80 psi), a two-fluid nozzle (0.5 mm) atomized the aqueous feed solution. The standard operating conditions were: inlet air temperature of 130° C., drying air blown at the full scale, atomizing air flow rate of 500 L/hr, and liquid feed rate of 10 mL/min. This condition resulted in an outlet air temperature of 70° C.

A laboratory spray dryer (Mobile Minor, Niro A/S, Soeborg, Denmark) was used to prepare Alum-DT formulation with the following conditions. The two-fluid nozzle was operated at an atomizing pressure of 2 bar. The inlet air temperature was set at 160° C. drying air with full-blown drying air. As the liquid was fed at 30 mL/min, the air outlet temperature measured at 65–70° C.

3.3.5 Air-Drying (AD)

Liquid alum-adjuvanted vaccine formulations were placed in a polystyrene weigh boat and allowed to dry overnight under the ambient conditions. Gentle agitation by a magnetic bar stirring was applied throughout the process to minimize phase separation.

3.3.6 Optical Microscopy

Visual analysis of the particles was performed using an optical microscope (Model DMR, Leica, Germany) with 10x-eyepiece lens and 10x-objective lens. The system was equipped with a Polaroid camera system for image output.

3.3.7 Particle Size Analysis

The mean geometric/aerodynamic diameter of the particles in the volume distribution was determined using a time-of-flight particle size analyzer (Aerosizer, API, Minneapolis, Minn.). The mean volumetric size was calculated by the software using the density of 1.0 and particle population between 10% ($D_{10}$) and 90% ($D_{90}$) was reported for particle size distribution. Each analysis requires approximately 3–5 mg of the powder sample. For liquid suspensions, the particle size distribution was measured using a light obscuration-based particle size analyzer (AccuSizer 780, Particle Sizing Systems, Santa Barbara, Calif.).

3.3.8 SDS-PAGE

Coomassie colloidal-stained SDS-polyacrylamide gel electrophoresis (SDS-PAGE) was performed on a Nu-PAGE gel from Novex (San Diego, Calif.) (4–12% MES, running buffer, sample buffer, and/or Dithiothreitol reducing agent). The alum-adjuvanted powder vaccine formulations were reconstituted with water and centrifuged to remove the supernatant. The alum pellet was re-suspended in 200 mM sodium phosphate, pH 7 with 0.1% SDS. The liquid suspension was then mixed with sample buffer from the Novex gel kit. The cocktail samples were then heated at 95° C. for 5 minutes and vortexed prior to loading on the gel. The gels were run for 35 minutes at 200V/120 mA/25 W using a power supply (PowerEase 500, Novex), and then coomassie stained (Novex Colloidal Blue Stain) and destained with water. The gel images were scanned on a gel scanner (Model GS-700 Imaging Densitometer, BioRad) equipped with a quantitation software (Quantity One), which can quantify the intensity of the gel bands. The unit of signal intensity is Optical Density (O.D.). All samples were compared against a molecular weight marker (Mark 12, Novex).

3.3.9 EPI Using a PowderJect® Powder Injection Device

A PowderJect® powder injection device (needleless syringe) was used to immunize hairless guinea pigs. The device is approximately 15 cm in length and includes a gas cylinder (5-ml volume), rupture chamber, a trilaminate particle cassette, a nozzle, and a silencer element. The stainless steel gas cylinder is filled with medical grade helium gas to 40-bar pressure. The trilaminate cassette (11-mm O.D., 6-mm I.D., and 4-mm height) is constructed of a thick ethylene vinyl acetate washer with rupture membranes heat sealed to each side within which the powdered vaccine sample is housed. The rupture membranes are formed from a thin film (20 µm) made of semi-transparent polycarbonate. Upon actuation, the helium gas is released from the gas cylinder and causes pressure build-up in the rupture chamber. The escaping gas overcomes the rupture strength of the rupture membranes, causing the membranes to rupture, whereby the gas sweeps through the trilaminate cassette and propels the vaccine powder as projectiles into the skin. The helium gas is reflected off the skin and exhausted through the silencer element. The depth of powder penetration was experimentally optimized to deliver powders to the epidermal layer of the skin for optimal tolerance and maximal efficacy.

3.3.10 Mice Immunization and Serum Collection

Five to seven week-old female BALB/c mice (Harlen-Sprague-Dawley, Indianapolis, Ind.) were used to assess the immunogenicity of powdered alum-adsorbed hepatitis B vaccines. FD and SFD powder formulations were reconstituted with distilled water and administered by intraperitoneal (IP) injection using a 26 ⅕ needle. Each injection administered 200 µl of solution containing 2 µg of hepatitis B surface antigen adsorbed on alum. Control mice were immunized with the same dose of untreated liquid hepatitis B vaccine. A boost immunization was administered on day 28.

Blood was collected via retro-orbital bleeding under anaesthesia prior to each vaccination and two weeks post boost.

3.3.11 Guinea Pig Immunization and Serum Collection

Hairless guinea pigs (Charles River, Wilmington, Mass.) were used to assess the immunogenicity of powder formulations of alum adsorbed diphtheria toxoid (dT) and tetanus toxoid (tT) following EPI. The general methods for EPI are described in detail herein above and in the art. Briefly, one mg of the powdered vaccine compositions being tested was dispensed into a trilaminate cassette. The cassette was inserted into the PowderJect powder injection device at the time of immunization. The device was placed against the left inguinal skin of the animals and actuated by releasing the compressed helium at 40-bar pressure from the gas cylinder. Control animals were immunized with 0.20 mL of DT vaccine in saline by intramuscular (IM) injection using a 26 ½-gauge needle.

Blood was collected via the kerotid blood vessel prior to each vaccination and two weeks post boost.

3.3.12 ELISA

The antibody responses to diptheria toxoid (dT) and tetanus toxoid (tT) components of the Alum-DT vaccine and to the HBsAg antigen component of the Alum-HBsAg vaccine were determined using a modified ELISA method. A 96-well plate (Costar, Fisher Scientific Products, Pittsburgh, Pa.) was coated with 0.1 µg of antigen (HBsAg, dT, or tT) in 30 mM phosphate buffered saline (PBS), pH 7.4, per well overnight at 4° C. Plates were washed 3 times with tris-buffered saline (TBS), pH 7.4, containing 0.1% Brij-35, and incubated with test sera diluted in PBS containing 5% dry milk for 1.5 hr. A standard serum, containing a known level of antibodies to dT, tT, or HBsAg, was added to each plate and used to standardize the titer in the final data analysis. The plates were then washed and incubated with biotin-labeled goat anti-mouse antibodies (1:8,000 in PBS, Southern Biotechnology Associate, Birmingham, Ala.) for 1 hr at room temperature. Finally, the plates were washed and developed with TMB substrate (Bio-Rad Laboratories, Melville, N.Y.). The endpoint titers of the sera were determined by 4-parameter analysis using the Softmax Pro 4.1 program (Molecular Devices, Sunnyvale, Calif.) and defined as the reciprocal of the highest serum dilution with an OD reading above the background by 0.1. A reference serum with a predetermined titer was used on every plate to calibrate the titers and adjust assay-to-assay and plate-to-plate variation.

3.4 Powder Characterization:

Current commercial alum-adjuvanted vaccines are formulated at approximately 2 w/v % of aluminum salt in saline for injection. Accordingly, commercially available vaccine compositions were reviewed before and after freezing using an optical microscope. The results of the study are depicted in FIGS. 11a–11d. Based on optical microscopy, the Adju-Phos adjuvant (2 w/v % placebo $AlPO_4$ gel) shows smooth and sandy texture without discernible particles. After freezing at −20° C., the thawing gel develops immediately significant coagulation (see FIG. 11a), but the same gel shows only slight aggregation (light dots) after spray-freezing (see FIG. 11b). The same difference was observed for the Alhydrogel adjuvant (3 w/v % placebo $Al(OH)_3$) after freezing at −20° C. (see FIG. 11c) and spray-freezing (see the dark particles in FIG. 11d). By appearance, large particles were visible in the gel solution that had been frozen in the −20° C. freezer and they rapidly settled to the bottom of the container. In addition, the volume of the settled alum particles was significantly greater than that of the starting gel. All these observations suggest that alum gels will coagulate after regular freezing. Coagulated alum gels are not reversible even under mechanical force such as sonication or vortexing. On the other hand, the absence of coagulation with the spray-frozen gel confirms that extremely fast freezing significantly reduces the coagulation tendency of alum gel regardless of its salt type even in the absence of bulking or stabilizing agents. After lyophilization of the frozen gels, the extent of coagulation of the reconstituted alum appears to be similar to the freeze/thaw samples, suggesting that freezing is a primary cause of alum coagulation.

3.5 In Vivo Performance:

3.5.1 Effect of Alum Coagulation on Immunogenicity of Alum-HBsAg

A mouse model was used to test if the immunogenicity of the Alum-HBsAg vaccine composition would be affected by the drying methodology and the size of the coagulated particles. Table 3.2, below, summarizes the study.

TABLE 3.2

Immunogenicity Study for Alum-HBsAg powder formulations.

| Group (n = 8) | Formulation | Drying Process (particle size) |
|---|---|---|
| 1 | Q | FD |
| 2 | Q | FD (<20 μm) |
| 3 | Q | FD (38–53 μm) |
| 4 | Q | FD (53–75 μm) |
| 5 | Q | SFD (38–53 μm) |
| 6 | R | SFD (38–53 μm) |
| 7 | Control | not dried (liquid) |

The formulations used in the study were as follows. Formulation Q: Alum hydroxide (3.0 w/v %)/mannitol (1.9 w/v %)/glycine (0.5 w/v %)/dextran (0.61 w/v %) in which the alum concentration was achieved by combining the Alum-HBsAg with the placebo alum hydroxide gel. Formulation R: Alum hydroxide (0.6 w/v %)/mannitol (2.8 w/v %)/glycine (1.2 w/v %)/dextran (0.58 w/v %). Control: the commercial Alum-HBsAg product (Rhein Biotech) used as supplied by the manufacturer.

The SFD powders prepared from Formulations Q and R differ in alum salt concentration. Powders for Groups #2–4 were prepared by compressing the FD Formulation Q followed by grinding and then sieving to produce 3 different particle size-fractions. All powdered compositions were fully characterized as described above in Examples 1 and 2. The optical micrographs of the reconstituted powders again suggested that the SFD powder could be readily re-suspended in water while the FD formulation was highly coagulated. Another characterization method involved re-suspending the powder sample in water and subjecting to light-scattering particle size analysis (AccuSizer). The results of the particle size analysis are depicted in FIGS. 12a and 12b. FIG. 12a shows the alum particle size distribution for the two SFD powders falling in the same particle size range as the starting gel, suggesting no detectable aggregated particles. However, the reconstituted FD/compress/grind/sieve powder (38–45 μm, Group #3 in Table 3.2) shows a particle size range of 5–50 μm with a peak at 45 μm (FIG. 12b), which overlaps with the size of dry particles before rehydration.

In order to assess stability of the Alum-HBsAg compositions upon drying, SDS-PAGE analysis was performed under both non-reducing and reducing conditions. The results from the optical density scans of the non-reduced SDS-PAGE analysis are reported below in Table 3.3.

TABLE 3.3

Optical density of HBsAg band (non-reduced SDS-PAGE)

| Formulation | Light Intensity (O.D.) |
|---|---|
| Formulation Q, FD | 847 |
| Formulation Q FD (particle size <20 μm) | 1235 |
| Formulation Q, FD (particle size 53–75 μm) | 1021 |
| Formulation Q, SFD (particle size 38–53 μm) | 1507 |
| Formulation R, SFD (particle size 38–53 μm) | 1479 |
| Control (liquid) | 1671 |

In its native state, HBsAg is a highly aggregated particle of 22 nm in diameter. No formulations dissociated into monomeric form under the non-reducing condition. However, the light intensity of the single band at the top of the SDS-PAGE gel differs among the formulations (Table 3.3). For example, the light intensity for the two SFD formulations is slightly lower than that for the control (starting liquid formulation). The FD formulation showed the lightest band while band intensity increased when the FD formulation was formulated into particles using C/G/S. Interestingly, band intensity increased with decreasing particle size. This observation appears to be related to alum gel coagulation since the antigen desorption from the surface of aggregated alum particles may be restricted or blocked. Grinding the FD alum gel generated new surfaces exposing more antigen. The powder's specific surface area increases as the particle size decreases. Under reducing conditions, HBsAg particles were reduced to monomers of approximately 24 kDa. There was no difference observed in band pattern and intensity among all the formulations. This is probably due to the ease with which monomeric HBsAg can diffuse out of the tightly packed alum aggregates.

Immunogenicity of the various Alum-HBsAg formulations described in Table 3.2 above was tested in the mouse model. The dose of HBsAg administered to each animal was 2 µg per 1-mg powder that was reconstituted in water and delivered by IP injection. Serum samples were collected 4 weeks after prime and two weeks after boost. Serum antibodies were determined using the standard ELISA and the results are summarized in FIG. 13.

Figure 13:
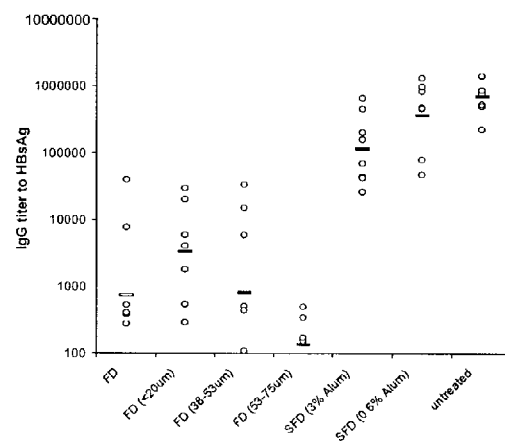
FIG. 13 shows the ELISA results obtained in Example 3, subpart 3.5.1, reported as anti-HBsAg antibody responses elicited in the immunized animals receiving "FD" (SFD composition formed from Alum hydroxide (3.0 w/v %), mannitol (1.9 w/v %), glycine (0.5 w/v %), and dextran (0.61 w/v %)); "FD <20 μm" (SFD composition formed from Alum hydroxide (3.0 w/v %), mannitol (1.9 w/v %), glycine (0.5 w/v %), and dextran (0.61 w/v %), particle size 20 μm fraction); "FD 38–53 μm" (SFD composition formed from Alum hydroxide (3.0 w/v %), mannitol (1.9 w/v %), glycine (0.5 w/v %), and dextran (0.61 w/v %), particle size 38–53 μm fraction); "FD 53–75 μm" (SFD composition formed from Alum hydroxide (3.0 w/v %), mannitol (1.9 w/v %), glycine (0.5 w/v %), and dextran (0.61 w/v %), particle size 53–78 μm fraction); "SFD 3% Alum" (SFD composition formed from Alum hydroxide (3.0 w/v %), mannitol (1.9 w/v %), glycine (0.5 w/v %), and dextran (0.61 w/v %)); "SFD 0.6% Alum" (SFD composition formed from Alum hydroxide (0.6 w/v %), mannitol (2.8 w/v %), glycine (1.2 w/v %), and dextran (0.58 w/v %)); and "untreated" the untreated control animals.

As can be seen in FIG. 13, compared to the untreated liquid vaccine (Control), the FD HBsAg vaccine composition (Group 1) showed diminished immunogenicity. In addition, the particle size of the alum-containing powder had a pronounced effect on immunogenicity of Alum-HBsAg. The immunogenicity of the freeze-dried formulations had an inverse correlation with the size of the particles (Groups 2, 3, and 4). The larger particle size fractions were less immunogenic than the smaller particle size fraction. This is consistent with the SDS-PAGE result and might be explained by the availability of HBsAg from the coagulated alum matrix. Smaller particles have a greater specific surface area, thereby allowing more HBsAg to be released from the alum matrix in vivo. An alternative explanation is that large coagulated particles are too big to be phagocytosed by antigen presenting cells, thus, the adsorbed vaccine antigen (HBsAg) is not available to the immune system. Regardless of the mechanism, this data clearly indicated that large size particles associated with coagulation also correlated with the loss of vaccine potency.

The SFD formulations (Q and R) elicited a significantly higher antibody response than the FD counterparts. This result confirms that alum coagulation caused an immunogenicity loss of HBsAg and that the fast freezing rate by SFD is an effective approach to preserving the alum adjuvant activity. The effect of alum concentration in the SFD powder formulation on immunogenicity is important. Although no clearly detectable coagulation was seen with SFD formulation Q, which contained 3.0 w/v % of Alum HBsAg, this formulation induced an antibody titer that was approximately 1-log of magnitude lower than the IM injection control. The SFD formulation with 0.6% alum content had no coagulation and induced an antibody titer that was indistinguishable from the IM injected animals (p>0.05, Student test). This result suggests that lowering alum concentration and fast freezing are the most effective formulation parameters in minimizing alum particle coagulation, thus, maximizing the immunogenicity of the vaccine.

3.5.2 EPI with Powdered Alum-DT

A commercial DT vaccine was used to illustrate the effect of the SFD process on an alum phosphate adjuvant-containing vaccine composition. The Alum-DT vaccine was dried by either conventional spray drying ("SD") or SFD, and the dried powder was then used to immunize hairless guinea pigs by using EPI. EPI delivers dry powder directly into the epidermal layer where abundant antigen presenting cells (APCs) can be activated to phagocytose or endocytose the dissolved antigen. The study design of the guinea pig study is shown below in Table 3.4.

TABLE 3.4

In vivo immunogenicity study for Alum-DT powder formulations.

| Group (n = 8) | Formulation | Powder Formation | Particle size | dT & tT dose/ mg powder |
|---|---|---|---|---|
| 1 | S | SD | 38–53 µm | 1.5 Lf/0.5 mg powder |
| 2 | T | SFD | 38–53 µm | 1.5 Lf/0.7 mg powder |
| 3 | Control | Liquid formulation | N/A | 1.5 Lf |

The formulations used in the study were as follows. Formulation S: alum phosphate (5 w/v %)/trehalose (5 w/v %). Formulation T: alum phosphate (1.5 w/v %)/trehalose (1.5 w/v %)/glycine (0.4 w/v %)/dextran (0.6 w/v %). Control: the commercial Alum-HBsAg product (Rhein Biotech) used as supplied by the manufacturer.

Formulation S (trehalose-based) was spray-dried using a laboratory-scale spray dryer (Mobile Minor, Niro, Inc). Formulation T, based on the combination of trehalose, glycine, and dextran, was produced using the SFD method of the present invention. For both powder formulations (Formulations S and T), the dried powder was subjected to a C/G/S technique (sieved to 38–53 µm size fraction) in order to match the size of the SD powders. A dose of 1.5 Lf for both dT and tT was used, which is equivalent to approximately 0.5-mg of the SD powders and 0.7-mg of the SFD powders based on total protein analysis.

Figure 14A:
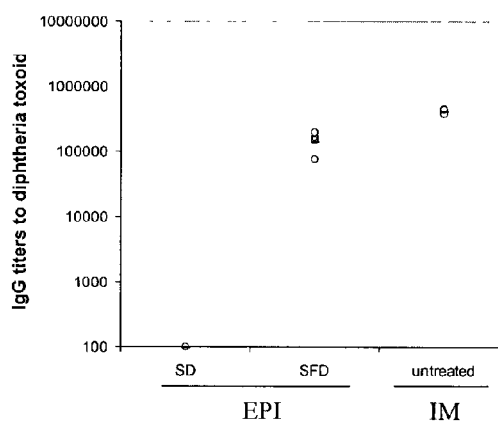
FIGS. 14a–14b show the ELISA results obtained in Example 3, subpart 3.5.2, reported as anti-dT (FIG. 14a) and anti-tT (FIG. 14b) antibody responses elicited in the immunized animals receiving either: (a) the "SFD" composition formed from alum phosphate (1.5 w/v %), trehalose (1.5 w/v %), glycine (0.4 w.v %), and dextran (0.6 w/v %), delivered by epidermal powder injection ("EPI"); (b) the "SD" composition formed from alum phosphate (5 w/v %) and trehalose (5 w/v %), delivered by EPI; or (c) the "untreated" composition which was a liquid DT vaccine composition administered by intramuscular (IM) injection.
Figure 14B:
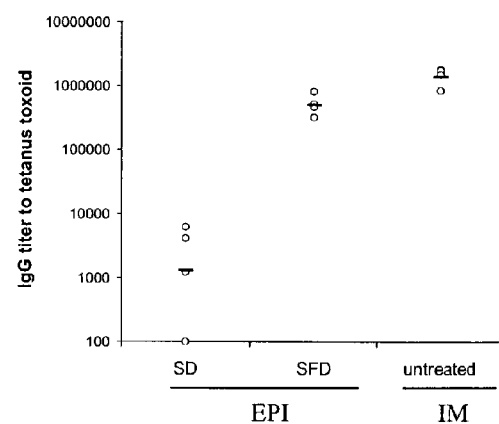

Further evaluation of alum coagulation by optical microscopy and particle size analysis revealed the same findings that alum particles were highly coagulated in the SD powder whereas the SFD powders yielded more gel-like suspensions upon rehydration. Serum samples were collected 4 weeks after prime and two weeks post boost. Serum antibodies were determined using the standard anti-dT and tT ELISA. The results are summarized in FIGS. 14a (anti-dT response) and 14b (anti-tT response). It is apparent that the SD formulation elicited either no (for dT, see FIG. 14a) or weak (for tT, see FIG. 14b) antibody responses. In contrast, however, the SFD formulation elicited significantly higher responses that were substantially equivalent to the responses induced by the untreated liquid vaccine (Control) that was injected intramuscularly.

EXAMPLE 4

Optimization of Alum-Adjuvanted Vaccine Compositions Prepared by SFD 4.1 Objectives:

To optimize the performance of SFD alum-adjuvanted vaccine powders and enhance the safety profile of the product by reducing alum content in the final composition, and to particularly address the following issues: (a) further reduction of gel coagulation; (b) reduction in local tolerability issues associated with alum adjuvants; and (c) increase in vivo potency of the vaccine composition when administered by EPI.

4.2 Materials:

The chemicals and excipients that were used in this study are summarized below in Table 4.1. All alum formulations were concentrated to a desired concentration by centrifugation (Allergra 6R centrifuge, Beckman Instrument, Palo Alto, Calif.) prior to use.

vanted hepatitis-B surface antigen ($AlPO_4$—HBsAg) where the alum content was 1/20 of the commercial product. The amount of the antigen was measured in vitro by SDS-PAGE or a micro BCA protein assay, and in vivo potency of the antigen was determined by intramuscular needle/syringe injection and EPI of mice. The local tolerability of SFD alum adsorbed diphtheria-tetanus toxoids (DT) vaccine administered by EPI was assessed in pigs and compared to intradermal (ID) injection.

TABLE 4.1

Chemicals/excipients used in the study.

| Chemical | Lot # | Source | Comment |
|---|---|---|---|
| Aluminum phosphate (Adjus-Phos, 2% $AlPO_4$) | 8934 | Accurate Chemical and Scientific (Westbury, NJ) | Manufactured by HCI Biosector (Frederikssund, Denmark) |
| Aluminum hydroxide (Alhydrogel, 3% $Al(OH)_3$) | | Accurate Chemical and Scientific | Manufactured by Superflos Biosector (Vedbaek, Denmark) |
| Diphtheria toxoid (dT, MW 58 kDa) | G9334 | Accurate Chemical and Scientific | Manufactured by Statens Serum Institute, Denmark, and provided at 5 mg/mL (1 Lf = 2.42 µg), used as supplied |
| Alum phosphate-adjuvanted DT | | CSL Limited (Parkville, Australia) | Bulk containing 5 w/v % alum phosphate adsorbed with both dT and tT at 563 Lf/mL |
| Alum hydroxide-adjuvanted hepatitis-B surface antigen (HBsAg) | | Rhein Amaericana S.A. (Buenos Ares, Argentina) | 20 µg HBsAg adsorbed to 0.5 mg of aluminum or 1.5-mg of aluminum hydroxide |
| Dextran (MW 10,000 Da) | 18H0568 | Sigma (St. Louis, MO) | Reagent grade |
| Glycine | 28H0103 | Sigma | Reagent grade |
| Sodium lauryl sulfate | 17H0459 | Sigma | Sodium dodecyl sulfate (SDS); MW = 288 Dalton |
| Mannitol | 127H0960 | Sigma | Reagent grade |
| Pluronic F68 | MPCS612B | BASF (Mount Olive, NJ) | Poloxamer 188NF; MW = 9,000 |
| Trehalose dihydrate | 28H3797 | Sigma | Reagent grade |
| Triton X-100 | 67H0044 | Sigma | t-Octylphenoxy-polyethyethanol; MW = 625 |
| Polysorbate 80 | 18H5229 | Sigma | Polyoxy-ethylene-sorbitan monooleate; MW = 1,310 |

4.3 Methods:

In general, placebo aluminum gels were formulated with a variety of pharmaceutical excipients and dehydrated by SFD. After drying, the dry powder was reconstituted and examined under optical microscopy to monitor gel coagulation. The degree of coagulation was also determined by the sedimentation rate of the gel. An optimized formulation process was then applied to prepare alum phosphate-adju-

4.3.1 Spray-Freezing-Drying (SFD)

The liquid formulation was delivered by the peristaltic pump (Model #77120-70, MasterFlex C/L, Barnant Company, Barrington, Ill.) at a flow rate of 2.0 mL/min into the ultrasonic atomizing system (Sono-Tek-Corporation, Milton, N.Y.) which consists of a spraying nozzle (Model #05793) and a power supply (Model #06-05108). The nozzle is equipped with a quasi-electric quartz crystal capable of vibrating at a specific frequency that determines the size of the droplets. The frequency of 60 kHz spraying nozzle produces droplets mostly within the range of 20–80 µm. Atomized droplets were sprayed into the liquid $N_2$-containing pan (16-cm in diameter by 6-cm in height). For formulations subjected to the spray-freezing/thawing experiment, the frozen powder was transferred to a glass vial and thawed under ambient conditions. For frozen droplets undergoing drying, the pan containing frozen particles in liquid nitrogen was transferred to a pre-cooled (−55° C.) shelf freeze dryer (Model #TDS2C2B5200, Dura-Stop, FTS System, Stone Ridge, N.Y.). Liquid nitrogen evaporated in a few minutes. The freeze-drying condition was set at −25° C. for 18 hours and 20° C. for 10 hours. The ramping rate was 1° C./minute consistently. The vacuum pressure was 100 mT throughout the cycle. At the end of drying, the powder-containing pans were transferred into a dry box purged with nitrogen (at <30% relative humidity) for powder collection. The same lyophilization cycle was used for freeze drying the liquid formulations as the freeze-dried samples.

4.3.2 Powder Formation by C/G/S Technique

To prepare powders of high density for EPI, some SFD formulations were compressed in a stainless steel dye of 13-mm in diameter (Carver Press, Wabash, Ind.) at a pressure of 12,000–15,000 pounds for 5–10 minutes. The compressed discs were ground manually using a mortar and pestle, and then the ground powder was manually sieved into the size fraction of 53–75 µm using 3-inch sieves (Fisher Scientific Products, Pittsburgh, Pa.).

4.3.3 Optical Microscopy

Visual analysis of the particles was performed using an optical microscope (Model DMR, Leica, Germany) with 10×-eyepiece lens and 10×-objective lens. The system was equipped with a Polaroid camera system for image output.

4.3.4 Scanning Electron Microscopy

The external morphology of particles was examined using an Amray 1810T scanning electron microscope (Amray, Bedford, Mass.). The powder sample was first sputtered coated with gold using a Hummer JR Technics unit (Pergamon Corporation, King of Prussia, Pa.).

4.3.5 Particle Size Analysis

The mean geometric/aerodynamic diameter of particles in the volume distribution was determined using a time-of-flight particle size analyzer (Aerosizer, API, Minneapolis, Minn.). The mean volumetric size was calculated using the equipment software and applying a density of 1.0 and such that the particle population between 10% ($D_{10}$) and 90% ($D_{90}$) could be determined for particle size distribution. Each analysis required approximately 3–5 mg of the powder sample.

4.3.6 X-ray Powder Diffraction (XRD)

XRD measurement was conducted using a 35 kV×15 mA Rigaku (D/max-β, CuKα radiation) X-ray diffractometer at room temperature and ambient humidity. Samples were scanned at 0.1 degrees/second with 1 second count time per increment. The range scanned was from 5 to 40 degrees.

4.3.7 Alum Gel Coagulation Analysis

Two methods were used to determine alum gel coagulation, optical microscopy and gel sedimentation. The powder sample was first reconstituted in water to a concentration of 100 mg/mL without agitation. The gel solution was pipetted on a glass slide and examined under an optical microscope (Model DMR, Leica, Germany). The same gel solution was then loaded in a 15-mL polystyrene conical tube (Falcon, Becton Dickinson, Franlkin Lakes, N.J.) and the sedimentation rate of the alum gel was monitored.

4.3.8 HBsAg Adsorption to Alum Phosphate

To prepare 500 vaccine doses where each dose contains 20 µg HBsAg adsorbed onto 25 µg $AlPO_4$ in 100 µL, 8.9 mL of HBsAg antigen (1.4 mg/mL, pH 5.5) was mixed with 2.83 mL of $AlPO_4$ adjuvant (Adju-Phos, 2% $AlPO_4$), 25 mL of 1.8% NaCl, and 13.3 mL of double-distilled water. The mixture was inverted 5 times and then gently stirred overnight at room temperature (RT). The pH was then raised to 7.2 and the mixture was centrifuged at 4,500 rpm for 20 min at RT. The supernatant was decanted and the pellet was re-suspended in 0.9% normal saline solution. The amount of protein in the supernatant was determined by BCA protein assay.

4.3.9 SDS-PAGE

Coomassie colloidal-stained SDS-polyacrylamide gel electrophoresis (SDS-PAGE) was performed on a Nu-PAGE gel from Novex (San Diego, Calif.) (4–12% MES, running buffer, sample buffer, and/or Dithiothreitol reducing agent). The alum-adjuvanted powder formulations was reconstituted in water and centrifuged to remove the supernatant. The alum pellet was re-suspended in 200 mM sodium phosphate, pH 7 with 0.1% SDS. The liquid suspension was then mixed with sample buffer from the Novex gel kit. The cocktail samples were then heated at 95° C. for 5 minutes and vortexed prior to loading on the gel. The gels were run for 35 minutes at 200V/120 mA/25 W using a power supply (PowerEase 500, Novex), and then coomassie stained (Novex Colloidal Blue Stain) and destained with water. The gel images were scanned on a gel scanner (Model GS-700 Imaging Densitometer, BioRad) equipped with a quantitation software (Quantity One), which can quantify the intensity of the gel bands. The unit of signal intensity is Optical Density (O.D.). All samples were compared against a molecular weight marker (Mark 12, Novex).

4.3.10 Immunization and Serum Collection

Hairless guinea pigs (Charles River, Wilmington, Mass.) were used to assess the immunogenicity of powder formulations following epidermal powder inejction as described above in Example 3. In general, the method of immunization was as follows. One mg of powder was dispensed into a trilaminate cassette. The cassette was inserted into the needleless syringe delivery device at the time of immunization. The device was placed against the left inguinal skin of the animals and actuated by releasing the compressed helium at 40-bar pressure from the gas cylinder. Control animals were immunized with 0.20 mL of liquid vaccine in saline by intramuscular (IM) injection using a 26 ½-gauge needle. Blood was collected via the kerotid blood vessel prior to each vaccination and two weeks post boost.

4.3.11 Local Reactogenicity Test

Pigs were anesthetized with a 1:1 mixture of Rompun and Telazol. The abdomen of each pig was tattooed on either side of the shot site. Each site received 2-mg powder formulation by EPI. Control sites received an intra-dermal (ID) injection of reconstituted powders or unprocessed liquid vaccine. After immunization, each injection site was inspected by palpation weekly.

Skin biopsies from the immunization sites were excised on day 42, fixed with 10% formalin, and embedded with paraffin. Sections of 6-μm thickness were cut, stained with hematoxylin and eosin (H&E), and visualized under a light microscope (Nikon, Melville, N.Y.).

4.3.12 ELISA

The antibody response to HBsAg was determined using a modified ELISA method (see, e.g., Chen et al. (2000) *Nature Med* 6:1187–1190). In particular a 96-well plate (Costar, Fisher Scientific Products, Pittsburg, Pa.) was coated with 0.1 μg of antigen in 30 mM phosphate buffered saline (PBS), pH 7.4, per well and allowed to sit overnight at 4° C. Plates were washed 3 times with tris-buffered saline (TBS), pH 7.4, containing 0.1% Brij-35, and incubated with test sera diluted in PBS containing 5% dry milk for 1.5 hour. A standard serum, containing a known level of antibodies to HBsAg, was added to each plate and used to standardize the titer in the final data analysis. The plates were then washed and incubated with biotin-labeled goat antibodies specific for mouse immunoglobulin IgG or IgG subclasses (1:8,000 in PBS, Southern Biotechnology Associate, Birmingham, Ala.) for 1 hour at room temperature. Following three additional washes, plates were incubated with streptavidin-horseradish peroxidase conjugates (Southern Biotechnology) for 1 hour at room temperature. Finally, plates were washed and developed with TMB substrate (Bio-Rad Laboratories, Melville, N.Y.). The endpoint titers of the sera were determined by 4-parameter analysis using the Softmax Pro 4.1 program (Molecular Devices, Sunnyvale, Calif.) and defined as the reciprocal of the highest serum dilution with an OD reading above the background by 0.1. A reference serum with a pre-determined titer was used on every plate to calibrate the titers and adjust assay-to-assay and plate-to-plate variation.

4.4 In Vivo Performance, Enhanced Safety:

The following study was carried out to demonstrate the improved safety of alum-adjuvanted vaccines prepared using the SFD methods of the present invention. In particular, granuloma formation was assessed. Granuloma formation is the most common side effect associated with alum-adjuvanted vaccines administered intradermally or subcutaneously.

4.4.1 Local Reactogenicity

The local reactogenicity to SFD alum-adjuvanted dT vaccine delivered using EPI was examined and compared with that of ID injection. The domestic white pig was chosen as an animal model for this test because it's epidermis is structurally similar to that of the human. Both EPI and ID injection with alum-adsorbed dT caused an erythema response (localized skin reaction). The size of the erythema area was observed to be larger and more intense for the EPI administrations. In all cases, the erythema completely resolved within 48 hours. The site of the EPI administrations appeared yellowish for an additional 2–3 days, but then restored to its normal color. becoming visually indistinguishable from normal skin 7 days post treatment. The study matrix and the results from the reactogenicity study are reported below in Table 4.2.

TABLE 4.2

Granuloma formation following administration of Alum-dT[1]

| | | | Granuloma sites out of a total ten sites | | | | | |
|---|---|---|---|---|---|---|---|---|
| Formulation | Alum | Route | D7 | D14 | D21 | D28 | D35 | D42 |
| liquid | Al(OH)3 | ID | 10 | 8 | 8 | 7 | 7 | 7 |
| liquid | AlPO4 | ID | 10 | 10 | 10 | 10 | 8 | 8 |
| Powder A[2] | Al(OH)3 | EPI | 0 | 0 | 0 | 0 | 0 | 0 |
| Powder B[2] | AlPO4 | EPI | 0 | 0 | 0 | 0 | 0 | 0 |

[1]Each site was treated with 500 µg of alum-absorbed dT (Alum-dT) by ID injection of liquid vaccine or EPI of SFD powdered vaccine on day 0. Granuloma formation was initially determined by weekly palpation for 6 weeks, and then confirmed by histology on day 42.
[2]Powder A and Powder B were produced by formulating the respective aluminum salt-adsorbed dT with 50% trehalose followed by a combined SFD and C/G/S process to produce 38–53 μm particles.

As can be seen, EPI administration of powdered compositions containing alum hydroxide or alum phosphate adjuvant did not result in granulomas as determined by visual examination (Table 4.2). In contrast, most of the ID injection sites had a solid lump that could be detected by palpation starting from day 7 and until the end of the study. At the end of the study (42 days post treatment), the sizes of the lumps in the animals receiving the ID liquid vaccine injections ranged in 0.3 to 0.5 mm in diameter and 0.2–0.3 mm in thickness.

The results of a histological examination of the EPI sites 42 days after treatment are depicted in FIGS. 15*a*–15*e*. In particular, histological examination showed a skin structure (see FIG. 15*b*) and cellular composition (FIG. 15*c*) that resembled those of normal skin (see FIG. 15*a*). The lumps from the ID injection sites were found to be typical granulomas, composed of inflammatory cells with a connective tissue capsule (FIG. 15*d*). The inflammatory cells were surrounded by a capsule of connective tissue that had completely replaced the normal tissue, again characteristic of granuloma formation. A closer examination showed that the main class of infiltrating cells were macrophages (see FIG. 15*e*). Both the alum hydroxide and alum phosphate liquid vaccine compositions induced granulomas when introduced by ID injection. These results demonstrate that EPI administration of the powdered vaccine compositions of the present invention provides a unique safety advantage over conventional administration routes.

4.5 Optimization of the Powder Formulation:

Formulation parameters affecting the stability of the alum gel were evaluated and optimized to produce SFD particles with minimal alum gel coagulation and superior particle characteristics suitable for epidermal powder injection techniques. In this regard, the SFD process had already been adjusted to achieve the greatest freeze rate possible by atomizing alum-containing liquid formulation into liquid nitrogen, thereby minimizing large-scale alum coagulation from occurring. In this study, the enhancing effects of various excipient combinations were investigated.

4.5.1 Effect of Excipient Composition

High particle density and appropriate particle size are two important powder properties that must be optimized for use in transdermal particle administrations such as EPI. It was expected that excipient composition would have a quantifiable influence on the density of the SFD powder, since voids left behind in the particles by evaporation of ice crystals may cave-in during drying. Accordingly, a series of alum hydroxide and alum phosphate compositions stabilized with various weight combinations of trehalose, mannitol and dextran excipients were prepared and then assessed for gel performance and particle characteristics. SFD particles were initially visually assessed using SEM, and the results from the study are depicted in FIGS. 16*a* and 16*b*. In particular, the combination of trehalose/mannitol/dextran=30%/30%/40% and a total solids content of 35 w/w % resulted in particles with a corrugated morphology. SEM demonstrated such morphology for the particles containing aluminium hydroxide at 36 μg/1-mg powder (FIG. 16*a*) and for these containing aluminium phosphate at 50 μg/1-mg powder (FIG. 16*b*), where the particles appear to have shrunk and thus become densified during the drying process.

Next, alum coagulation was evaluated using optical microscopy on reconstituted powders that had been prepared by either a FD or SFD process. The results are depicted in FIGS. 17*a*–17*d*, wherein FIG. 17*a* shows the FD alum hydroxide composition, FIG. 17*c* shows the FD alum phosphate composition, FIG. 17*b* shows the SFD alum hydroxide composition, and FIG. 17*d* shows the SFD alum phosphate composition. As can be seen, both FD formulations were highly coagulated when compared to their SFD counterparts. Sedimentation experiments confirmed that the FD suspensions had settled, i.e., the top solution became clear, in one minute but the SFD solutions took approximately 5 hours to clear. When the composition of trehalose/mannitol/dextran excipeint was varied, the density of the corresponding SFD powder also changed. However, the difference in coagulation was not distinguishable under optical microscopy. Interestingly, the reconstituted gel settled at faster rates as the content of mannitol was decreased. Sedimentation of aluminum phosphate (50 μg/1-mg powder) formulated in trehalose/mannitol/dextran at 40%/20%/40% completed, for example, in approximately 2 hours.

4.4.2 Effect of Surface-Active Agents

The stabilizing effect of four common surface-active agent excipients on the SFD alum-containing particles of the present invention were assessed. In particular, polysorbate 80 (786 Å, MW=1310), sodium lauryl sulfate (SDS), (53 Å, MW=288), Pluronic F68, a block copolymer of polyoxyethylene and polyoxyproplyene (MW=9,000), and Triton X-100, octylphenol ethylene oxide condensate, average MW=625 were selected for the study. All four surfactants were formulated with trehalose/mannitol/dextran excipeints (present at 30%/30%/40%) at 3 different concentrations, 0.5, 2, and 5% of the solid. Upon examination of each reconstituted suspension solution by optical microscopy and sedimentation, no significant differences in alum coagulation among the various surface-active agents were observed. However, powders containing the polysorbate 80, SDS, and Triton X-100 agents showed deteriorated powder flowability, particularly at higher concentrations.

4.4.3 Critical Concentration of Aluminum Salt

Although alum-adsorbed vaccines of low alum concentrations (<0.1 w/v %) have reportedly been freeze-dried with preserved immunogenicity (see, e.g., U.S. Pat. No. 4,578,270 and European Patent No. 0130619 B1), these formulations are impractical considering that most commercial alum-adjuvanted vaccines are administered at a much higher alum concentration, typically about 2–3 w/v %. However, as shown in Example 3 above, the specific formulations described in U.S. Pat. No. 4,578,270 and European Patent No. 0130619 B1 fail to stabilize alum salt from coagulation when freeze-dried at alum salt concentrations higher than 1%. Therefore, alum salt concentrations might play a critical role in alum coagulation. Our hypothesis is that alum salt coagulation might be unavoidable when the alum concentration exceeds a critical level, despite the effectiveness of fast freezing by SFD. To identify this critical concentration, numerous formulations of aluminum phosphate and hydroxide were prepared by SFD at different alum salt concentrations before SFD, excipient compositions, total solid concentrations, and payloads. Some of these formulations are summarized below in Table 4.3.

TABLE 4.3

Effect of alum concentration of the stability of SFD formulations[1]

| Sample | Liquid Alum Conc. Prior to SFD (mg/mL) | Alum content in SFD powder (μg/mg powder) | Total solid content prior to SFD (w/w %) | Coagulation |
|---|---|---|---|---|
| A | 26.5 | 76.0 | 35 | no |
| B | 30.3 | 76.0 | 40 | no |
| C | 34.0 | 114.0 | 30 | yes |
| D | 28.4 | 114.0 | 25 | no |
| E | 20.1 | 50.3 | 40 | no |
| F[2] | 11.5 | 28.7 | 40 | no |

[1]For all samples, alum phosphate was formulated with trehalose/mannitol/dextran at 30/30/40 wt % containing polysorbate 80 at 0.5% of the total solid except Samples E and F that contained Pluronic F68 at 0.1%.
[2]Alum hydroxide was formulated at the same composition as other formulations.

After SFD, the various sample formulations were assessed using optical microscopy to determine degree of alum gel coagulation. Results from the study are depicted in FIGS. 18*a*–18*d*. As a result of the assessment, it was found that concentration of alum salt in the liquid formulation prior to SFD appears to be the critical factor. In this regard, in the range of 26 to 34 mg/mL of alum salt in the liquid (starting) formulation, there is an obvious transition of alum gel into coagulated form. Optical microscopy on certain reconstituted powder formulations (the samples reported Table 4.3), revealed the following. Formulation A (26.5 mg/mL) was free from coagulation (see FIG. 18*a*). Some coagulated alum particles were observed in Formulation B at 30.3 mg/mL (see FIG. 18*b*). However, as the concentration of alum in the starting liquid was further increased to 34.0 mg/mL (Formulation C), alum coagulation became much more pronounced (see FIG. 18*c*). Alum coagulation had no direct correlation with the quantity of alum salt in the powder, as Formulations C. and D have the same alum content (114 μg/mg powder) and Formulation D was seen to be coagulation-free (see FIG. 18*d*). This is because Formulation D was prepared from the liquid suspension of alum salt at 28.4 mg/mL. Therefore, the critical alum salt concentration for the SFD process appeared to be 30 mg/mL in the liquid gel. A possible explanation for this is that the high-concentration alum gel forms a dense matrix and affects the pattern of ice formation, where ice crystals are less likely to push freeze concentrate into small compartments compared to the case where the alum gel concentration is lower. In addition, alum coagulation showed no correlation with the total solid content in the liquid gel prior to SFD (see Table 4.3). As higher total solid contents lead to more dense SFD particles, a total solid content of 35% or higher is preferred for producing powders for use in EPI.

4.6 In Vivo Performance of the SFD Vaccine Compositions:

Based upon the above optimization assessment, it was decided that the SFD formulation should optimally start with a liquid formulation containing at least about 30 mg/mL alum gel concentration and have a 35% total solid content. SFD of one human dose of the commercial alum adsorbed HBsAg vaccine, which contains 500 μg of alum adjuvant, will yield approximately 28 mg of dried powder. Thus, to reduce the dry mass, the amount of alum in the vaccine dose must be reduced. As indicated by the tolerability studies also described herein above, reduction in the alum in the vaccine should provide the added benefit of improving the tolerability of the SFD vaccine compositions. Accordingly, SFD powder vaccine compositions were made using 20 μg of the HBsAg antigen adsorbed to 25 μg alum phosphate adjuvant, and the immunogenicity of this formulation was determined using either EPI or IM injection (after reconstitution) of the SFD vaccine compositions and compared against the commercial vaccine that contains the same HBsAg dose, but 20 times more alum adjuvant.

4.6.1 Immunogenicity Studies

We first compared in hairless guinea pigs the immunogenicity of powdered formulations of HBsAg adjuvanted with either alum phosphate or alum hydroxide at a HBsAg: alum ratio of 1:25), denoted as Formulations E and F (Table 4.3), respectively. These formulations were administered by either EPI or IM injection of a liquid after the SFD particles were reconstituted. The results of the study are depicted in FIG. 19*a*. As can be seen, all groups showed a significant increase in the antibody response after the first and boost vaccinations (6 and 9 weeks after prime respectively) were administered (see FIG. 19*a*). The antibody titers in the animals vaccinated with the reconstituted powders were equivalent to that induced by the untreated liquid formulation vaccine (P>0.05), suggesting the suitability of SFD for stabilization of dry alum formulation. All animals vaccinated by EPI developed significant antibody titers. Interestingly, the two alum salts appear to be equally immunogenic when delivered as dry powders in the skin.

In a subsequent study, we evaluated the immunogenicity of the dry powder formulation containing $AlPO_4$ at 1/20 of the regular alum content, i.e. 20 µg of HBsAg adsorbed to 25 µg of aluminium. Because this high dose of vaccine can overwhelm the immune response in guinea pigs, the subjects were vaccinated with only 1/10 of the dose (2.0 µg HBsAg/2.5 µg of $ALPO_4$). The results of the study are depicted in FIG. 19b, where it can be seen that the SFD formulation was efficient in eliciting antibody responses by IM injection as a reconstituted powder. At 2 weeks post-boost, the highest antibody titers were detected in animals that received the SFD-reconstituted formulation with a geometric mean titer (GMT) of 5.6 (log 10). These titers were similar to those detected in animals that received the untreated liquid vaccine formulation (GMT=5.5 log 10) which contained twenty times more alum in the form of alum hydroxide, suggesting that alum dose in the commercial vaccine can be reduced without compromising the efficacy. This significantly reduced alum dose adds additional safety features to alum-adjuvanted vaccines delivered by EPI.

Accordingly, novel spray freeze-dried powder compositions and methods for producing these compositions have been described. Although preferred embodiments of the subject invention have been described in some detail, it is understood that obvious variations can be made without departing from the spirit and the scope of the invention as defined by the appended claims.

What is claimed is:

1. A process for the preparation of a powder for transdermal particle delivery via needleless injection, which process comprises the step of spray freeze-drying an aqueous solution or suspension via atomising the aqueous solution or suspension into a liquified gas followed by freeze-drying of the liquified gas containing the resulting frozen droplets of the aqueous solution or suspension, wherein said solution or suspension comprises a pharmaceutical agent, and has a solids content of 20% by weight or more, wherein alum is either absent or at a concentration of 30 mg/ml or less, wherein said pharmaceutical agent is selected from the group consisting of a peptide, a hormone, a nucleic acid, a gene construct, an antigen, an antibiotic, an anti-viral agent, an analgesic or analgesic combination, a local or general anaesthetic, and an anti-inflammatory, wherein the drying is conducted in the absence of an organic solvent, wherein said particles have a particle mass mean aerodynamic diameter (MMAD) of from 20 to 70 µm, a particle density of 0.7 to 1.5 g/cm$^3$ and display a reduction in MMAD of less than 20% in a particle attrition test comprising discharging the said powder via needleless injection into a flask containing a carrier fluid in which the powder is not soluble, and comparing the particle size distribution in the powder before and after needleless injection, and wherein the individual particles of the powder have a substantially spherical aerodynamic shape with a substantially uniform, non-porous surface, have a particle penetration energy suitable for transdermal delivery from a needleless syringe device, and are free-flowing under a dry environment.

2. The process according to claim 1, wherein the solution or suspension has a solids content of 30% by weight or more.

3. The process according to claim 2, wherein the solids content is 40% by weight or more.

4. The process according to claim 1, wherein the pharmaceutical agent is an antigen.

5. The process according to claim 4, wherein the antigen is adsorbed in an aluminum salt or calcium salt adjuvant.

6. The process according to claim 4, wherein the antigen is a bacterial or viral antigen.

7. The process according to claim 1, wherein the solution or suspension further comprises (a) an amorphous excipient selected from the group consisting of monosaccharides, disaccharides, oligosaccharides and polysaccharides; and (b) a crystalline excipient selected from the group consisting of carbohydrates, sugars and sugar alcohols.

8. The process according to claim 1, wherein the solution or suspension further comprises (a) an amorphous excipient selected from the group consisting of dextrose, sucrose, lactose, trehalose, cellobiose, raffinose, isomaltose and cyclodextrins, and (b) mannitol as a crystalline excipient.

9. The process according to claim 7, wherein the solution or suspension further comprises (c) a polymer.

10. The process according to claim 9, wherein the polymer is dextran.

11. The process according to claim 7, wherein the solution or suspension further comprises (d) an amino acid or a physiologically acceptable salt thereof.

12. The process according to claim 7, wherein the solution or suspension further comprises (c) a polymer and (d) an amino acid or physiologically acceptable salt thereof.

13. The process according to claim 1, wherein the solution or suspension further comprises trehalose, mannitol and dextran in a weight ratio of from about 3:3:4 to about 4:4:3.

14. The process according to claim 1, wherein the solution or suspension is sprayed from an ultrasonic nozzle.

15. The process according to claim 1, wherein the solution or suspension is sprayed into liquid nitrogen.

16. The process according to claim 1, wherein the solution or suspension is sprayed into a liquified gas and the liquified gas containing the resulting frozen droplets of the solution or suspension is subjected to a two stage drying process comprising:

(i) a first drying stage which is performed at a temperature of from about −50° C. to 0° C. for a period of about 4 to 24 hours under a pressure of about 20 to 500 mT; and (ii) a second drying stage which is performed at a temperature of from about 5 to 30° C. for a period of about 5 to 24 hours under a pressure of less than 100 mT.

17. The process according to claim 1, wherein the resulting spray freeze-dried particles are collected, washed and dried.

18. The process according to claim 17, wherein the dried particles are sieved.

* * * * *